(12) United States Patent
Obika et al.

(10) Patent No.: US 12,398,171 B2
(45) Date of Patent: Aug. 26, 2025

(54) 5'-MODIFIED NUCLEOSIDE AND NUCLEOTIDE USING SAME

(71) Applicant: Osaka University, Osaka (JP)

(72) Inventors: Satoshi Obika, Osaka (JP); Takao Yamaguchi, Osaka (JP); Takaki Habuchi, Osaka (JP); Go Kato, Osaka (JP); Takao Inoue, Osaka (JP); Tokuyuki Yoshida, Osaka (JP); Takaya Sugiura, Osaka (JP)

(73) Assignee: Osaka University, Osaka (JP)

( * ) Notice: Subject to any disclaimer, the term of this patent is extended or adjusted under 35 U.S.C. 154(b) by 1060 days.

(21) Appl. No.: 17/427,134

(22) PCT Filed: Jan. 31, 2020

(86) PCT No.: PCT/JP2020/003597
§ 371 (c)(1),
(2) Date: Feb. 25, 2022

(87) PCT Pub. No.: WO2020/158910
PCT Pub. Date: Aug. 6, 2020

(65) Prior Publication Data
US 2022/0372060 A1    Nov. 24, 2022

(30) Foreign Application Priority Data
Feb. 1, 2019    (JP) ................. 2019-016756

(51) Int. Cl.
*C07H 19/10*    (2006.01)
*C07H 19/20*    (2006.01)
*C07H 21/00*    (2006.01)

(52) U.S. Cl.
CPC ............. *C07H 19/10* (2013.01); *C07H 19/20* (2013.01); *C07H 21/00* (2013.01)

(58) Field of Classification Search
None
See application file for complete search history.

(56) References Cited

U.S. PATENT DOCUMENTS

2017/0044528 A1*    2/2017    Obika .................... C07H 19/16

FOREIGN PATENT DOCUMENTS

| CN | 108276463 A | 7/2018 |
|---|---|---|
| WO | 9422890 A1 | 10/1994 |
| WO | 2007134181 A2 | 11/2007 |
| WO | 2010048549 A2 | 4/2010 |
| WO | 2010048585 A2 | 4/2010 |
| WO | 2010077578 A1 | 7/2010 |
| WO | 2011139699 A2 | 11/2011 |
| WO | 2015116248 A1 | 8/2015 |
| WO | 2015125783 A1 | 8/2015 |
| WO | 2020166551 A1 | 8/2020 |

OTHER PUBLICATIONS

Zhao and Caruthers et al., "Synthesis and Preliminary Biochemical Studies with 5'-Deoxy-5'-methylidyne Phosphonate Linked Thymidine Oligonucleotides", Tetrahedron Letters, 1996, vol. 37, No. 35, pp. 6239-6242.
Koshkin and Lomholt et al., "A Simplified and Efficient Route to 2'-O, 4'-C-Methylene-Linked Bicyclic Ribonucleosides (Locked Nucleic Acid)", J. Org. Chem., 2001, vol. 66, No. 25, pp. 8504-8512.
Wexsellblatt et al., "ppGpp analogues inhibit synthetase activity of Rel proteins from Gram-negative and Gram-postive bacteria", Bioorganic & Medicinal Chemistry, 2010, vol. 18, No. 12, pp. 4485-4497.
Shimo and Obika et al., "Design and evaluation of locked nucleic acid-based splice-switching. Oligonucleotides in vitro", Nucleic Acids Research, 2014, vol. 42, No. 12, pp. 8174-8187.
PCT/JP2020/003597; PCT International Search Report of the International Searching Authority dated Mar. 6, 2020 and its English translation.
Horiba, M. et al., "Synthesis of scpBNA-mC, -A, and -G Monomers and Evaluation of the Binding Affinities of scpBNA-Modified Oligonucleotides toward Complementary ssRNA and ssDNA", the Journal of Organic Chemistry, 2016, vol. 81, No. 22, pp. 11000-11008.
S.Obika et al., T. Tetrahedron Lett. 1997, 38, 8735-8738.
S. Singh et al., J. Chem. Commun. 1998, 455-456.
Yawman et al., J. Org. Chem. 1995, 60, 788-789.
Manoharan et al., J. Org. Chem. 2016, 81, 2261-2279.

* cited by examiner

*Primary Examiner* — Patrick T Lewis
(74) *Attorney, Agent, or Firm* — Renner, Otto, Boisselle & Sklar, LLP

(57) ABSTRACT

Disclosed are a 5'-modified nucleoside and a nucleotide using the same. The nucleoside of the present invention is represented by the formula (I) below. The 5'-modified nucleoside of the present invention is usable as a substitute for a phosphorothioate-modified nucleic acid, which has a risk of, for example, accumulation in a specific organ. The 5'-modified nucleoside also has excellent industrial productivity because a diastereomer separation step is not involved in the production process thereof.

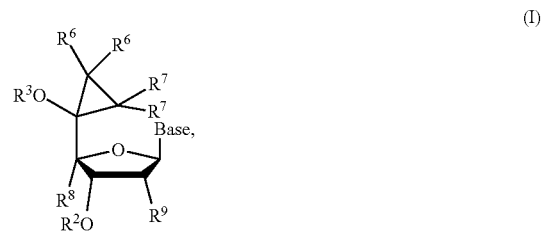

(I)

17 Claims, 3 Drawing Sheets
Specification includes a Sequence Listing.

[FIG.1]
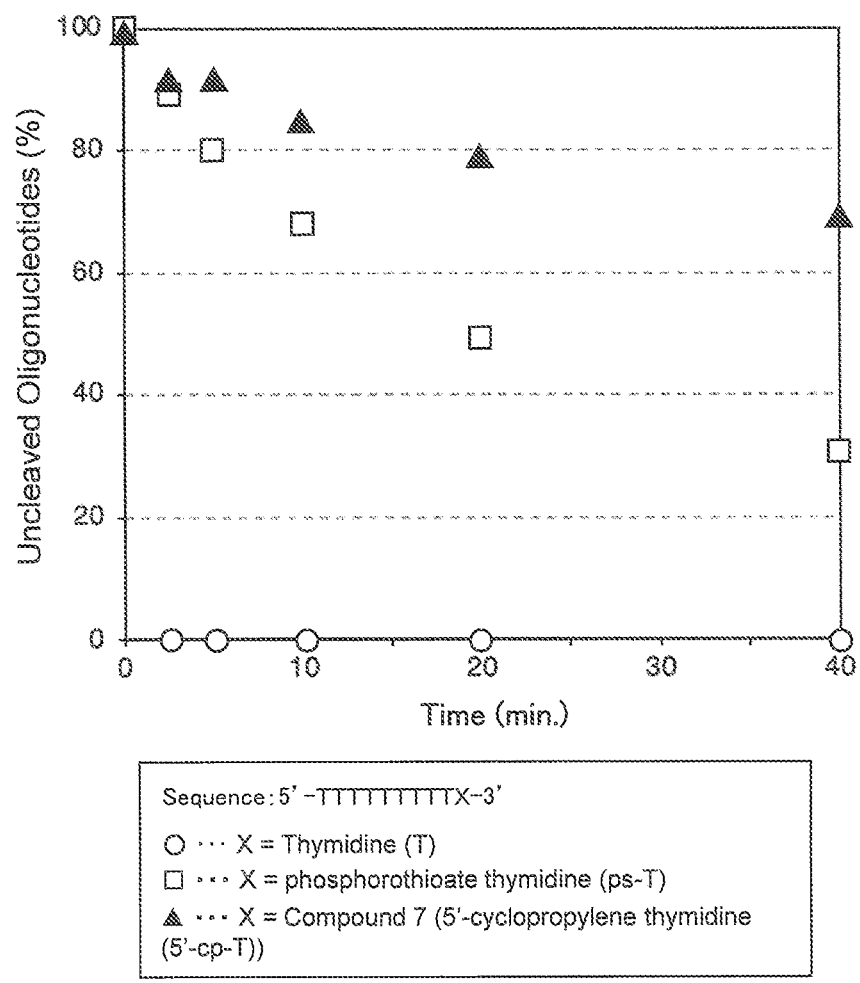

[FIG.2]
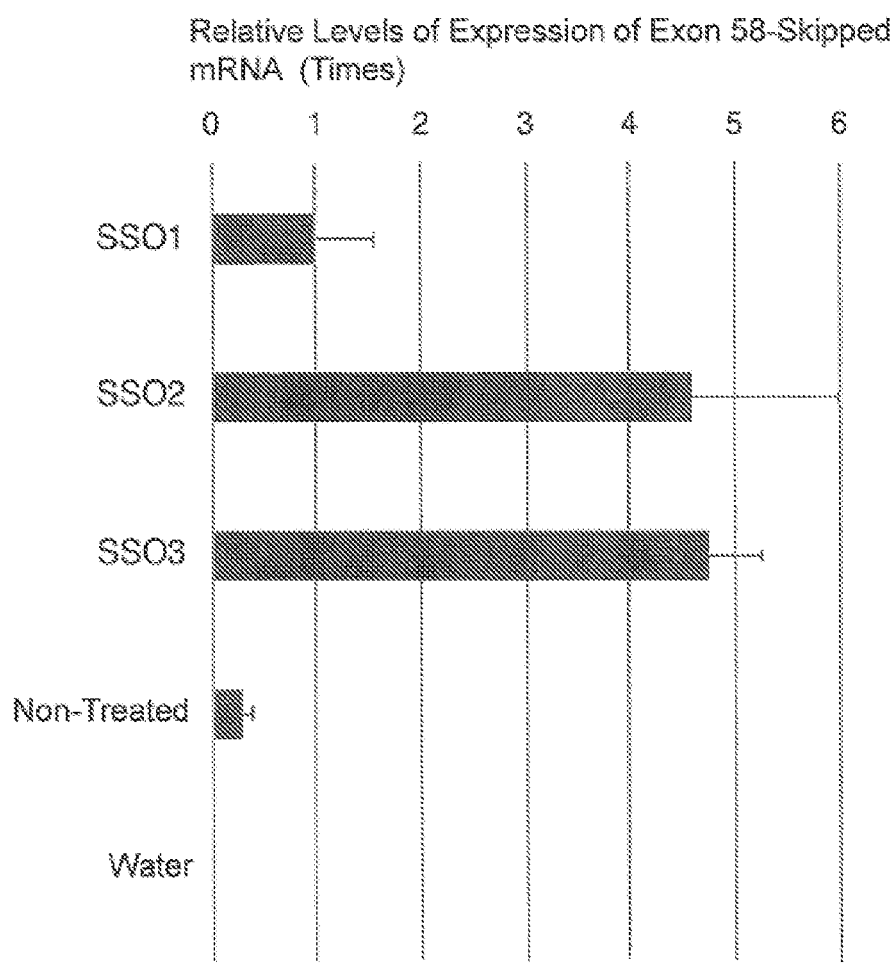

[FIG.3]
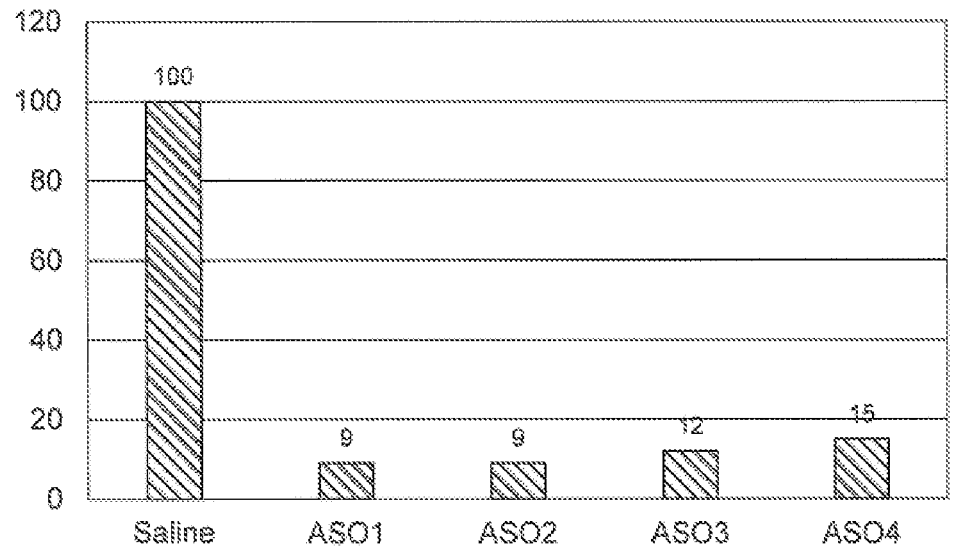
[FIG.4]
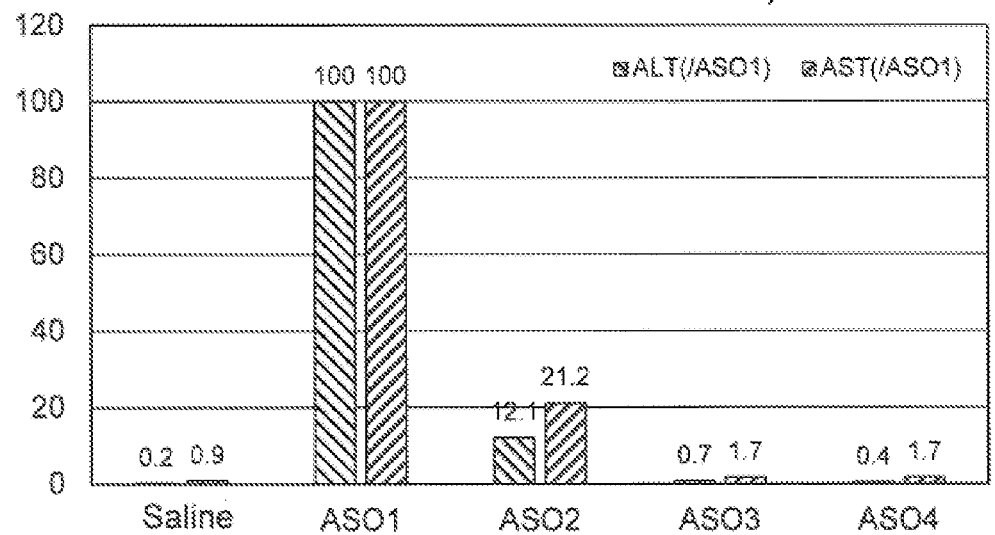

```
                            SEQUENCE LISTING

<160> NUMBER OF SEQ ID NOS: 37

<210> SEQ ID NO 1
<211> LENGTH: 12
<212> TYPE: DNA
<213> ORGANISM: Artificial Sequence
<220> FEATURE:
<223> OTHER INFORMATION: Sequence (1): synthesized oligonucleotide
      including thymidine at the 6th position tested for double-strand
      forming ability in Example 10

<400> SEQUENCE: 1
gcgttttttg ct                                                          12

<210> SEQ ID NO 2
<211> LENGTH: 12
<212> TYPE: DNA
<213> ORGANISM: Artificial Sequence
<220> FEATURE:
<223> OTHER INFORMATION: Sequence (2): synthesized oligonucleotide
      including 5'-cyclopropylenethymidine (5'-cp-T) at the 6th position
      tested for double-strand forming ability in Example 10
<220> FEATURE:
<221> NAME/KEY: misc_feature
<222> LOCATION: (6)..(6)
<223> OTHER INFORMATION: t = 5'-cyclopropylenethymidine (5'-cp-T)

<400> SEQUENCE: 2
gcgttttttg ct                                                          12

<210> SEQ ID NO 3
<211> LENGTH: 12
<212> TYPE: DNA
<213> ORGANISM: Artificial Sequence
<220> FEATURE:
<223> OTHER INFORMATION: Sequence (3): synthesized oligonucleotide
      including cytidine at the 6th position tested for double-strand
      forming ability in Example 10

<400> SEQUENCE: 3
gcgttctttg ct                                                          12

<210> SEQ ID NO 4
<211> LENGTH: 12
<212> TYPE: DNA
<213> ORGANISM: Artificial Sequence
<220> FEATURE:
<223> OTHER INFORMATION: Sequence (4): synthesized oligonucleotide
      including 5'-cyclopropylene-5-methyl-2'-deoxycytidine (5'-cp-MeC)
      at the 6th position tested for double-strand forming ability in
      Example 10
<220> FEATURE:
<221> NAME/KEY: misc_feature
<222> LOCATION: (6)..(6)
<223> OTHER INFORMATION: c = 5'-cyclopropylene-5-methyl-2'-deoxycytidine
      (5'-cp-MeC)

<400> SEQUENCE: 4
gcgttctttg ct                                                          12

<210> SEQ ID NO 5
<211> LENGTH: 12
<212> TYPE: DNA
<213> ORGANISM: Artificial Sequence
```

```
<220> FEATURE:
<223> OTHER INFORMATION: Sequence (5): synthesized oligonucleotide
      including adenosine at the 6th position tested for double-strand
      forming ability in Example 10

<400> SEQUENCE: 5
gcgttatttg ct                                                              12

<210> SEQ ID NO 6
<211> LENGTH: 12
<212> TYPE: DNA
<213> ORGANISM: Artificial Sequence
<220> FEATURE:
<223> OTHER INFORMATION: Sequence (6): synthesized oligonucleotide
      including 5'-cyclopropylene-2'-deoxyadenosine (5'-cp-A) at the 6th
      position tested for double-strand forming ability in Example 10
<220> FEATURE:
<221> NAME/KEY: misc_feature
<222> LOCATION: (6)..(6)
<223> OTHER INFORMATION: a = 5'-cyclopropylene-2'-deoxyadenosine
      (5'-cp-A)

<400> SEQUENCE: 6
gcgttatttg ct                                                              12

<210> SEQ ID NO 7
<211> LENGTH: 12
<212> TYPE: DNA
<213> ORGANISM: Artificial Sequence
<220> FEATURE:
<223> OTHER INFORMATION: Sequence (7): synthesized oligonucleotide
      including guanosine at the 6th position tested for double-strand
      forming ability in Example 10

<400> SEQUENCE: 7
gcgttgtttg ct                                                              12

<210> SEQ ID NO 8
<211> LENGTH: 12
<212> TYPE: DNA
<213> ORGANISM: Artificial Sequence
<220> FEATURE:
<223> OTHER INFORMATION: Sequence (8): synthesized oligonucleotide
      including 5'-cyclopropylene-2'-deoxyguanosine (5'-cp-G) at the 6th
      position tested for double-strand forming ability in Example 10
<220> FEATURE:
<221> NAME/KEY: misc_feature
<222> LOCATION: (6)..(6)
<223> OTHER INFORMATION: g = 5'-cyclopropylene-2'-deoxyguanosine
      (5'-cp-G)

<400> SEQUENCE: 8
gcgttgtttg ct                                                              12

<210> SEQ ID NO 9
<211> LENGTH: 12
<212> TYPE: DNA
<213> ORGANISM: Artificial Sequence
<220> FEATURE:
<223> OTHER INFORMATION: Sequence (9): synthesized oligonucleotide
      including LNA-G at the 6th position tested for double-strand
      forming ability in Example 10
<220> FEATURE:
<221> NAME/KEY: misc_feature
<222> LOCATION: (6)..(6)
<223> OTHER INFORMATION: g = LNA-G

<400> SEQUENCE: 9
gcgttgtttg ct                                                              12
```

```
<210> SEQ ID NO 10
<211> LENGTH: 12
<212> TYPE: DNA
<213> ORGANISM: Artificial Sequence
<220> FEATURE:
<223> OTHER INFORMATION: Sequence (10): synthesized oligonucleotide
      including 5'-cyclopropylene-LNA-G (5'-cp-LNA-G) at the 6th
      position tested for double-strand forming ability in Example 10
<220> FEATURE:
<221> NAME/KEY: misc_feature
<222> LOCATION: (6)..(6)
<223> OTHER INFORMATION: g = 5'-cyclopropylene-LNA-G (5'-cp-LNA-G)

<400> SEQUENCE: 10
gcgttgtttg ct                                                      12

<210> SEQ ID NO 11
<211> LENGTH: 12
<212> TYPE: RNA
<213> ORGANISM: Artificial Sequence
<220> FEATURE:
<223> OTHER INFORMATION: Target 1 oligoRNA

<400> SEQUENCE: 11
agcaaaaaac gc                                                      12

<210> SEQ ID NO 12
<211> LENGTH: 12
<212> TYPE: DNA
<213> ORGANISM: Artificial Sequence
<220> FEATURE:
<223> OTHER INFORMATION: Target 1 oligoDNA

<400> SEQUENCE: 12
agcaaaaaac gc                                                      12

<210> SEQ ID NO 13
<211> LENGTH: 12
<212> TYPE: RNA
<213> ORGANISM: Artificial Sequence
<220> FEATURE:
<223> OTHER INFORMATION: Target 2 oligoRNA

<400> SEQUENCE: 13
agcaaagaac gc                                                      12

<210> SEQ ID NO 14
<211> LENGTH: 12
<212> TYPE: DNA
<213> ORGANISM: Artificial Sequence
<220> FEATURE:
<223> OTHER INFORMATION: Target 2 oligoDNA

<400> SEQUENCE: 14
agcaaagaac gc                                                      12

<210> SEQ ID NO 15
<211> LENGTH: 12
<212> TYPE: RNA
<213> ORGANISM: Artificial Sequence
<220> FEATURE:
<223> OTHER INFORMATION: Target 3 oligoRNA

<400> SEQUENCE: 15
agcaaauaac gc                                                      12
```

```
<210> SEQ ID NO 16
<211> LENGTH: 12
<212> TYPE: DNA
<213> ORGANISM: Artificial Sequence
<220> FEATURE:
<223> OTHER INFORMATION: Target 3 oligoDNA

<400> SEQUENCE: 16
agcaaataac gc                                                              12

<210> SEQ ID NO 17
<211> LENGTH: 12
<212> TYPE: RNA
<213> ORGANISM: Artificial Sequence
<220> FEATURE:
<223> OTHER INFORMATION: Target 4 oligoRNA

<400> SEQUENCE: 17
agcaaacaac gc                                                              12

<210> SEQ ID NO 18
<211> LENGTH: 12
<212> TYPE: DNA
<213> ORGANISM: Artificial Sequence
<220> FEATURE:
<223> OTHER INFORMATION: Target 4 oligoDNA

<400> SEQUENCE: 18
agcaaacaac gc                                                              12

<210> SEQ ID NO 19
<211> LENGTH: 14
<212> TYPE: DNA
<213> ORGANISM: Artificial Sequence
<220> FEATURE:
<223> OTHER INFORMATION: Sequence (11): synthesized oligonucleotide
      without 5'-cyclopropylenethymidine (5'-cp-T) tested for RNase H
      Activity in Example 12
<220> FEATURE:
<221> NAME/KEY: misc_feature
<222> LOCATION: (1)..(3)
<223> OTHER INFORMATION: 2'-o-methyl modified
<220> FEATURE:
<221> NAME/KEY: misc_feature
<222> LOCATION: (12)..(14)
<223> OTHER INFORMATION: 2'-o-methyl modified

<400> SEQUENCE: 19
gcgttttttt tgcu                                                            14

<210> SEQ ID NO 20
<211> LENGTH: 14
<212> TYPE: DNA
<213> ORGANISM: Artificial Sequence
<220> FEATURE:
<223> OTHER INFORMATION: Sequence (12): synthesized oligonucleotide with
      two bases of 5'-cyclopropylenethymidine (5'-cp-T) tested for RNase
      H Activity in Example 12
<220> FEATURE:
<221> NAME/KEY: misc_feature
<222> LOCATION: (1)..(3)
<223> OTHER INFORMATION: 2'-o-methyl modified
<220> FEATURE:
<221> NAME/KEY: misc_feature
<222> LOCATION: (7)..(7)
<223> OTHER INFORMATION: t = 5'-cyclopropylenethymidine (5'-cp-T)
<220> FEATURE:
<221> NAME/KEY: misc_feature
<222> LOCATION: (11)..(11)
<223> OTHER INFORMATION: t = 5'-cyclopropylenethymidine (5'-cp-T)
<220> FEATURE:
```

```
<221> NAME/KEY: misc_feature
<222> LOCATION: (12)..(14)
<223> OTHER INFORMATION: 2'-o-methyl modified

<400> SEQUENCE: 20
gcgttttttt tgcu                                                            14

<210> SEQ ID NO 21
<211> LENGTH: 14
<212> TYPE: DNA
<213> ORGANISM: Artificial Sequence
<220> FEATURE:
<223> OTHER INFORMATION: Sequence (13): synthesized oligonucleotide with
      three bases of 5'-cyclopropylenethymidine (5'-cp-T) tested for
      RNase H Activity in Example 1
<220> FEATURE:
<221> NAME/KEY: misc_feature
<222> LOCATION: (1)..(3)
<223> OTHER INFORMATION: 2'-o-methyl modified
<220> FEATURE:
<221> NAME/KEY: misc_feature
<222> LOCATION: (5)..(5)
<223> OTHER INFORMATION: t = 5'-cyclopropylenethymidine (5'-cp-T)
<220> FEATURE:
<221> NAME/KEY: misc_feature
<222> LOCATION: (8)..(8)
<223> OTHER INFORMATION: t = 5'-cyclopropylenethymidine (5'-cp-T)
<220> FEATURE:
<221> NAME/KEY: misc_feature
<222> LOCATION: (11)..(11)
<223> OTHER INFORMATION: t = 5'-cyclopropylenethymidine (5'-cp-T)
<220> FEATURE:
<221> NAME/KEY: misc_feature
<222> LOCATION: (12)..(14)
<223> OTHER INFORMATION: 2'-o-methyl modified

<400> SEQUENCE: 21
gcgttttttt tgcu                                                            14

<210> SEQ ID NO 22
<211> LENGTH: 14
<212> TYPE: RNA
<213> ORGANISM: Artificial Sequence
<220> FEATURE:
<223> OTHER INFORMATION: Complementary RNA

<400> SEQUENCE: 22
agcaaaaaaa acgc                                                            14

<210> SEQ ID NO 23
<211> LENGTH: 15
<212> TYPE: DNA
<213> ORGANISM: Artificial Sequence
<220> FEATURE:
<223> OTHER INFORMATION: SSO1
<220> FEATURE:
<221> NAME/KEY: misc_feature
<222> LOCATION: (2)..(2)
<223> OTHER INFORMATION: c = LNA-5-methylcytosine
<220> FEATURE:
<221> NAME/KEY: misc_feature
<222> LOCATION: (4)..(4)
<223> OTHER INFORMATION: c = LNA-5-methylcytosine
<220> FEATURE:
<221> NAME/KEY: misc_feature
<222> LOCATION: (6)..(6)
<223> OTHER INFORMATION: c = LNA-5-methylcytosine
<220> FEATURE:
<221> NAME/KEY: misc_feature
<222> LOCATION: (8)..(8)
<223> OTHER INFORMATION: t = LNA-t
<220> FEATURE:
<221> NAME/KEY: misc_feature
```

```
<222> LOCATION: (10)..(10)
<223> OTHER INFORMATION: a = LNA-a
<220> FEATURE:
<221> NAME/KEY: misc_feature
<222> LOCATION: (12)..(12)
<223> OTHER INFORMATION: g = LNA-g
<220> FEATURE:
<221> NAME/KEY: misc_feature
<222> LOCATION: (14)..(14)
<223> OTHER INFORMATION: c = LNA-5-methylcytosine

<400> SEQUENCE: 23
tccctcttga aggcc                                                    15

<210> SEQ ID NO 24
<211> LENGTH: 15
<212> TYPE: DNA
<213> ORGANISM: Artificial Sequence
<220> FEATURE:
<223> OTHER INFORMATION: SSO2
<220> FEATURE:
<221> NAME/KEY: misc_feature
<222> LOCATION: (1)..(1)
<223> OTHER INFORMATION: phosphorothioate modified
<220> FEATURE:
<221> NAME/KEY: misc_feature
<222> LOCATION: (2)..(2)
<223> OTHER INFORMATION: c = LNA-5-methylcytosine
<220> FEATURE:
<221> NAME/KEY: misc_feature
<222> LOCATION: (4)..(4)
<223> OTHER INFORMATION: c = LNA-5-methylcytosine
<220> FEATURE:
<221> NAME/KEY: misc_feature
<222> LOCATION: (6)..(6)
<223> OTHER INFORMATION: c = LNA-5-methylcytosine
<220> FEATURE:
<221> NAME/KEY: misc_feature
<222> LOCATION: (8)..(8)
<223> OTHER INFORMATION: t = LNA-t
<220> FEATURE:
<221> NAME/KEY: misc_feature
<222> LOCATION: (10)..(10)
<223> OTHER INFORMATION: a = LNA-a
<220> FEATURE:
<221> NAME/KEY: misc_feature
<222> LOCATION: (11)..(11)
<223> OTHER INFORMATION: phosphorothioate modified
<220> FEATURE:
<221> NAME/KEY: misc_feature
<222> LOCATION: (12)..(12)
<223> OTHER INFORMATION: g = LNA-g
<220> FEATURE:
<221> NAME/KEY: misc_feature
<222> LOCATION: (14)..(14)
<223> OTHER INFORMATION: c = LNA-5-methylcytosine
<220> FEATURE:
<221> NAME/KEY: misc_feature
<222> LOCATION: (14)..(14)
<223> OTHER INFORMATION: phosphorothioate modified

<400> SEQUENCE: 24
tccctcttga aggcc                                                    15

<210> SEQ ID NO 25
<211> LENGTH: 15
<212> TYPE: DNA
<213> ORGANISM: Artificial Sequence
<220> FEATURE:
<223> OTHER INFORMATION: SSO3
<220> FEATURE:
<221> NAME/KEY: misc_feature
<222> LOCATION: (1)..(1)
<223> OTHER INFORMATION: t = 5'-cyclopropylenethymidine
<220> FEATURE:
```

```
<221> NAME/KEY: misc_feature
<222> LOCATION: (2)..(2)
<223> OTHER INFORMATION: c = LNA-5-methylcytosine
<220> FEATURE:
<221> NAME/KEY: misc_feature
<222> LOCATION: (4)..(4)
<223> OTHER INFORMATION: c = LNA-5-methylcytosine
<220> FEATURE:
<221> NAME/KEY: misc_feature
<222> LOCATION: (6)..(6)
<223> OTHER INFORMATION: c = LNA-5-methylcytosine
<220> FEATURE:
<221> NAME/KEY: misc_feature
<222> LOCATION: (8)..(8)
<223> OTHER INFORMATION: t = LNA-t
<220> FEATURE:
<221> NAME/KEY: misc_feature
<222> LOCATION: (10)..(10)
<223> OTHER INFORMATION: a = LNA-a
<220> FEATURE:
<221> NAME/KEY: misc_feature
<222> LOCATION: (12)..(12)
<223> OTHER INFORMATION: g = 5'-cyclopropylene-LNA- G
<220> FEATURE:
<221> NAME/KEY: misc_feature
<222> LOCATION: (14)..(14)
<223> OTHER INFORMATION: c = LNA-5-methylcytosine
<220> FEATURE:
<221> NAME/KEY: misc_feature
<222> LOCATION: (15)..(15)
<223> OTHER INFORMATION: c = 5'-cyclopropylene-5-methyl-2'-deoxycytidine

<400> SEQUENCE: 25
tccctcttga aggcc                                                        15

<210> SEQ ID NO 26
<211> LENGTH: 20
<212> TYPE: DNA
<213> ORGANISM: Artificial Sequence
<220> FEATURE:
<223> OTHER INFORMATION: DMD Forward primer

<400> SEQUENCE: 26
agttctgacc agtggaagcg                                                   20

<210> SEQ ID NO 27
<211> LENGTH: 20
<212> TYPE: DNA
<213> ORGANISM: Artificial Sequence
<220> FEATURE:
<223> OTHER INFORMATION: DMD Reverse primer

<400> SEQUENCE: 27
cctcaggagg cagctcctat                                                   20

<210> SEQ ID NO 28
<211> LENGTH: 20
<212> TYPE: DNA
<213> ORGANISM: Artificial Sequence
<220> FEATURE:
<223> OTHER INFORMATION: RPLP2 Forward primer

<400> SEQUENCE: 28
tggacagcgt gggtatcgag                                                   20

<210> SEQ ID NO 29
<211> LENGTH: 20
<212> TYPE: DNA
<213> ORGANISM: Artificial Sequence
<220> FEATURE:
<223> OTHER INFORMATION: RPLP2 Reverse primer
```

-continued

<400> SEQUENCE: 29
ctgggcaatg acgtcttcaa                                               20

<210> SEQ ID NO 30
<211> LENGTH: 14
<212> TYPE: DNA
<213> ORGANISM: Artificial Sequence
<220> FEATURE:
<223> OTHER INFORMATION: ASO1
<220> FEATURE:
<221> NAME/KEY: misc_feature
<222> LOCATION: (1)..(1)
<223> OTHER INFORMATION: g = LNA-g
<220> FEATURE:
<221> NAME/KEY: misc_feature
<222> LOCATION: (2)..(2)
<223> OTHER INFORMATION: t = LNA-t
<220> FEATURE:
<221> NAME/KEY: misc_feature
<222> LOCATION: (3)..(3)
<223> OTHER INFORMATION: c = LNA-5-methylcytosine
<220> FEATURE:
<221> NAME/KEY: misc_feature
<222> LOCATION: (12)..(12)
<223> OTHER INFORMATION: t = LNA-t
<220> FEATURE:
<221> NAME/KEY: misc_feature
<222> LOCATION: (13)..(14)
<223> OTHER INFORMATION: g = LNA-g

<400> SEQUENCE: 30
gtctctttac ctgg                                                     14

<210> SEQ ID NO 31
<211> LENGTH: 14
<212> TYPE: DNA
<213> ORGANISM: Artificial Sequence
<220> FEATURE:
<223> OTHER INFORMATION: ASO2
<220> FEATURE:
<221> NAME/KEY: misc_feature
<222> LOCATION: (1)..(1)
<223> OTHER INFORMATION: g = LNA-g
<220> FEATURE:
<221> NAME/KEY: misc_feature
<222> LOCATION: (2)..(2)
<223> OTHER INFORMATION: t = LNA-t
<220> FEATURE:
<221> NAME/KEY: misc_feature
<222> LOCATION: (3)..(3)
<223> OTHER INFORMATION: c = LNA-5-methylcytosine
<220> FEATURE:
<221> NAME/KEY: misc_feature
<222> LOCATION: (4)..(4)
<223> OTHER INFORMATION: t = 5'-cyclopropylenethymidine
<220> FEATURE:
<221> NAME/KEY: misc_feature
<222> LOCATION: (12)..(12)
<223> OTHER INFORMATION: t = LNA-t
<220> FEATURE:
<221> NAME/KEY: misc_feature
<222> LOCATION: (13)..(14)
<223> OTHER INFORMATION: g = LNA-g

<400> SEQUENCE: 31
gtctctttac ctgg                                                     14

<210> SEQ ID NO 32
<211> LENGTH: 14
<212> TYPE: DNA
<213> ORGANISM: Artificial Sequence
<220> FEATURE:

```
<223> OTHER INFORMATION: ASO3
<220> FEATURE:
<221> NAME/KEY: misc_feature
<222> LOCATION: (1)..(1)
<223> OTHER INFORMATION: g = LNA-g
<220> FEATURE:
<221> NAME/KEY: misc_feature
<222> LOCATION: (2)..(2)
<223> OTHER INFORMATION: t = LNA-t
<220> FEATURE:
<221> NAME/KEY: misc_feature
<222> LOCATION: (3)..(3)
<223> OTHER INFORMATION: c = LNA-5-methylcytosine
<220> FEATURE:
<221> NAME/KEY: misc_feature
<222> LOCATION: (7)..(7)
<223> OTHER INFORMATION: t = 5'-cyclopropylenethymidine
<220> FEATURE:
<221> NAME/KEY: misc_feature
<222> LOCATION: (12)..(12)
<223> OTHER INFORMATION: t = LNA-t
<220> FEATURE:
<221> NAME/KEY: misc_feature
<222> LOCATION: (13)..(14)
<223> OTHER INFORMATION: g = LNA-g

<400> SEQUENCE: 32
gtctctttac ctgg                                                        14

<210> SEQ ID NO 33
<211> LENGTH: 14
<212> TYPE: DNA
<213> ORGANISM: Artificial Sequence
<220> FEATURE:
<223> OTHER INFORMATION: ASO4
<220> FEATURE:
<221> NAME/KEY: misc_feature
<222> LOCATION: (1)..(1)
<223> OTHER INFORMATION: g = LNA-g
<220> FEATURE:
<221> NAME/KEY: misc_feature
<222> LOCATION: (2)..(2)
<223> OTHER INFORMATION: t = LNA-t
<220> FEATURE:
<221> NAME/KEY: misc_feature
<222> LOCATION: (3)..(3)
<223> OTHER INFORMATION: c = LNA-5-methylcytosine
<220> FEATURE:
<221> NAME/KEY: misc_feature
<222> LOCATION: (4)..(4)
<223> OTHER INFORMATION: t = 5'-cyclopropylenethymidine
<220> FEATURE:
<221> NAME/KEY: misc_feature
<222> LOCATION: (8)..(8)
<223> OTHER INFORMATION: t = 5'-cyclopropylenethymidine
<220> FEATURE:
<221> NAME/KEY: misc_feature
<222> LOCATION: (12)..(12)
<223> OTHER INFORMATION: t = LNA-t
<220> FEATURE:
<221> NAME/KEY: misc_feature
<222> LOCATION: (13)..(14)
<223> OTHER INFORMATION: g = LNA-g

<400> SEQUENCE: 33
gtctctttac ctgg                                                        14

<210> SEQ ID NO 34
<211> LENGTH: 20
<212> TYPE: DNA
<213> ORGANISM: Artificial Sequence
<220> FEATURE:
<223> OTHER INFORMATION: NR3C1 forward

<400> SEQUENCE: 34
```

```
actgtccagc atgccgctat                                          20

<210> SEQ ID NO 35
<211> LENGTH: 20
<212> TYPE: DNA
<213> ORGANISM: Artificial Sequence
<220> FEATURE:
<223> OTHER INFORMATION: NR3C1 reverse

<400> SEQUENCE: 35
gcagtggctt gctgaattcc                                          20

<210> SEQ ID NO 36
<211> LENGTH: 20
<212> TYPE: DNA
<213> ORGANISM: Artificial Sequence
<220> FEATURE:
<223> OTHER INFORMATION: GAPDH forward

<400> SEQUENCE: 36
gtgtgaacgg atttggccgt                                          20

<210> SEQ ID NO 37
<211> LENGTH: 20
<212> TYPE: DNA
<213> ORGANISM: Artificial Sequence
<220> FEATURE:
<223> OTHER INFORMATION: GAPDH reverse

<400> SEQUENCE: 37
gacaagcttc ccattctcgg                                          20
```

5'-MODIFIED NUCLEOSIDE AND NUCLEOTIDE USING SAME

This application is a national phase of International Application No. PCT/JP2020/003597 filed 31 Jan. 2020, which claims priority to Japan Application No. 2019-016756 filed 1 Feb. 2019, the entireties of which are hereby incorporated by reference.

TECHNICAL FIELD

The present invention relates to a 5'-modified nucleoside and a nucleotide using the same. More specifically, the invention relates to a 5'-modified nucleoside that has good nuclease-resistant ability and can be produced with high efficiency, and a nucleotide using the same.

BACKGROUND ART

Treatments of disorders using nucleic acid drugs include antisense therapies, antigene therapies, aptamers, siRNAs, and the like. An antisense therapy is the procedure for treatment or prevention of diseases involving inhibiting a translation process of pathogenic RNAs by externally introducing oligonucleotides (antisense strands) complementary to disease-associated mRNAs to form the double strands. The mechanism of siRNAs is similar to that of the antisense therapies, involving inhibiting translation from mRNAs to proteins by administration of double-stranded RNAs to the body. Meanwhile, in the antigene therapies, transcription of DNA to RNA is suppressed by externally introducing triple-strand-forming oligonucleotides corresponding to the DNA sites transcribed into the pathogenic RNA. Aptamers, which are small nucleic acid molecules (oligonucleotides), exert their functions by binding to disease-related biological components, such as proteins.

Various artificial nucleic acids have been developed as materials for such nucleic acid drugs. In particular, 2',4'-BNA (bridged nucleic acid, also known as LNA) in which the conformation of the sugar moiety in the nucleic acid is fixed through cross-linking has been reported to have excellent binding affinity for a single-stranded RNA (ssRNA) (Non-Patent Documents 1 and 2), and is expected to be suitable for various nucleic acid drugs for antisense therapies and the like.

Meanwhile, an artificial nucleic acid obtained by introducing a methyl group into the 5' position of a nucleic acid has been reported to have excellent properties in terms of the nuclease-resistant ability (Patent Documents 1 to 3). Therefore, an artificial nucleic acid obtained by introducing a substituent into the 5' position is also expected to have applications to diagnosis and medicine.

However, synthesis of such an artificial nucleic acid obtained by introducing a substituent into the 5' position involves separation of diastereomers (Non-Patent Documents 3 and 4), and thus, the production process is complicated as a whole. Therefore, further development for enabling industrial production thereof is desired.

RELATED ART DOCUMENTS

Patent Document

Patent Document 1: WO2010/048549
Patent Document 2: WO2010/048585
Patent Document 3: WO2010/077578

Non-Patent Document

Non-Patent Document 1: S. Obika et al., T. Tetrahedron Lett. 1997, 38, 8735-8738
Non-Patent Document 2: S. Singh et al., J. Chem. Commun. 1998, 455-456
Non-Patent Document 3: Yawman et al., J. Org. Chem. 1995, 60, 788-789
Non-Patent Document 4: Manoharan et al., J. Org. Chem. 2016, 81, 2261-2279

SUMMARY OF INVENTION

Problem to be Solved by the Invention

The present invention was made to address the above-described problems, and it is an object thereof to provide a nucleoside modified at the 5' position that has good nuclease-resistant ability and can be produced with high efficiency without involving the separation of diastereomers in the synthetic pathway thereto, and a nucleotide using the same.

The present invention is a compound represented by a formula (I) below or a salt thereof:

[Chemical Formula 1]

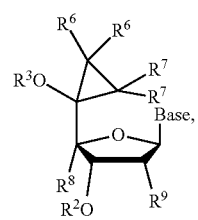

(I)

wherein Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms;

$R^2$ and $R^3$ each independently represent a hydrogen atom, a hydroxy group protecting group for nucleic acid synthesis, a $C_1$ to $C_7$ alkyl group that may be branched or form a ring, a $C_2$ to $C_7$ alkenyl group that may be branched or form a ring, a $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —P(R$^4$)R$^5$, wherein R$^4$ and R$^5$ each independently represent a hydroxy group, a hydroxy group protected by a protecting group for nucleic acid synthesis, a mercapto group, a mercapto group protected by a protecting group for nucleic acid synthesis, an amino group, a $C_1$ to $C_6$ alkoxy group, a $C_1$ to $C_6$ alkylthio group, a $C_1$ to $C_6$ cyanoalkoxy group, or a dialkylamino group having a $C_1$ to $C_6$ alkyl group;

R$^6$ and R$^7$ are each independently a hydrogen atom, a halogen atom, or a methyl group; and R$^8$ is a hydrogen atom, and R$^9$ is a hydrogen atom or a halogen atom; a $C_1$ to $C_6$ linear alkoxy group that may be substituted with a $C_1$ to $C_6$ linear alkoxy group; or —OR$^{10}$, wherein R$^{10}$ is a hydrogen atom or a hydroxy group protecting group for nucleic acid synthesis, or R$^8$ and R$^9$ together represent a divalent group represented by a formula below:

[Chemical Formula 2]

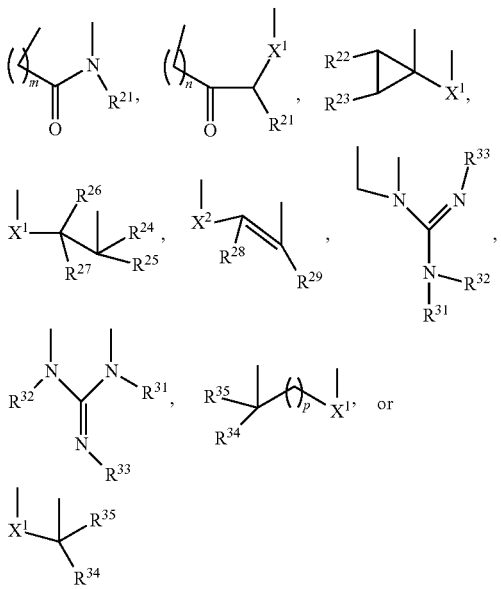

wherein R$^{21}$ is a hydrogen atom, a $C_1$ to $C_6$ alkyl group that may be branched or form a ring, a $C_2$ to $C_6$ alkenyl group that may be branched or form a ring, a $C_3$ to $C_{10}$ aryl group that may have any one or more substituents selected from the α group and that may contain a heteroatom, an aralkyl group with an a $C_3$ to $C_{12}$ aryl moiety that may have any one or more substituents selected from the α group and that may contain a heteroatom, or an amino group protecting group for nucleic acid synthesis;

R$^{22}$ and R$^{23}$ are each independently a hydrogen atom, a $C_1$ to $C_6$ alkyl group that may be substituted with a $C_3$ to $C_{12}$ aryl group that may contain a heteroatom, and that may be branched or form a ring, or an aralkyl group with a $C_3$ to $C_{12}$ aryl moiety that may contain a heteroatom, or R$^{22}$ and R$^{23}$ together represent —(CH$_2$)$_q$—, wherein q is an integer from 2 to 5;

R$^{24}$ and R$^{25}$ are each independently a group selected from the group consisting of a hydrogen atom, a hydroxy group, a $C_1$ to $C_6$ alkyl group that may be branched or form a ring, a $C_1$ to $C_6$ alkoxy group that may be branched or form a ring, an amino group, an amino group, and an amino group protected by a protecting group for nucleic acid synthesis, or R$^{24}$ and R$^{25}$ together represent =C(R$^{36}$)R$^{37}$, wherein R$^{36}$ and R$^{37}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group a $C_1$ to $C_6$ linear or branched alkylthio group, a $C_1$ to $C_6$ linear or branched alkylthio group, a $C_1$ to $C_6$ cyanoalkoxy group, or a $C_1$ to $C_6$ linear or branched alkylamino group;

R$^{26}$ and R$^{27}$ are each independently a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

R$^{28}$ is a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

R$^{29}$ is a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

R$^{31}$, R$^{32}$, and R$^{33}$ are each independently a hydrogen atom, a $C_1$ to $C_6$ alkyl group that may be branched or form a ring, or an amino group protecting group for nucleic acid synthesis;

R$^{34}$ and R$^{35}$ are each independently a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

m is an integer from 0 to 2;

n is an integer of 0 or 1;

p is an integer of 0 or 1;

X$^1$ is an oxygen atom, a sulfur atom, or an amino group; and

X$^2$ is an oxygen atom or a sulfur atom.

In one embodiment, the Base in the formula (I) is a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimiclin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimiclin-1-yl group, a 2-oxo-4 mercapto-1,2-dihydropyrimiclin-1-yl group, a 2-oxo-4-hydroxy-1,2-dihydropyrimidin-1-yl group, a 2-oxo-4-hydroxy-5-methyl-1,2-dihydropyrimiclin-1-yl group, or a 4-amino-5-methyl-2-oxo-1,2-dihydropyrimiclin-1-yl group.

In one embodiment, the Base in the formula (I) is a group represented by a formula below:

[Chemical Formula 3]

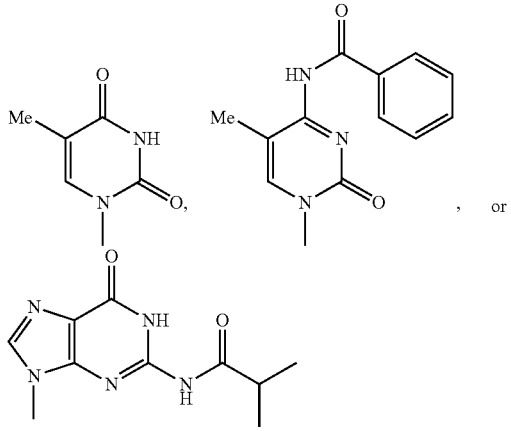

, or

In one embodiment, $R^6$ and $R^7$ in the formula (I) are both hydrogen atoms.

In one embodiment, $R^8$ and $R^9$ in the formula (I) are both hydrogen atoms.

The present invention is also an oligonucleotide containing at least one nucleoside structure represented by a formula (II) below or a pharmacologically acceptable salt thereof:

[Chemical Formula 4]

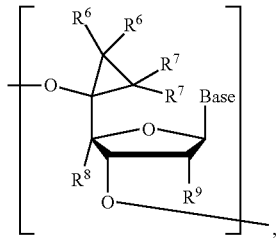

(II)

wherein Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms;

$R^6$ and $R^7$ are each independently a hydrogen atom, a halogen atom, or a methyl group; and $R^8$ is a hydrogen atom, and $R^9$ is a hydrogen atom, a halogen atom, or a $C_1$ to $C_6$ linear alkoxy group that may be substituted with a $C_1$ to $C_6$ linear alkoxy group, or $R^8$ and $R^9$ together represent a divalent group represented by a formula below:

[Chemical Formula 5]

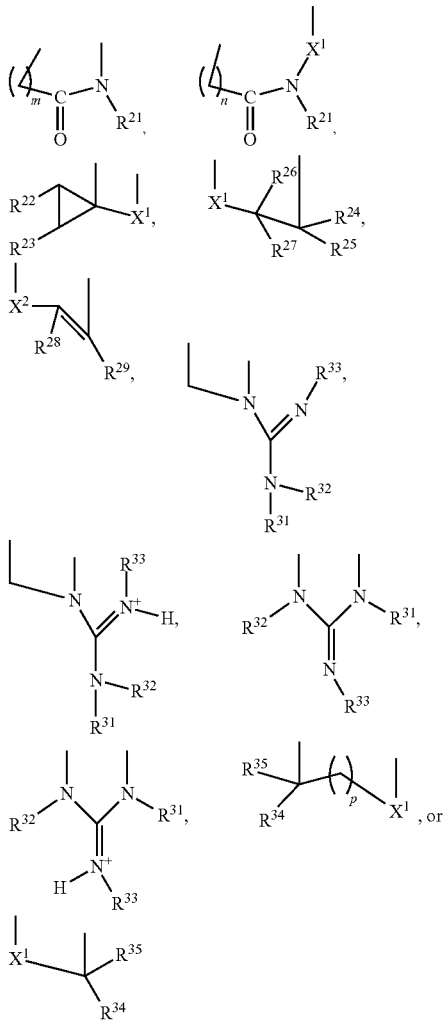

wherein $R^{21}$ is a hydrogen atom, a $C_1$ to $C_6$ alkyl group that may be branched or form a ring, a $C_2$ to $C_6$ alkenyl group that may be branched or form a ring, an $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, or an amino group protecting group for nucleic acid synthesis;

$R^{22}$ and $R^{23}$ are each independently a hydrogen atom, a $C_1$ to $C_6$ alkyl group that may be substituted with a $C_3$ to $C_{12}$ aryl group that may contain a heteroatom, and that may be branched or form a ring, or an aralkyl group with a $C_3$ to $C_{12}$ aryl moiety that may contain a heteroatom, or $R^{22}$ and $R^{23}$ together represent $-(CH_2)_q-$, wherein q is an integer from 2 to 5;

$R^{24}$ and $R^{25}$ are each independently a group selected from the group consisting of a hydrogen atom, a hydroxy group, a $C_1$ to $C_6$ alkyl group that may be branched or form a ring, a $C_1$ to $C_6$ alkoxy group that may be branched or form a ring, an amino group, and an amino group protected by a protecting group for nucleic acid synthesis, or $R^{24}$ and $R^{25}$ together represent =$C(R^{36})R^{37}$, wherein $R^{36}$ and $R^{37}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group;

$R^{26}$ and $R^{27}$ are each independently a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

$R^{28}$ is a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

$R^{29}$ is a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

$R^{31}$, $R^{32}$, and $R^{33}$ are each independently a hydrogen atom, a $C_1$ to $C_6$ alkyl group that may be branched or form a ring, or an amino group protecting group for nucleic acid synthesis;

$R^{34}$ and $R^{35}$ are each independently a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

m is an integer from 0 to 2;
n is an integer of 0 or 1;
p is an integer of 0 or 1;
$X^1$ is an oxygen atom, a sulfur atom, or an amino group; and
$X^2$ is an oxygen atom or a sulfur atom.

In one embodiment, $R^6$ and $R^7$ in the formula (II) are both hydrogen atoms.

In one embodiment, $R^8$ and $R^9$ in the formula (II) are both hydrogen atoms.

The present invention is a method for producing the above oligonucleotide or pharmacologically acceptable salt thereof, which comprises:

synthesizing an oligonucleotide using a compound represented by a formula (I) below or a pharmacologically acceptable salt thereof:

[Chemical Formula 6]

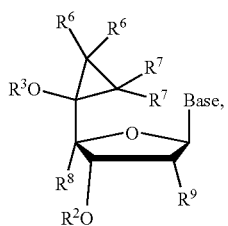

(I)

wherein Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms;

$R^2$ and $R^3$ each independently represent a hydrogen atom, a hydroxy group protecting group for nucleic acid synthesis, a $C_1$ to $C_7$ alkyl group that may be branched or form a ring, a $C_2$ to $C_7$ alkenyl group that may be branched or form a ring, a $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —$P(R^4)R^5$, wherein $R^4$ and $R^5$ each independently represent a hydroxy group, a hydroxy group protected by a protecting group for nucleic acid synthesis, a mercapto group, a mercapto group protected by a protecting group for nucleic acid synthesis, an amino group, a $C_1$ to $C_6$ alkoxy group, a $C_1$ to $C_6$ alkylthio group, a $C_1$ to $C_6$ cyanoalkoxy group, or a dialkylamino group having a $C_1$ to $C_6$ alkyl group;

$R^6$ and $R^7$ are each independently a hydrogen atom, a halogen atom, or a methyl group; and $R^8$ is a hydrogen atom, and $R^9$ is a hydrogen atom or a halogen atom; $C_1$ to $C_6$ linear alkoxy group that may be substituted with a $C_1$ to $C_6$ linear alkoxy group; or —$OR^{10}$, wherein $R^{10}$ is a hydrogen atom or a hydroxy group protecting group for nucleic acid synthesis, or $R^8$ and $R^9$ together represent a divalent group represented by a formula below:

[Chemical Formula 7]

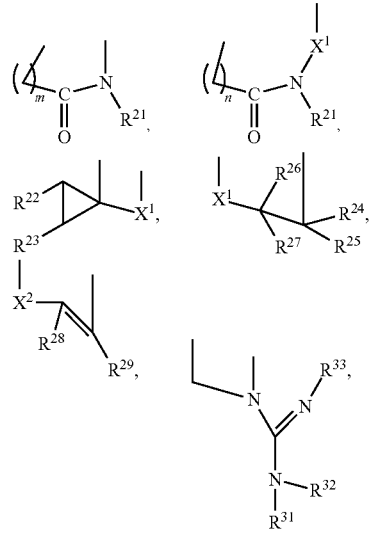

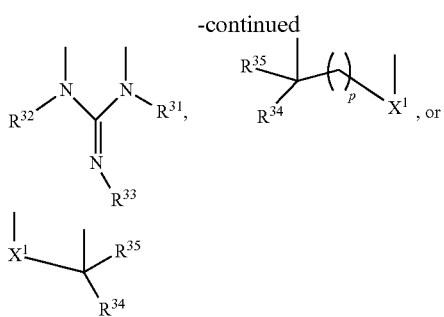

wherein $R^{21}$ is a hydrogen atom, a $C_1$ to $C_6$ alkyl group that may be branched or form a ring, a $C_2$ to $C_6$ alkenyl group that may be branched or form a ring, $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, or an amino group protecting group for nucleic acid synthesis;

$R^{22}$ and $R^{23}$ are each independently a hydrogen atom, a $C_1$ to $C_6$ alkyl group that may be substituted with a $C_3$ to $C_{12}$ aryl group that may contain a heteroatom, and that may be branched or form a ring, or an aralkyl group with a $C_3$ to $C_{12}$ aryl moiety that may contain a heteroatom, or $R^{22}$ and $R^{23}$ together represent $-(CH_2)_q-$, wherein q is an integer from 2 to 5;

$R^{24}$ and $R^{25}$ are each independently a group selected from the group consisting of a hydrogen atom, a hydroxy group, a $C_1$ to $C_6$ alkyl group that may be branched or form a ring, a $C_1$ to $C_6$ alkoxy group that may be branched or form a ring, an amino group, an amino group, and an amino group protected by a protecting group for nucleic acid synthesis, or $R^{24}$ and $R^{25}$ together represent $=C(R^{36})R^{37}$, wherein $R^{36}$ and $R^{37}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group;

$R^{26}$ and $R^{27}$ are each independently a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

$R^{28}$ is a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

$R^{29}$ is a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

$R^{31}$, $R^{32}$, and $R^{33}$ are each independently a hydrogen atom, a $C_1$ to $C_6$ alkyl group that may be branched or form a ring, or an amino group protecting group for nucleic acid synthesis;

$R^{34}$ and $R^{35}$ are each independently a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

m is an integer from 0 to 2;
n is an integer of 0 or 1;
p is an integer of 0 or 1;
$X^1$ is an oxygen atom, a sulfur atom, or an amino group; and
$X^2$ is an oxygen atom or a sulfur atom.

Effects of the Invention

According to the present invention, a novel 5'-modified nucleoside and a nucleotide using the same are provided. The 5'-modified nucleoside of the present invention is also usable as a substitute for a phosphorothioate-modified nucleic acid, which has a risk of, for example, accumulation in a specific organ. The 5'-modified nucleoside of the present invention also has excellent industrial productivity because a diastereomer separation step is not involved in the production process thereof.

BRIEF DESCRIPTION OF DRAWINGS

FIG. 1 is a graph showing changes in the percentage of uncleaved oligonucleotides over time when various types of oligonucleotides having the sequence of 5'-TTTTTTTTTX-3' were treated with 3'-exonuclease.

FIG. 2 is a graph showing relative levels of expression of exon 58-skipped mRNA of the dystrophin gene produced using various types of oligonucleotides.

FIG. 3 is a graph showing the abundances of mRNA of a target gene NR3C1 in mouse livers in the cases where test oligonucleotides ASO1, ASO2, ASO3, and ASO4 were administered and in the case where saline was administered, and shows antisense effects of the various types of oligonucleotides as relative values of the mRNA abundance, where the mRNA abundance in the case where saline was administered is taken as 100.

FIG. 4 is a graph showing the activities of aspartate transaminase (AST) and alanine transaminase (ALT) in blood in the cases where the test oligonucleotides ASO1, ASO2, ASO3, and ASO4 were administered and in the case where saline was administered, and shows the activities as relative values of the AST and ALT, where the AST value and the ALT value in the case where ASO1 was administered are taken as 100.

DESCRIPTION OF EMBODIMENTS

The following definitions shall apply throughout the specification.

The term "$C_1$ to $C_6$ linear alkyl group" as used herein refers to any linear alkyl group having 1 to 6 carbon atoms, and specifically to a methyl group, an ethyl group, an n-propyl group, an n-butyl group, an n-pentyl group, or an n-hexyl group. On the other hand, the term "$C_1$ to $C_6$ alkyl group" refers to any linear, branched, or cyclic alkyl group having 1 to 6 carbon atoms.

The term "$C_1$ to $C_6$ linear alkoxy group" as used herein encompasses alkoxy groups including any linear alkyl groups having 1 to 6 carbon atoms. Examples thereof include a methoxy group, an ethoxy group, and an n-propoxy group. On the other hand, the term "$C_1$ to $C_6$ alkoxy group" refers to any linear, branched, or cyclic alkoxy group having 1 to 6 carbon atoms. The term "$C_1$ to $C_6$ linear alkoxy group that may be substituted with a $C_1$ to $C_6$ linear alkoxy group" refers to the "$C_1$ to $C_6$ linear alkoxy group" as well as an alkoxy group obtained by substituting one or more hydrogen atoms included in the "$C_1$ to $C_6$ linear alkoxy group" with another or other "$C_1$ to $C_6$ linear alkoxy group" that may be the same or different. Examples of such "$C_1$ to $C_6$ linear alkoxy group that may be substituted with a $C_1$ to $C_6$ linear alkoxy group" include a methoxy group, an ethoxy group, an n-propoxy group, a methoxymethoxy group, an ethoxymethoxy group, an n-propoxymethoxy group, a methoxyethoxy group (e.g., a 2-methoxyethoxy group), an ethoxyethoxy group (e.g., a 2-ethoxyethoxy group), and an n-propoxyethoxy group.

The term "$C_1$ to $C_6$ cyanoalkoxy group" as used herein refers to a group obtained by substituting at least one hydrogen atom included in any linear, branched, or cyclic alkoxy group having 1 to 6 carbon atoms with a cyano group.

The term "$C_1$ to $C_6$ linear alkylthio group" as used herein encompasses alkylthio groups including any linear alkyl groups having 1 to 6 carbon atoms. Examples thereof include a methythio group, an ethylthio group, and an n-propylthio group. On the other hand, the term "$C_1$ to $C_6$ linear alkylthio group" refers to any linear, branched, or cyclic alkylthio group having 1 to 6 carbon atoms.

The term "$C_1$ to $C_6$ linear alkylamino group" as used herein encompasses alkylamino groups including one or two alkylamino groups with any linear alkyl group having 1 to 6 carbon atoms. Examples thereof include a methylamino group, a dimethylamino group, an ethylamino group, a methylethylamino group, and a diethylamino group.

The term "$C_1$ to $C_7$ alkyl group that may be branched or form a ring" as used herein encompasses any linear alkyl groups having 1 to 7 carbon atoms, any branched alkyl groups having 3 to 7 carbon atoms, and any cyclic alkyl groups having 3 to 7 carbon atoms. Such groups may also be referred to merely as "lower alkyl groups". Examples of any linear alkyl groups having 1 to 7 carbon atoms include a methyl group, an ethyl group, an n-propyl group, an n-butyl group, an n-pentyl group, an n-hexyl group, and an n-heptyl group; examples of any branched alkyl groups having 3 to 7 carbon atoms include an isopropyl group, an isobutyl group, a tert-butyl group, and an isopentyl group; and examples of any cyclic alkyl groups having 3 to 7 carbon atoms include a cyclobutyl group, a cyclopentyl group, and a cyclohexyl group.

The term "$C_2$ to $C_7$ alkenyl group that may be branched or form a ring" as used herein encompasses any linear alkenyl groups having 2 to 7 carbon atoms, any branched alkenyl groups having 3 to 7 carbon atoms, and any cyclic alkenyl groups having 3 to 7 carbon atoms. Such groups may also be referred to merely as "lower alkenyl groups". Examples of any linear alkenyl groups having 2 to 7 carbon atoms include an ethenyl group, a 1-propenyl group, a 2-propenyl group, a 1-butenyl group, a 2-butenyl group, a 1-pentenyl group, a 2-pentenyl group, a 3-pentenyl group, a 4-pentenyl group, and a 1-hexenyl group; examples of any branched alkenyl groups having 3 to 7 carbon atoms include an isopropenyl group, a 1-methyl-1-propenyl group, a 1-methyl-2-propenyl group, a 2-methyl-1-propenyl group, a 2-methyl-2-propenyl group, and a 1-methyl-2-butenyl group; and examples of any cyclic alkenyl groups having 3 to 7 carbon atoms include a cyclobutenyl group, a cyclopentenyl group, and a cyclohexenyl group.

The term "$C_3$ to $C_{10}$ aryl group that may contain a heteroatom" as used herein encompasses any aryl groups having 6 to 10 carbon atoms that are constituted by only a hydrocarbon, and any heteroaryl groups having 3 to 12 carbon atoms obtained by substituting at least one carbon atom included in the ring structure of the above-mentioned aryl groups with a heteroatom (e.g., a nitrogen atom, an oxygen atom, and a sulfur atom, and a combination thereof). Examples of the aryl groups having 6 to 10 carbon atoms include a phenyl group, a naphthyl group, an indenyl group, and an azulenyl group; and examples of any heteroaryl groups having 3 to 12 carbon atoms include a pyridyl group, a pyrrolyl group, a quinolyl group, an indolyl group, an imidazolyl group, a furyl group, and a thienyl group.

Examples of the term "aralkyl group with a $C_3$ to $C_{12}$ aryl moiety that may contain a heteroatom" as used herein include a benzyl group, a phenethyl group, a naphthylmethyl group, a 3-phenylpropyl group, a 2-phenylpropyl group, a 4-phenylbutyl group, a 2-phenylbutyl group, a pyridylmethyl group, an indolylmethyl group, a furylmethyl group, a thienylmethyl group, a pyrrolylmethyl group, a 2-pyridylethyl group, a 1-pyridylethyl group, and a 3-thienylpropyl group.

Examples of the term "acyl group" as used herein include aliphatic acyl groups and aromatic acyl groups. Specifically, examples of the aliphatic acyl groups include alkylcarbonyl groups such as a formyl group, an acetyl group, a propionyl group, a butyryl group, an isobutyryl group, a pentanoyl group, a pivaloyl group, a valeryl group, an isovaleryl group, an octanoyl group, a nonanoyl group, a decanoyl group, a 3-methylnonanoyl group, a 8-methylnonanoyl group, a 3-ethyloctanoyl group, a 3,7-dimethyloctanoyl group, an undecanoyl group, a dodecanoyl group, a tridecanoyl group, a tetradecanoyl group, a pentadecanoyl group, a hexadecanoyl group, a 1-methylpentadecanoyl group, a 14-methylpentadecanoyl group, a 13,13-dimethyltetradecanoyl group, a heptadecanoyl group, a 15-methylhexadecanoyl group, an octadecanoyl group, a 1-methylheptadecanoyl group, a nonadecanoyl group, an eicosanoyl group, and a heneicosanoyl group; carboxylated alkylcarbonyl groups such as a succinoyl group, a glutaroyl group, and an adipoyl group; halogeno lower-alkyl-carbonyl groups such as a chloroacetyl group, a dichloroacetyl group, a trichloroacetyl group, and a trifluoroacetyl group; lower-alkoxy-lower-alkyl-carbonyl groups such as a methoxyacetyl group; and unsaturated alkylcarbonyl groups such as an (E)-2-methyl-2-butenoyl group. Examples of the aromatic acyl groups include arylcarbonyl groups such as a benzoyl group, an α-naphthoyl group, and a β-naphthoyl group; halogeno arylcarbonyl groups such as a 2-bromobenzoyl group and a 4-chlorobenzoyl group; low-alkylated arylcarbonyl groups such as a 2,4,6-trimethylbenzoyl group and a 4-toluoyl group; low-alkoxylated arylcarbonyl groups such as a 4-anisoyl group: carboxylated arylcarbonyl groups such as a 2-carboxybenzoyl group, a 3-carboxybenzoyl group, and a 4-carboxybenzoyl group; nitrated arylcarbonyl groups such as a 4-nitrobenzoyl group and a 2-nitrobenzoyl group; low-alkoxycarbonylated arylcarbonyl groups such as a 2-(methoxycarbonyl)benzoyl group; and arylated arylcarbonyl groups such as a 4-phenylbenzoyl group. A formyl group, an acetyl group, a propionyl group, a butyryl group, an isobutyryl group, a pentanoyl group, a pivaloyl group, and a benzoyl group are favorable.

Examples of the term "silyl group" as used herein include tri-lower-alkyl-silyl groups such as a trimethylsilyl group, a triethylsilyl group, an isopropyldimethylsilyl group, a t-butyldimethylsilyl group, a methyldiisopropylsilyl group, a methyldi-t-butylsilyl group, and a triisopropylsilyl group; and tri-lower-alkyl-silyl groups that have undergone substitution by one or two aryl groups such as a diphenylmethylsilyl group, a butyldiphenylbutylsilyl group, a diphenylisopropylsilyl group, and a phenyldiisopropylsilyl group. A trimethylsilyl group, a triethylsilyl group, a triisopropylsilyl group, a t-butyldimethylsilyl group, and a t-butyldiphenylsilyl group are favorable, and a trimethylsilyl group is more favorable.

Examples of the term "halogen atom" as used herein include a fluorine atom, a chlorine atom, a bromine atom, and an iodine atom. A fluorine atom or a chlorine atom is favorable.

"Protecting groups" in the terms "amino group protecting group for nucleic acid synthesis", "hydroxy group protecting group for nucleic acid synthesis", "hydroxy group protected by a protecting group for nucleic acid synthesis", "phosphate group protected by a protecting group for nucleic acid synthesis", and "mercapto group protected by a protecting group for nucleic acid synthesis" as used herein are not particularly limited as long as they can stably protect an amino group, a hydroxy group, a phosphate group, or a mercapto group during nucleic acid synthesis. Specifically, the protecting groups are stable under an acidic or neutral condition and can be cleaved using chemical techniques such as hydrogenolysis, hydrolysis, electrolysis, and photolysis. Examples of such protecting groups include lower alkyl groups, lower alkenyl groups, acyl groups, tetrahydropyranyl or tetrahydrothiopyranyl groups, tetrahydrofuranyl or tetrahydrothiofuranyl groups, silyl groups, lower-alkoxymethyl groups, low-alkoxylated lower-alkoxy-methyl groups, halogeno lower-alkoxy-methyl groups, low-alkoxylated ethyl groups, halogenated ethyl groups, methyl groups that have undergone substitution by 1 to 3 aryl groups, "methyl groups that have undergone substitution by 1 to 3 aryl groups in which an aryl ring has undergone substitution by a lower alkyl group, lower alkoxy group, halogen atom, or cyano group", lower-alkoxy-carbonyl groups, "aryl groups that have undergone substitution by a halogen atom, lower alkoxy group, or nitro group", "lower-alkoxy-carbonyl groups that have undergone substitution by a halogen atom or tri-lower-alkyl-silyl group", alkenyloxycarbonyl groups, and "aralkyloxycarbonyl groups in which an aryl ring has optionally undergone substitution by a lower alkoxy group or nitro group".

More specific examples of the tetrahydropyranyl or tetrahydrothiopyranyl groups include a tetrahydropyran-2-yl group, a 3-bromotetrahydropyran-2-yl group, a 4-methoxytetrahydropyran-4-yl group, a tetrahydrothiopyran-4-yl group, and a 4-methoxytetrahydrothiopyran-4-yl group. Examples of the tetrahydrofuranyl or tetrahydrothiofuranyl groups include a tetrahydrofuran-2-yl group and a tetrahydrothiofuran-2-yl group. Examples of the lower-alkoxy-methyl groups include a methoxymethyl group, a 1,1-dimethyl-1-methoxymethyl group, an ethoxymethyl group, a propoxymethyl group, an isopropoxymethyl group, a butoxymethyl group, and a t-butoxymethyl group. An example of the low-alkoxylated lower-alkoxy-methyl groups is a 2-methoxyethoxymethyl group. Examples of the halogeno lower-alkoxy-methyl groups include a 2,2,2-trichloroethoxymethyl group and a bis(2-chloroethoxy)methyl group. Examples of the low-alkoxylated ethyl groups include a 1-ethoxyethyl group and a 1-(isopropoxy)ethyl group. An example of the halogenated ethyl groups is a 2,2,2-trichloroethyl group. Examples of the methyl groups that have undergone substitution by 1 to 3 aryl groups include a benzyl group, an α-naphthylmethyl group, a 6-naphthylmethyl group, a diphenylmethyl group, a triphenylmethyl group, an α-naphthyldiphenylmethyl group, and a 9-anthrylmethyl group. Examples of the "methyl groups that have undergone substitution by 1 to 3 aryl groups in which an aryl ring has undergone substitution by a lower alkyl group, lower alkoxy group, halogen atom, or cyano group" include a 4-methylbenzyl group, a 2,4,6-trimethylbenzyl group, a 3,4,5-trimethylbenzyl group, a 4-methoxybenzyl group, a 4-methoxyphenyldiphenylmethyl group, a 4,4'-dimethoxytriphenylmethyl group, a 2-nitrobenzyl group, a 4-nitrobenzyl group, a 4-chlorobenzyl group, a 4-bromobenzyl group, and a 4-cyanobenzyl group. Examples of the lower-alkoxy-carbonyl groups include a methoxycarbonyl group, an ethoxycarbonyl group, a t-butoxycarbonyl group, and an isobutoxycarbonyl group. Examples of the "aryl groups that have undergone substitution by a halogen atom, lower alkoxy group, or nitro group" include a 4-chlorophenyl group, a 2-fluorophenyl group, a 4-methoxyphenyl group, a 4-nitrophenyl group, and a 2,4-dinitrophenyl group. Examples of the "lower-alkoxycarbonyl groups that have undergone substitution by a halogen atom or tri-lower-alkyl-silyl group" include a 2,2,2-trichloroethoxycarbonyl group and 2-trimethylsilylethoxycarbonyl group. Examples of the alkenyloxycarbonyl groups include a vinyloxycarbonyl group and an aryloxycarbonyl group. Examples of the "aralkyloxycarbonyl groups in which an aryl ring has optionally undergone substitution by a lower alkoxy group or nitro group" include a benzyloxycarbonyl group, a 4-methoxybenzyloxycarbonyl group, a 3,4-dimethoxybenzyloxycarbonyl group, a 2-nitrobenzyloxycarbonyl group, and a 4-nitrobenzyloxycarbonyl group.

In an embodiment, examples of the "hydroxy group protecting group for nucleic acid synthesis" include aliphatic acyl groups, aromatic acyl groups, methyl groups that have undergone substitution by 1 to 3 aryl groups, "methyl groups that have undergone substitution by 1 to 3 aryl groups in which an aryl ring has undergone substitution by a lower alkyl, lower alkoxy, halogen, or cyano group", and silyl groups. Alternatively, in an embodiment, examples of the "hydroxy group protecting group for nucleic acid synthesis" include an acetyl group, a benzoyl group, a benzyl group, a p-methoxybenzyl group, a dimethoxytrityl group, a monomethoxytrityl group, a tert-butyldiphenylsilyl group, a tert-butyldimethylsilyl (TBDMS) group, a [(triisopropylsilyl)oxy]methyl (TOM) group, a [(2-nitrobenzyl)oxy]methyl (NBOM) group, a bis(acetoxyethoxy)methyl ether (ACE) group, a tetrahydro-4-methoxy-2H-pyran-2-yl (Mthp) group, a 1-(2-cyanoethoxy)ethyl (CEE) group, a 2-cyanoethoxymethyl (CEM) group, a tert-butyldithiomethyl (DTM) group, a 2-(4-tolylsulfonyl)ethoxymethyl (TEM) group, and a 4-(N-dichloroacetyl-N-methylamino)benzyloxymethyl (4-MABOM) group.

In an embodiment, examples of the protecting group used for the "hydroxy group protected by a protecting group for nucleic acid synthesis" include aliphatic acyl groups, aromatic acyl groups, "methyl groups that have undergone substitution by 1 to 3 aryl groups", "aryl groups that have undergone substitution by a halogen atom, lower alkoxy group, or nitro group", lower alkyl groups, and lower alkenyl groups. Alternatively, in an embodiment, examples of the protecting group used for the "hydroxy group protected by a protecting group for nucleic acid synthesis" include a benzoyl group, a benzyl group, a 2-chlorophenyl group, a 4-chlorophenyl group, and a 2-propenyl group.

In an embodiment, examples of the "amino group protecting group for nucleic acid synthesis" include acyl groups, and a benzoyl group is favorable.

In an embodiment, examples of the "protecting group" used for the "phosphate group protected by a protecting group for nucleic acid synthesis" include lower alkyl groups, lower alkyl groups that have undergone substitution by a cyano group, aralkyl groups, "aralkyl groups in which an aryl ring has undergone substitution by a nitro group or halogen atom", and "aryl groups that have undergone substitution by a lower alkyl group, halogen atom, or nitro group". Alternatively, in an embodiment, examples of the "protecting group" used for the "phosphate group protected by a protecting group for nucleic acid synthesis" include a 2-cyanoethyl group, a 2,2,2-trichloroethyl group, a benzyl group, a 2-chlorophenyl group, and a 4-chlorophenyl group.

In an embodiment, examples of the "protecting group" used for the "mercapto group protected by a protecting group for nucleic acid synthesis" include aliphatic acyl groups and aromatic acyl groups, and a benzoyl group is favorable.

In this specification, among groups represented by —P(R$^4$)R$^5$, wherein R$^4$ and R$^5$ each independently represent a hydroxy group, a hydroxy group protected by a protecting group for nucleic acid synthesis, a mercapto group, a mercapto group protected by a protecting group for nucleic acid synthesis, an amino group, a $C_1$ to $C_6$ alkoxy group, a $C_1$ to $C_6$ alkylthio group, a $C_1$ to $C_6$ cyanoalkoxy group, or a dialkylamino group having a $C_1$ to $C_6$ alkyl group, a group in which R$^4$ is OR$^{4a}$ and R$^5$ is NR$^{5a}$ is referred to as a "phosphoramidite group", where an example of R$^{4a}$ is a $C_1$ to $C_6$ cyanoalkoxy group, and an example of R$^{5a}$ is a $C_1$ to $C_6$ alkyl group. Favorable examples of the phosphoramidite group include a group represented by a formula —P(OC$_2$H$_4$CN)(N(iPr)$_2$) and a group represented by a formula —P(OCH$_3$)(N(iPr)$_2$). In these formulae, iPr represents an isopropyl group.

The terms "nucleoside" and "nucleoside analogue" as used herein refer to non-naturally occurring nucleosides of "nucleosides" in which a purine base or a pyrimidine base binds to sugar, as well as those in which a heteroaromatic ring or an aromatic hydrocarbon ring other than purine and pyrimidine that can serve as a substitute for a purine or pyrimidine base binds to sugar.

The terms "artificial oligonucleotide" and "oligonucleotide analogue" as used herein refer to non-naturally occurring derivatives of "oligonucleotides" in which, for example, two to fifty of the same or different "nucleosides" or "nucleoside analogues" are bound via phosphodiester bonds. Favorable examples of such analogues include sugar derivatives with sugar moieties modified; thioated derivatives with phosphate diester moieties thioated; esters with terminal phosphate moieties esterified; and amides in which amino groups on purine bases are amidated. The sugar derivatives with sugar moieties modified are more favorable.

The term "salt thereof" as used herein refers to a salt of a compound represented by the formula (I) or (II) of the present invention. Examples of such salt include metal salts including alkali metal salts such as sodium salts, potassium salts, and lithium salts, alkali earth metal salts such as calcium salts and magnesium salts, and aluminum salts, iron salts, zinc salts, copper salts, nickel salts, and cobalt salts; amine salts including inorganic salts such as ammonium salts, and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris(hydroxymethyl)aminomethane salts; inorganic acid salts including halide hydroacid salts such as hydrofluoric acid salts, hydrochloric acid salt, hydrobromic acid salts, and hydroiodic acid salts, nitrates, perchlorates, sulfates, and phosphates; organic acid salts including lower-alkanesulfonates such as methanesulfonates, trifluoromethanesulfonates, and ethanesulfonates, arylsulfonates such as benzenesulfonates and p-toluenesulfonates, acetates, malates, fumarates, succinates, citrates, tartrates, oxalates and maleates; and amino acid salts such as glycine salts, lysine salts, arginine salts, ornithine salts, glutamates, and aspartates.

The term "pharmacologically acceptable salt thereof" refers to a salt of an oligonucleotide analogue containing at least one nucleoside structure represented by the formula (II) of the present invention. Examples of such salt include metal salts including alkali metal salts such as sodium salts, potassium salts, and lithium salts, alkali earth metal salts such as calcium salts and magnesium salts, and aluminum salts, iron salts, zinc salts, copper salts, nickel salts, and cobalt salts; amine salts including inorganic salts such as ammonium salts, and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris (hydroxymethyl)aminomethane salts; inorganic acid salts including halide hydroacid salts such as hydrofluoric acid salts, hydrochloric acid salt, hydrobromic acid salts, and hydroioclic acid salts, nitrates, perchlorates, sulfates, and phosphates; organic acid salts including lower-alkanesulfonates such as methanesulfonates, trifluoromethanesulfonates, and ethanesulfonates, arylsulfonates such as benzenesulfonates and p-toluenesulfonates, acetates, malates, fumarates, succinates, citrates, tartrates, oxalates and maleates; and amino acid salts such as glycine salts, lysine salts, arginine salts, ornithine salts, glutamates, and aspartates.

Hereinafter, the present invention will be described in detail.

The 5'-modified nucleoside of the present invention is a compound represented by a formula (I) below or a salt thereof:

[Chemical Formula 8]

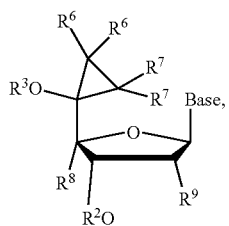

(I)

wherein Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms;

$R^2$ and $R^3$ each independently represent a hydrogen atom, a hydroxy group protecting group for nucleic acid synthesis, a $C_1$ to $C_7$ alkyl group that may be branched or form a ring, a $C_2$ to $C_7$ alkenyl group that may be branched or form a ring, a $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —P($R^4$)$R^5$, wherein $R^4$ and $R^5$ each independently represent a hydroxy group, a hydroxy group protected by a protecting group for nucleic acid synthesis, a mercapto group, a mercapto group protected by a protecting group for nucleic acid synthesis, an amino group, a $C_1$ to $C_6$ alkoxy group, a $C_1$ to $C_6$ alkylthio group, a $C_1$ to $C_6$ cyanoalkoxy group, or a dialkylamino group having a $C_1$ to $C_6$ alkyl group;

$R^6$ and $R^7$ are each independently a hydrogen atom, a halogen atom, or a methyl group; and $R^8$ is a hydrogen atom, and $R^9$ is a hydrogen atom or a halogen atom; a $C_1$ to $C_6$ linear alkoxy group that may be substituted with a $C_1$ to $C_6$ linear alkoxy group; or —O$R^{10}$, wherein $R^{10}$ is a hydrogen atom or a hydroxy group protecting group for nucleic acid synthesis, or $R^8$ and $R^9$ together represent a divalent group represented by a formula below:

[Chemical Formula 9]

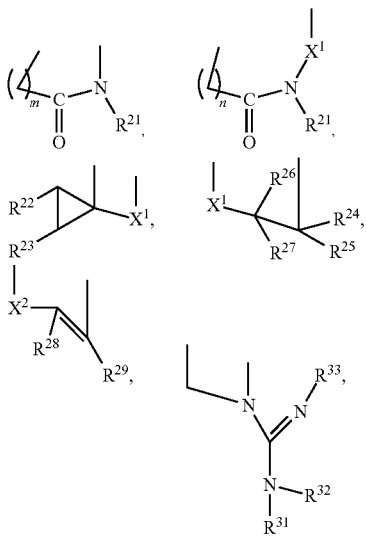

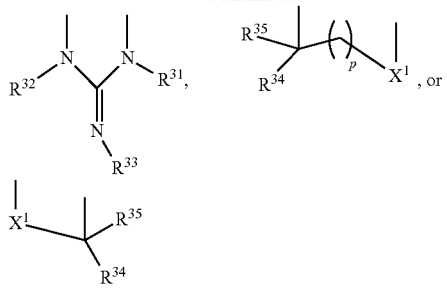

wherein $R^{21}$ is a hydrogen atom, a $C_1$ to $C_6$ alkyl group that may be branched or form a ring, a $C_2$ to $C_6$ alkenyl group that may be branched or form a ring, a $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, or an amino group protecting group for nucleic acid synthesis;

$R^{22}$ and $R^{23}$ are each independently a hydrogen atom, $C_1$ to $C_6$ alkyl group that may be substituted with a $C_3$ to $C_{12}$ aryl group that may contain a heteroatom, and that may be branched or form a ring, or an aralkyl group with a $C_3$ to $C_{12}$ aryl moiety that may contain a heteroatom, or $R^{22}$ and $R^{23}$ together represent —(CH$_2$)$_q$—, wherein q is an integer from 2 to 5;

$R^{24}$ and $R^{25}$ are each independently a group selected from the group consisting of a hydrogen atom, a hydroxy group, a $C_1$ to $C_6$ alkyl group that may be branched or form a ring, a $C_1$ to $C_6$ alkoxy group that may be branched or form a ring, an amino group, and an amino group protected by a protecting group for nucleic acid synthesis, or $R^{24}$ and $R^{25}$ together represent =C($R^{36}$)$R^{37}$, wherein $R^{36}$ and $R^{37}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group;

$R^{26}$ and $R^{27}$ are each independently a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

$R^{28}$ is a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

$R^{29}$ is a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

$R^{31}$, $R^{32}$, and $R^{33}$ are each independently a hydrogen atom, a $C_1$ to $C_6$ alkyl group that may be branched or form a ring, or an amino group protecting group for nucleic acid synthesis;

$R^{34}$ and $R^{35}$ are each independently a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

m is an integer from 0 to 2;

n is an integer of 0 or 1;

p is an integer of 0 or 1;

$X^1$ is an oxygen atom, a sulfur atom, or an amino group; and $X^2$ is an oxygen atom or a sulfur atom.

In the formula (I) above, "Base" is, for example, a purine base (i.e., purin-9-yl group) or a pyrimidine base (i.e., 2-oxo-1,2-dihydropyrimidin-1-yl group). These bases may have any one or more substituents selected from the α group consisting of a hydroxy group, a $C_1$ to $C_6$ linear alkyl group, a $C_1$ to $C_6$ linear alkoxy group, a mercapto group, a $C_1$ to $C_6$ linear alkylthio group, an amino group, a $C_1$ to $C_6$ linear alkylamino group, and halogen atoms.

Specific examples of the "Base" above include an adeninyl group, a guaninyl group, a cytosinyl group, an uracinyl group and a thyminyl group, a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimiclin-1-yl group, a 4-amino-2-oxo-5-fluoro-1,2-dihydropyrimiclin-1-yl group, a 4-amino-2-oxo-5-chloro-1,2-dihydropyrimidin-1-yl group, a 2-oxo-4-methoxy-1,2-dihydropyrimiclin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimiclin-1-yl group, and a 4-amino-5-methyl-2-oxo-1,2-dihydropyrimiclin-1-yl group.

Alternatively, from the viewpoint of introduction into a nucleic acid drug, as the "Base", groups represented by structural formulae below:

[Chemical Formula 10]

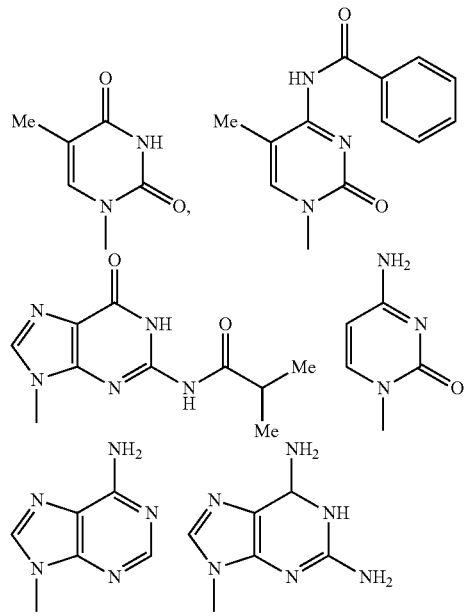

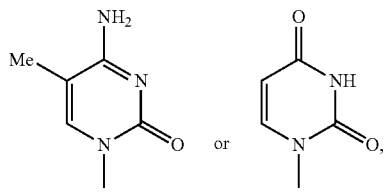

as well as a 2-oxo-4-hydroxy-5-methyl-1,2-dihydropyrimidin-1-yl group, a 2-oxo-4-amino-1,2-dihydropyrimiclin-1-yl group, a 6-aminopurin-9-yl group, a 2-amino-6-hydroxypurin-9-yl group, a 4-amino-5-methyl-2-oxo-1,2-dihydropyrimiclin-1-yl group, and a 2-oxo-4-hydroxy-1,2-dihydropyrimidin-1-yl group are favorable. It is preferable that a hydroxy group and an amino group included in the above-mentioned groups serving as the "Base" are protected by a protecting group during oligonucleotide synthesis.

In the 5'-modified nucleoside of the present invention, two identical atoms or groups $R^6$ are bound to one carbon atom included in the cyclopropane moiety at the 5' position of the formula (I), and two identical atoms or groups $R^7$ are bound to another carbon atom. With this structure, the nucleoside of the present invention cannot have a diastereomer structure at the 5' position, and therefore, compared with conventional artificial nucleic acids obtained by introducing a substituent into the 5' position, the separation of diastereomers during synthesis is no longer necessary.

From the viewpoint of combinations of such $R^6$ and $R^7$, examples of the formula (I) above include:

[Chemical Formula 11]

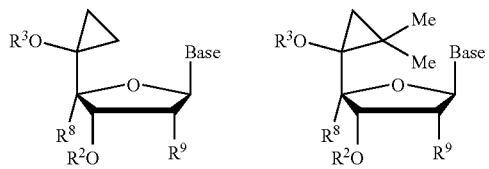

wherein Base, $R^2$, $R^3$, $R^8$, and $R^9$ are as defined for the formula (I) above. In the present invention, it is preferable that $R^6$ and $R^7$ in the formula (I) above are both hydrogen atoms.

Furthermore, the 5'-modified nucleoside of the present invention may have a configuration in which, at the 2' position and the 4' position of the formula (I), as shown below:

[Chemical Formula 12]

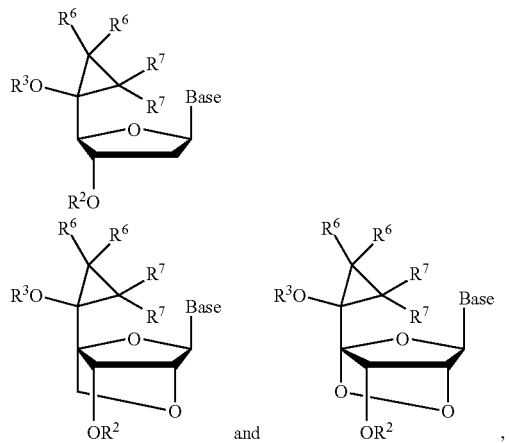

wherein Base, $R^2$, $R^3$, $R^6$, and $R^7$ are as defined for the formula (I) above, $R^8$ and $R^9$ has a cross-link structure together, or $R^8$ and $R^9$ are both hydrogen atoms. In an embodiment of the present invention, it is preferable that $R^8$ and $R^9$ in the formula (I) above are both hydrogen atoms.

The 5'-modified nucleoside of the present invention improves the nuclease-resistant ability of an oligonucleotide, which will be described later, because the cyclopropane moiety is introduced into the 5' position of the formula (I). Moreover, a distortion of the ring of such a cyclopropane group has a direct effect on the conformation of the sugar moiety. Thus, the 5'-modified nucleoside of the present invention can further improve the binding affinity of the resultant oligonucleotide for ssRNA due to this effect.

In the present invention, an oligonucleotide can be easily produced by using such 5'-mollified nucleoside represented by the formula (I) and using, for example, an amidite method that is well known in the art, or triphosphorylation such as that described in M. Kuwahara et al., Nucleic Acids Res., 2008, Vol. 36, No. 13, pp. 4257-4265.

The oligonucleotide containing at least one nucleoside structure or a pharmacologically acceptable salt thereof (hereinafter, these may be collectively referred to as "oligonucleotide of the present invention") is represented by a formula (II) below:

[Chemical Formula 13]

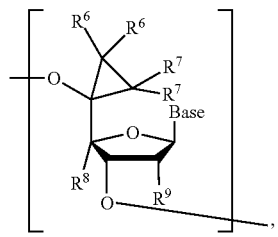

(II)

wherein Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms;

$R^6$ and $R^7$ are each independently a hydrogen atom, a halogen atom, or a methyl group; and $R^8$ is a hydrogen atom, and $R^9$ is a hydrogen atom, a halogen atom, or a $C_1$ to $C_6$ linear alkoxy group that may be substituted with a $C_1$ to $C_6$ linear alkoxy group, or $R^8$ and $R^9$ together represent a divalent group represented by a formula below (CR01) to (CR11);

[Chemical Formula 14]

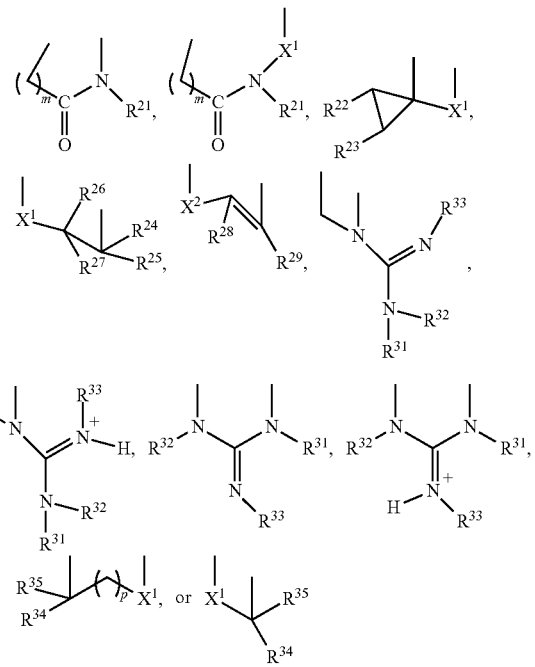

wherein $R^{21}$ is a hydrogen atom, a $C_1$ to $C_6$ alkyl group that may be branched or form a ring, a $C_2$ to $C_6$ alkenyl group that may be branched or form a ring, a $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, or an amino group protecting group for nucleic acid synthesis;

$R^{22}$ and $R^{23}$ are each independently a hydrogen atom, a $C_1$ to $C_6$ alkyl group that may be substituted with a $C_3$ to $C_{12}$ aryl group that may contain a heteroatom, and that may be branched or form a ring, or an aralkyl group with a $C_3$ to $C_{12}$ aryl moiety that may contain a heteroatom, or $R^{22}$ and $R^{23}$ together represent —$(CH_2)_q$—, wherein q is an integer from 2 to 5;

$R^{24}$ and $R^{25}$ are each independently a group selected from the group consisting of a hydrogen atom, a hydroxy group, a $C_1$ to $C_6$ alkyl group that may be branched or form a ring, a $C_1$ to $C_6$ alkoxy group that may be branched or form a ring, an amino group, an amino group, and an amino group protected by a protecting group for nucleic acid synthesis, or $R^{24}$ and $R^{25}$ together represent $=C(R^{36})R^{37}$, wherein $R^{36}$ and $R^{37}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group;

$R^{26}$ and $R^{27}$ are each independently a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

$R^{28}$ is a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

$R^{29}$ is a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

$R^{31}$, $R^{32}$, and $R^{33}$ are each independently a hydrogen atom, a $C_1$ to $C_6$ alkyl group that may be branched or form a ring, or an amino group protecting group for nucleic acid synthesis;

$R^{34}$ and $R^{35}$ are each independently a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

m is an integer from 0 to 2;
n is an integer of 0 or 1;
p is an integer of 0 or 1;
$X^1$ is an oxygen atom, a sulfur atom, or an amino group; and
$X^2$ is an oxygen atom or a sulfur atom.

Note that, in the present invention, among the cross-link structures represented by the formulae (CR01) to (CR11) above, the structures represented by the formulae (CR07) and (CR09) are kept electrically neutral by any anions (e.g., hydroxide ions, phosphoric ions, and chloride ions) that are present around the cross-link structure.

Here, from the viewpoint of combinations of $R^6$ and $R^7$, examples of the nucleoside structure represented by the formula (II) and contained in the oligonucleotide of the present invention include:

[Chemical Formula 15]

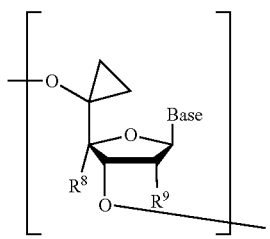

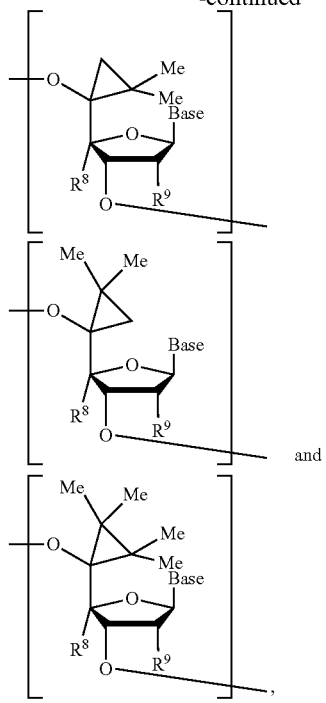

wherein Base, $R^8$ and $R^9$ are as defined for the formula (II) above. In the present invention, it is preferable that $R^6$ and $R^7$ in the formula (II) above are both hydrogen atoms.

Furthermore, from the viewpoint of combinations of $R^8$ and $R^9$, examples of the nucleoside structure represented by the formula (II) and contained in the oligonucleotide of the present invention include:

[Chemical Formula 16]

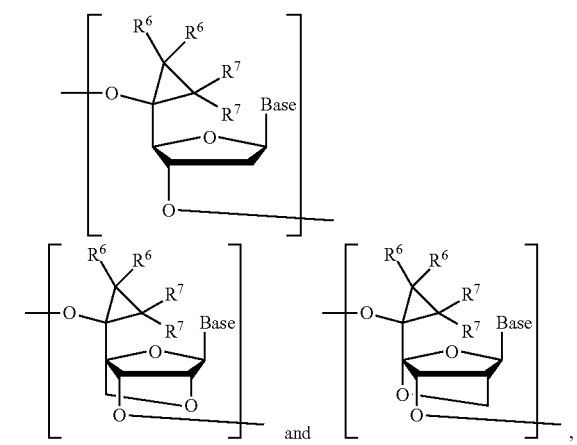

wherein Base, $R^6$ and $R^7$ are as defined for the formula (II) above. In an embodiment of the present invention, $R^6$ and $R^7$ in the formula (II) above are both hydrogen atoms.

The oligonucleotide of the present invention has at least one nucleoside structure described above at any position. There is no particular limitation on the positions and number of the nucleoside structures, and the oligonucleotide can be designed as appropriate depending on the purpose.

An oligonucleotide (antisense molecule) containing such a nucleoside structure has significantly improved nuclease-resistant ability when compared with the cases where conventional 2',4'-BNA/LNA is used, and also has good binding affinity for ssRNA comparable to that of known 2',4'-BNA/LNA. Furthermore, this oligonucleotide is also capable of reducing hematotoxicity without impairing the antisense activity.

With all these facts, the oligonucleotide of the present invention synthesized using the 5'-modified nucleoside of the present invention is expected to be useful as a pharmaceutical agent (antisense molecule), such as antitumor agents and antiviral drugs, inhibiting or restoring the functions of specific genes to treat a disease. An example of such pharmaceutical agent that is expected to be useful as described above is a therapeutic drug for muscular dystrophy.

In particular, for antisense therapies, the binding affinity for complementary sense strand RNAs and the resistance to in vivo DNA-degrading enzymes are both required. Generally, a nucleic acid in the form of a single strand is known to constantly have a structural fluctuation of a sugar moiety between the form close to a sugar moiety in a double-stranded DNA and the form close to a sugar moiety in a double-stranded DNA-RNA or a double-stranded RNA. When a single-stranded nucleic acid forms a double strand with a complementary RNA strand, its structure of the sugar moiety is fixed. Therefore, the 5'-modified nucleoside of the invention readily forms a double strand with an intended RNA strand, which may be then maintained stably, because the sugar moiety has already been kept to the structure capable of forming a double strand. Furthermore, it is also known that a double-stranded nucleic acid is stabilized with hydrated water with a chain-like structure referred to as "network of water molecules".

Additives typically used in the art of pharmaceuticals such as excipients, binders, preservatives, oxidation stabilizers, disintegrants, lubricants, and flavoring substances can be added to the oligonucleotide of the present invention to prepare parenteral formulations or liposomal formulations. Also, for example, topical formulations such as liquids, creams, and ointments may be prepared by adding pharmaceutical carriers typically used in the art.

EXAMPLES

Hereinafter, the present invention will be described in greater detail using examples. However, the present invention is not limited to the examples below.

Example 1

Synthesis of 5'-Modified Nucleoside (1)

[Chemical Formula 17]

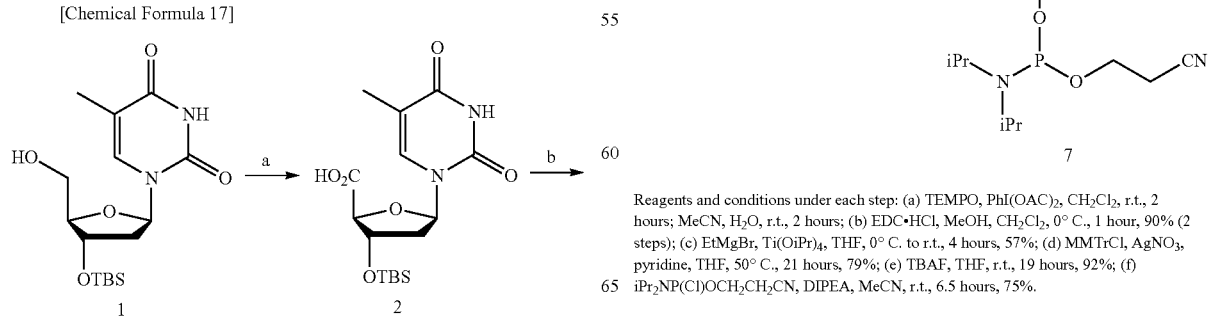

Reagents and conditions under each step: (a) TEMPO, PhI(OAC)$_2$, CH$_2$Cl$_2$, r.t., 2 hours; MeCN, H$_2$O, r.t., 2 hours; (b) EDC·HCl, MeOH, CH$_2$Cl$_2$, 0° C., 1 hour, 90% (2 steps); (c) EtMgBr, Ti(OiPr)$_4$, THF, 0° C. to r.t., 4 hours, 57%; (d) MMTrCl, AgNO$_3$, pyridine, THF, 50° C., 21 hours, 79%; (e) TBAF, THF, r.t., 19 hours, 92%; (f) iPr$_2$NP(Cl)OCH$_2$CH$_2$CN, DIPEA, MeCN, r.t., 6.5 hours, 75%.

(1-1) Synthesis of Compound 2

[Chemical Formula 18]

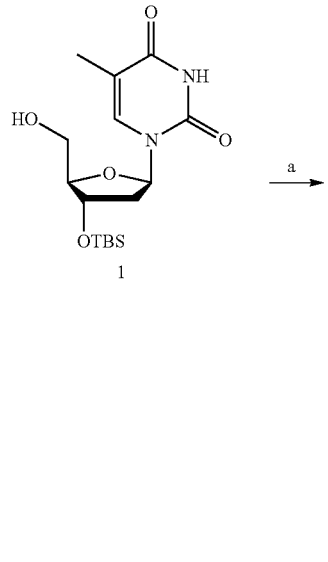

To a dichloromethane solution (31 mL) of a compound 1 (1.50 g, 4.20 mmol), the compound 1 being prepared using a method described in Caruthers et al., Tetrahedron Lett., 1996, Vol. 37, No. 35, pp. 6239-6242, were added sequentially at 0° C. iodobenzene diacetate (PhI(OAc)$_2$; 2.98 g, 9.24 mmol) and 2,2,6,6-tetramethylpiperidine 1-oxyl free radical (TEMPO; 151 mg, 0.96 mmol). The mixture was stirred at room temperature for 2 hours, and then, acetonitrile/water (=1:1 (volume ratio), 230 μL) was added to the mixture, followed by stirring at room temperature for another 2 hours. After completion of the reaction, an excess of methanol was added to the mixture, and the mixture was stirred at room temperature for 10 minutes, followed by distillation of the solvent under reduced pressure and azeotroped with toluene, to afford a compound 2 (4.20 mmol or less, crude product) as a white solid.

The compound 2 was immediately used for the next reaction without purification.

(1-2) Synthesis of Compound 3

[Chemical Formula 19]

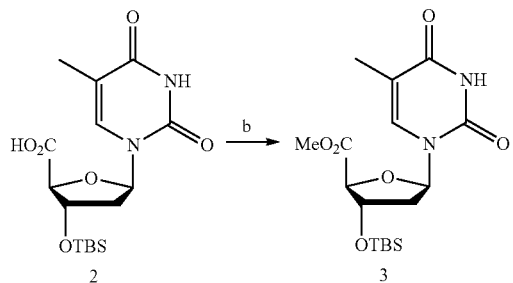

To a dichloromethane solution (42 mL) of the compound 2 (4.20 mmol or less, crude product) obtained above were added sequentially methanol (1.70 mL, 42.0 mmol) and 1-(3-dimethylaminopropyl)-3-ethylcarbodiimide hydrochloride (EDC·HCl; 966 mg, 5.04 mmol), and the mixture was stirred at 0° C. for an hour. After completion of the reaction, water was added, followed by extraction with ethyl acetate. The organic layer was washed with water and saturated saline and then dried over anhydrous sodium sulfate, and the solvent was distilled away under reduced pressure. The resultant residue was purified by silica-gel column chromatography (SiO$_2$, ethyl acetate/hexane=37% to 58%) to afford a compound 3 (1.44 g, yield: 90%, 2 steps) as a white solid.

Table 1 shows data on the properties of the obtained compound 3.

TABLE 1

| Physical property data of the obtained compound 3 |
| --- |
| $^1$H NMR (300 MHz, CDCl$_3$) δ 0.12 (s, 3H), 0.13 (s, 3H), 0.91 (s, 9H), 1.90-1.98 (m, 1H), 1.98 (s, 3H), 2.32 (dd, J = 4.8, 13.1 Hz, 1H), 3.82 (s, 3H), 4.46 (s, 1H), 4.52 (d, J = 4.1 Hz, 1H), 6.53 (dd, J = 5.2, 8.9 Hz, 1H), 8.09 (s, 1H), 8.67 (bs, 1H); $^{13}$C NMR (76 MHz, CDCl$_3$) δ −4.9, 12.8, 18.1, 25.7, 39.8, 52.7, 75.8, 85.3, 86.7, 111.4, 136.3, 150.7, 164.2, 171.9; IR (KBr): 3168, 3040, 2941, 2859, 1747, 1695, 1468, 1269, 1213, 1085, 836 cm$^{-1}$. |

(1-3) Synthesis of Compound 4

[Chemical Formula 20]

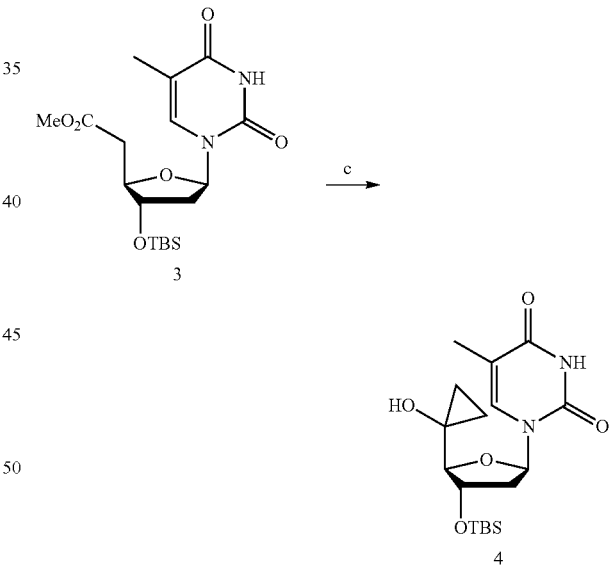

Under nitrogen stream, to an anhydrous tetrahydrofuran solution (12 mL) of the compound 3 (455 mg, 1.18 mmol) obtained above and titanium tetraisopropoxide (Ti(OiPr)$_4$; 350 μL, 1.18 mmol) was added dropwise at 0° C. over 2 hours a tetrahydrofuran solution (6.0 mL, 6.0 mmol) of 1.0 M ethyl magnesium bromide (EtMgBr). After the dropwise addition, the reaction solution was warmed to room temperature and stirred for another 2 hours. After completion of the reaction, Celite filtration was performed after a saturated aqueous solution of ammonium chloride was added thereto, and the filtrate was extracted with ethyl acetate. The organic layer was washed with water and saturated saline and then dried over anhydrous sodium sulfate, and the solvent was distilled away under reduced pressure. The resultant residue was purified by silica-gel column chromatography ($SiO_2$, ethyl acetate/hexane=50% to 71%) to afford a compound 4 (257 mg, yield: 57%) as a white solid.

Table 2 shows data on the properties of the obtained compound 4.

TABLE 2

Physical property data of the obtained compound 4

$^1$H NMR (300 MHz, $CDCl_3$) δ 0.10 (s, 6H), 0.64-0.69 (m, 2H), 0.85-0.91 (m, 2H), 0.90 (s, 9H), 1.92 (d, J = 1.4 Hz, 3H), 2.16 (ddd, J = 3.4, 6.5, 13.4 Hz, 1H), 2.61 (ddd, J = 6.5, 7.6, 13.4 Hz, 1H), 3.31 (d, J = 3.4 Hz, 1H), 3.64 (s, 1H), 4.72 (ddd, J = 3.4, 3.4, 6.5 Hz, 1H), 6.03 (dd, J = 6.5, 7.2 Hz, 1H), 7.26 (s, 1H), 8.30 (bs, 1H); $^{13}$C NMR (76 MHz, $CDCl_3$) δ −4.7, −4.6, 10.6, 12.6, 13.1, 18.0, 25.8, 39.8, 54.5, 72.6, 87.8, 93.5, 111.2, 138.0, 150.4, 163.8; IR (KBr): 3414, 3010, 2949, 1681, 1472, 1266, 1061, 840, 758 $cm^{-1}$; HRMS (MALDI) Calculated for $C_{18}H_{30}N_2O_5NaSi$ [M + Na]$^+$: 405.1816, Found: 405.1820.

(1-4) Synthesis of Compound 5

[Chemical Formula 21]

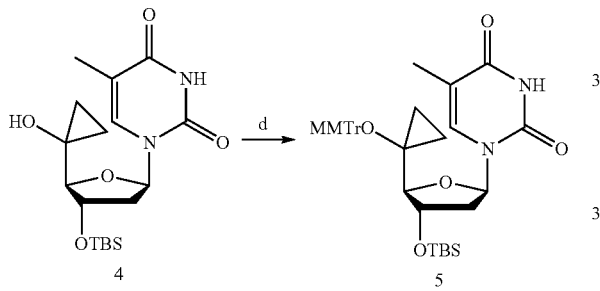

Under nitrogen stream, to an anhydrous pyridine/tetrahydrofuran mixed solution (=1:4 (volume ratio), 520 mL) of the compound 4 (5.00 g, 13.1 mmol) obtained above were added sequentially 4-methoxytrityl chloride (MMTrCl; 17.8 g, 57.6 mmol) and silver nitrate (9.65 g, 56.8 mmol), and the mixture was stirred at 50° C. for 21 hours. After completion of the reaction, Celite filtration was performed after a saturated aqueous solution of sodium hydrogen carbonate was added thereto, and the filtrate was extracted with ethyl acetate. The organic layer was washed twice with a saturated aqueous solution of sodium thiosulfate and once with a water/saturated saline mixed solution (=1:1 (volume ratio)) and then dried over anhydrous sodium sulfate, followed by distillation of the solvent under reduced pressure and azeotroped with toluene. The resultant residue was purified by silica-gel column chromatography ($SiO_2$, containing 1% triethylamine, ethyl acetate/hexane=24% to 45%) to afford a compound 5 (6.78 g, yield: 79%) as a yellow solid.

Table 3 shows data on the properties of the obtained compound 5.

TABLE 3

Physical property data of the obtained compound 5

$^1$H NMR (300 MHz, $CDCl_3$) δ −0.02 (s, 3H), 0.03 (s, 3H), 0.40-0.47 (m, 1H), 0.50-0.57 (m, 1H), 0.82 (s, 9H), 0.83-1.00 (m, 2H), 1.79-1.92 (m, 1H), 1.86 (d, J = 0.9 Hz, 3H), 2.20 (ddd, J = 13.4, 2.6, 1.3 Hz, 1H), 2.90

TABLE 3-continued

Physical property data of the obtained compound 5

(d, J = 2.3 Hz, 1H), 3.80 (s, 3H), 4.09-4.12 (m, 1H), 5.93 (dd, J = 8.3, 5.5 Hz, 1H), 6.79-6.85 (m, 2H), 7.16-7.47 (m, 13H), 8.56 (bs, 1H); $^{13}$C NMR (76 MHz, $CDCl_3$) δ −4.7, −4.2, 9.6, 10.2, 12.8, 17.9, 25.8, 41.5, 55.3, 58.8, 72.8, 85.0, 87.7, 87.8, 110.6, 113.0, 127.2, 127.8, 128.8, 128.8, 131.2, 135.7, 136.3, 145.9, 145.9, 158.9.

(1-5) Synthesis of Compound 6

[Chemical Formula 22]

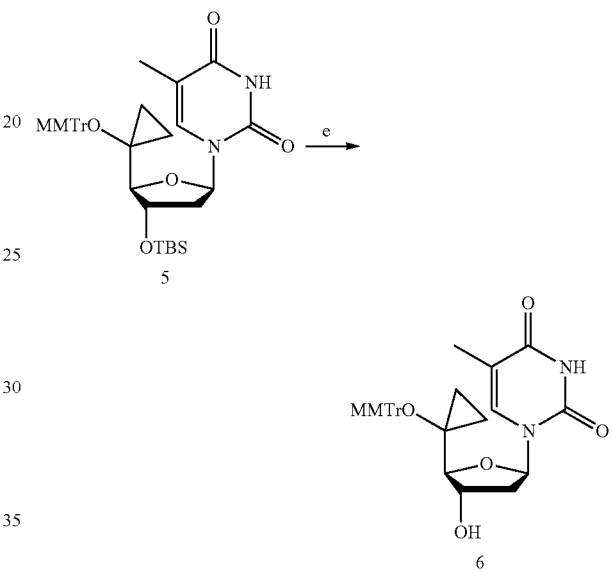

To a tetrahydrofuran solution (81 mL) of the compound 5 (2.65 g, 4.05 mmol) obtained above was added at 0° C. a tetrahydrofuran solution (4.50 mL, 4.50 mmol) of 1.0 M tetrabutylammonium fluoride (TBAF), and the mixture was stirred at room temperature for 19 hours. After completion of the reaction, the reaction liquid was distilled away under reduced pressure, and water was added, followed by extraction with ethyl acetate. The organic layer was washed with saturated saline and then dried over anhydrous sodium sulfate, and the solvent was distilled away under reduced pressure. The resultant residue was purified by silica-gel column chromatography ($SiO_2$, containing 1% triethylamine, ethyl acetate/hexane=80% to 100%) to afford a compound 6 (2.02 g, yield: 92%) as a white solid.

Table 4 shows data on the properties of the obtained compound 6.

TABLE 4

Physical property data of the obtained compound 6

$^1$H NMR (300 MHz, $CDCl_3$) δ 0.53-0.57 (m, 2H), 0.94-0.98 (m, 2H), 1.75 (d, J = 2.3 Hz, 1H), 1.90 (d, J = 0.9 Hz, 3H), 2.03 (ddd, J = 7.3, 6.9, 14.2 Hz, 1H), 2.17 (ddd, J = 13.8, 6.9, 4.6 Hz, 1H), 2.67 (d, J = 4.6 Hz, 1H), 3.82 (s, 3H), 4.44-4.50 (m, 1H), 5.87 (dd, J = 6.9, 6.9 Hz, 1H), 6.83-6.86 (m, 2H), 6.94 (d, J = 1.4 Hz, 1H), 7.25-7.46 (m, 12H), 8.14 (bs, 1H); $^{13}$C NMR (76 MHz, $CDCl_3$) δ 9.1, 10.2, 12.8, 39.5, 55.3, 59.9, 73.0, 83.5, 83.9, 87.7, 111.3, 113.1, 127.3, 127.9, 127.9, 128.5, 128.6, 131.0, 135.3, 136.1, 145.7, 145.8, 150.5, 158.9, 163.9.

(1-6) Synthesis of Compound 7

[Chemical Formula 23]

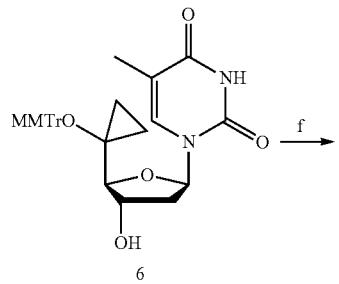

6

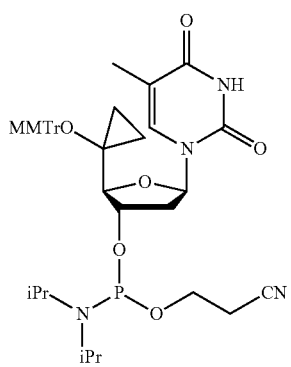

7

Under nitrogen stream, to an anhydrous acetonitrile solution (36 mL) of the compound 6 (1.92 g, 3.56 mmol) obtained above were added sequentially at 0° C. N,N-diisopropylethylamine (DIPEA; 1.85 mL, 10.8 mmol) and 2-cyanoethyl-N,N-diisopropyl phosphorochloridate (iPr$_2$NP(Cl)OCH$_2$CH$_2$CN; 1.20 mL, 5.34 mmol), and the mixture was stirred at room temperature for 3 hours. After completion of the reaction, the solvent was distilled away under reduced pressure, and the resultant residue was purified by silica-gel column chromatography (SiO$_2$, containing 1% triethylamine, ethyl acetate/hexane=39% to 60%) to afford a compound 7 (1.93 g, yield: 73%) as a white solid.

Table 5 shows data on the properties of the obtained compound 7.

TABLE 5

Physical property data of the obtained compound 7

$^1$H NMR (300 MHz, CDCl$_3$) δ 0.45-0.62 (m, 2H), 0.92-1.03 (m, 2H), 1.08 (d, J = 6.9 Hz, 3H), 1.14 (d, J = 6.9 Hz, 6H), 1.18 (d, J = 6.4 Hz, 3H), 1.82-1.96 (m, 1H), 1.87 (d, J = 0.9 Hz, 3H), 2.40-2.50 (m, 2.1H), 2.60-2.65 (m, 0.9H), 2.95 (d, J = 1.8 Hz, 0.3H), 3.05 (s, 0.7H), 3.49-3.69 (m, 4H), 3.80 (s, 0.9H), 3.81 (s, 2.1H), 4.39-4.48 (m, 1H), 5.89-5.94 (m, 1H), 6.78-6.84 (m, 2H), 7.13-7.46 (m, 13H), 8.04 (bs, 1H); $^{31}$P NMR (121.7 MHz, CDCl$_3$) δ 148.0, 149.5.

Example 2

Synthesis of 5'-Modified Nucleoside (2)

[Chemical Formula 24]

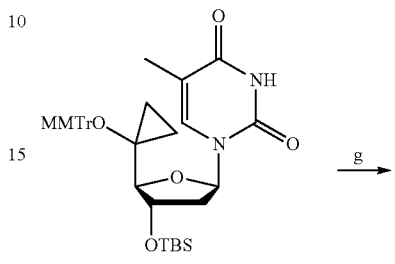

5

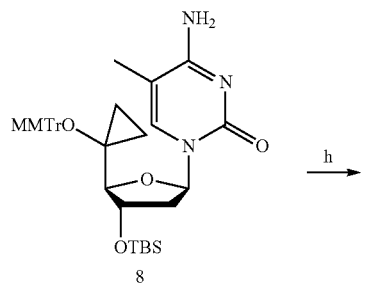

8

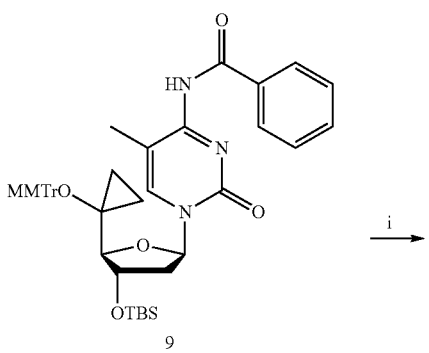

9

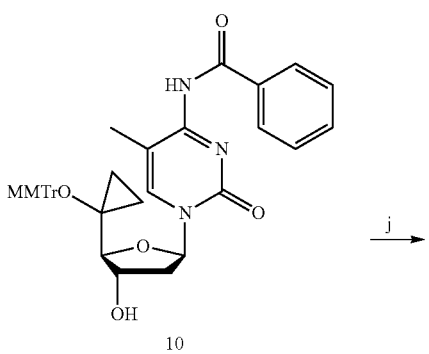

10

-continued

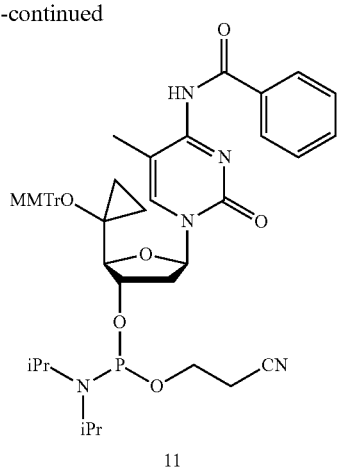

11

Reagents and conditions under each step:
(g) 1,2,4-triazole, POCl₃, TEA, MeCN, r.t., 2 hours;
saturated NH₃ aq., 1,4-dioxane, r.t., 5 hours, 92%;
(h) BzCl, pyridine, 0° C., 1.5 hours, 81%;
(i) TBAF, THF, r.t., 24 hours, 96%;
(j) iPr₂NP(Cl)OCH₂CH₂CN, DIPEA, MeCN, r.t., 3 hours, 69%.

(2-1) Synthesis of Compound 8

[Chemical Formula 25]

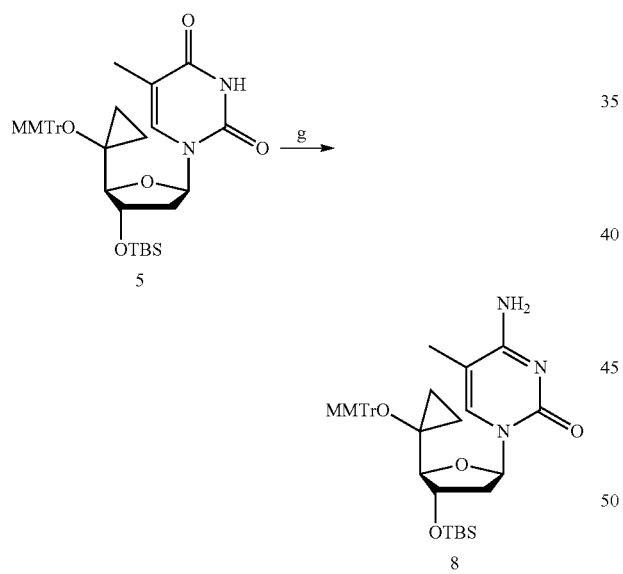

Under nitrogen stream, to an anhydrous acetonitrile solution (55 mL) of the compound 5 (3.59 g, 5.48 mmol) obtained above were added sequentially at 0° C. triethylamine (TEA; 11.4 mL, 82.2 mmol), 1,2,4-triazole (5.72 g, 82.8 mmol), and phosphoryl chloride (POCl₃; 1.50 mL, 16.4 mmol), and the mixture was stirred at room temperature for 2 hours. Subsequently, 1,4-dioxane (55 mL) and 28% aqueous ammonia (16.4 mL) were added, and the mixture was stirred at room temperature for 5 hours. After completion of the reaction, the reaction liquid was distilled away under reduced pressure, and a water/saturated saline mixed solution (=1:1 (volume ratio)) was added, followed by extraction with ethyl acetate. The organic layer was washed with saturated saline and then dried over anhydrous sodium sulfate, and the solvent was distilled away under reduced pressure. The resultant residue was purified by silica-gel column chromatography (SiO₂, containing 1% triethylamine, methanol/chloroform=0% to 3%) to afford a compound 8 (3.31 g, yield: 92%) as a light yellow solid.

Table 6 shows data on the properties of the obtained compound 8.

TABLE 6

Physical property data of the obtained compound 8

¹H NMR (300 MHz, CDCl₃) δ −0.04 (s, 3H), 0.01 (s, 3H), 0.41-0.56 (m, 2H), 0.76-0.99 (m, 2H), 0.80 (s, 9H), 1.75-1.82 (m, 1H), 1.84 (s, 3H), 2.38 (ddd, J = 2.3, 5.5, 13.3 Hz, 1H), 2.97 (d, J = 2.8 Hz, 1H), 3.79 (s, 3H), 4.03 (ddd, J = 2.8, 2.8, 5.5 Hz, 1H), 5.94 (dd, J = 6.0, 7.3 Hz, 1H), 6.81 (d, J = 9.2 Hz, 2H), 7.20-7.48 (m, 12H), 7.53 (s, 1H); ¹³C NMR (76 MHz, CDCl₃) δ −4.8, −4.2, 9.4, 10.1, 13.4, 17.8, 25.8, 42.2, 55.2, 58.9, 72.8, 86.1, 87.6, 87.7, 101.3, 113.0, 127.2, 127.7, 128.8, 128.8, 131.2, 136.3, 137.9, 145.9, 156.0, 158.8, 165.8.

(2-2) Synthesis of Compound 9

[Chemical Formula 26]

To an anhydrous pyridine solution (50 mL) of the compound 8 (3.20 g, 4.89 mmol) obtained above was added benzoyl chloride (BzCl; 850 μL, 7.34 mmol), and the mixture was stirred at 0° C. for 1.5 hours. After completion of the reaction, water was added, followed by extraction with ethyl acetate. The organic layer was washed with water, followed by distillation of the solvent under reduced pressure and azeotroped with toluene. The resultant residue was purified by silica-gel column chromatography (SiO₂, containing 1% triethylamine, ethyl acetate/hexane=5% to 26%) to afford a compound 9 (2.99 g, yield: 81%) as a white solid.

Table 7 shows data on the properties of the obtained compound 9.

TABLE 7

Physical property data of the obtained compound 9

$^1$H NMR (300 MHz, CDCl$_3$) δ −0.02 (s, 3H), 0.02 (s, 3H), 0.41-0.58 (m, 2H), 0.82 (s, 9H), 0.87-1.04 (m, 2H), 1.87 (ddd, J = 6.0, 7.8, 13.8 Hz, 1H), 2.06 (d, J = 0.9 Hz, 3H), 2.30 (ddd, J = 2.3, 6.0, 13.8 Hz, 1H), 2.96 (d, J = 2.3 Hz, 1H), 3.80 (s, 3H), 4.04 (ddd, J = 2.3, 2.3, 5.0 Hz, 1H), 5.97 (dd, J = 5.5, 7.8 Hz, 1H), 6.80-6.85 (m, 2H), 7.21-7.55 (m, 15H), 7.64 (d, J = 0.9 Hz, 1H), 8.30-8.33 (m, 2H), 13.33 (bs, 1H).

Table 8 shows data on the properties of the obtained compound 10.

TABLE 8

Physical property data of the obtained compound 10

$^1$H NMR (300 MHz, CDCl$_3$) δ 0.55-0.59 (m, 2H), 0.90-0.10 (m, 2H), 1.71 (bs, 1H), 1.99-2.09 (m, 1H), 2.09 (s, 3H), 2.25 (ddd, J = 4.6, 6.4, 13.8 Hz, 1H), 2.72 (d, J = 4.6 Hz, 1H), 3.82 (s, 3H), 4.46 (d, J = 4.1 Hz, 1H), 5.89 (dd, J = 6.9, 6.9 Hz, 1H), 6.85 (d, J = 8.7 Hz, 2H), 7.15 (s, 1H), 7.23-7.55 (m, 15H), 8.30 (d, J = 7.3 Hz, 2H), 13.20 (bs, 1H).

(2-3) Synthesis of Compound 10

[Chemical Formula 27]

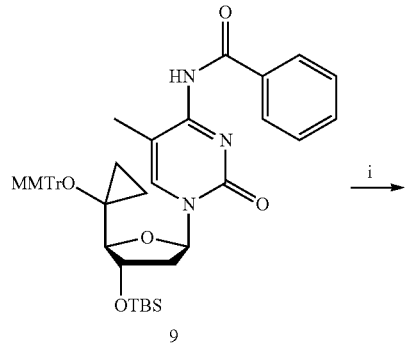

9 i →

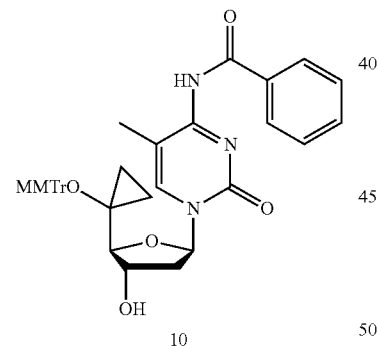

10

(2-4) Synthesis of Compound 11

[Chemical Formula 28]

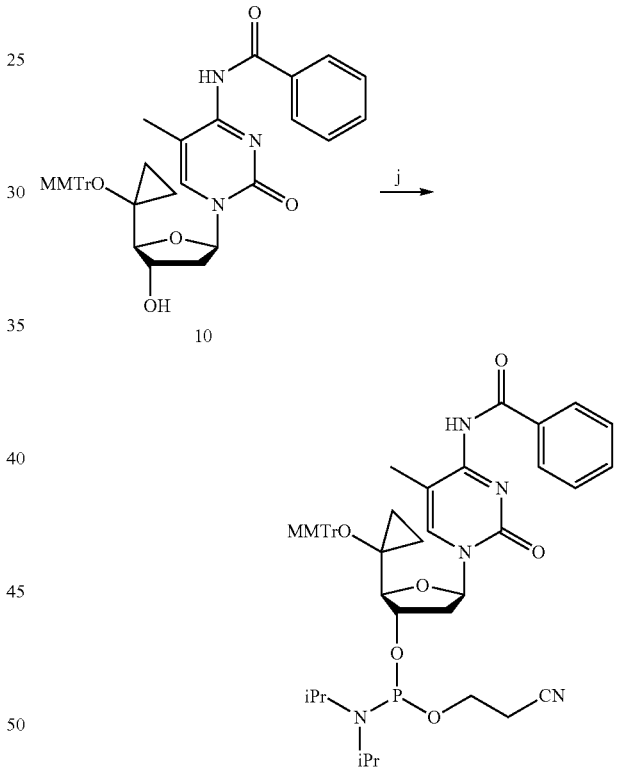

To a tetrahydrofuran solution (77 mL) of the compound 9 (2.91 g, 3.84 mmol) obtained above was added at 0° C. a 1.0 M tetrabutylammonium fluoride (TBAF)tetrahydrofuran solution (4.20 mL, 4.20 mmol), and the mixture was stirred at room temperature for 24 hours. After completion of the reaction, the reaction liquid was distilled away under reduced pressure, and water was added, followed by extraction with ethyl acetate. The organic layer was washed with saturated saline and then dried over anhydrous sodium sulfate, and the solvent was distilled away under reduced pressure. The resultant residue was purified by silica-gel column chromatography (SiO$_2$, containing 1% triethylamine, ethyl acetate/hexane=29% to 70%) to afford a compound 10 (2.38 g, yield: 96%) as a white solid.

Under nitrogen stream, to an anhydrous acetonitrile solution (36 mL) of the compound 10 (2.29 g, 3.56 mmol) obtained above were added sequentially at 0° C. N,N-diisopropylethylamine (DIEPA; 1.85 mL, 10.8 mmol) and 2-cyanoethyl-N,N-diisopropyl phosphorochloridate (iPr$_2$NP(Cl)OCH$_2$CH$_2$CN; 1.20 mL, 5.34 mmol), and the mixture was stirred at room temperature for 3 hours. After completion of the reaction, the solvent was distilled away under reduced pressure, and the resultant residue was purified by silica-gel column chromatography (SiO$_2$, containing 1% triethylamine, ethyl acetate/hexane=20% to 40%) to afford a compound 11 (2.08 g, yield: 69%) as a yellow solid.

Table 9 shows data on the properties of the obtained compound 11.
TABLE 9
Physical property data of the obtained compound 11
$^1$H NMR (300 MHz, CDCl$_3$) δ 0.47-0.64 (m, 2H), 0.91-1.02 (m, 2H), 1.09 (d, J = 6.4 Hz, 3H), 1.15 (d, J = 6.9 Hz, 6H), 1.18 (d, J = 6.9 Hz, 3H), 1.84-1.97 (m, 1H), 2.06 (d, J = 0.9 Hz, 1.2H), 2.06 (d, J = 0.9 Hz, 1.8H), 2.47-2.65 (m, 3H), 3.00 (d, J = 1.4 Hz, 0.4H), 3.10 (s, 0.6H), 3.48-3.69 (m, 4H), 3.80 (s, 1.2H), 3.81 (s, 1.8H), 4.33-4.44 (m, 1H), 5.93-5.98 (m, 1H), 6.79-6.85 (m, 2H), 7.23-7.55 (m, 16H), 8.31 (d, J = 7.3 Hz, 2H), 13.29 (bs, 1H); $^{31}$P NMR (121.7 MHz, CDCl$_3$) δ 148.1, 149.5.
Example 3
Synthesis of 5'-Modified Nucleoside (3)
[Chemical Formula 29]
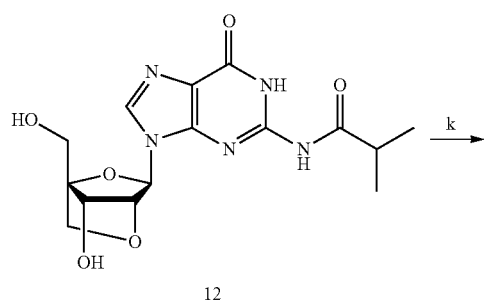
12
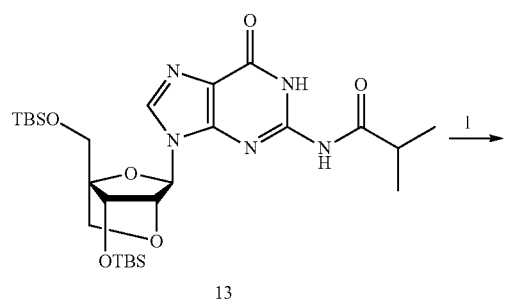
13
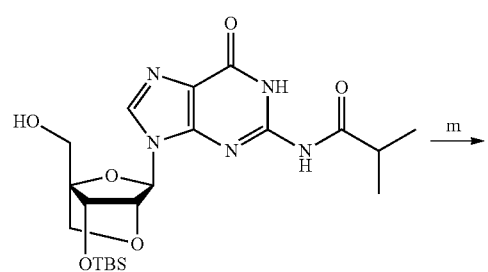
14
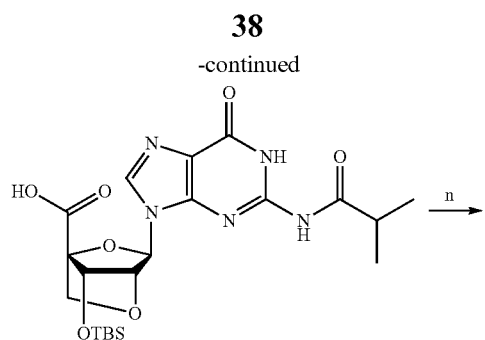
15
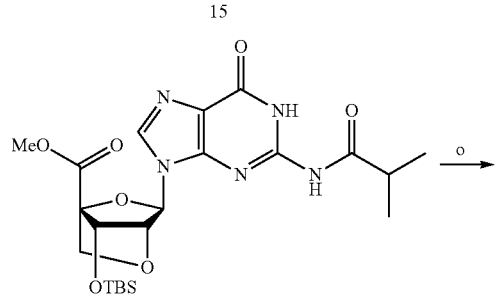
16
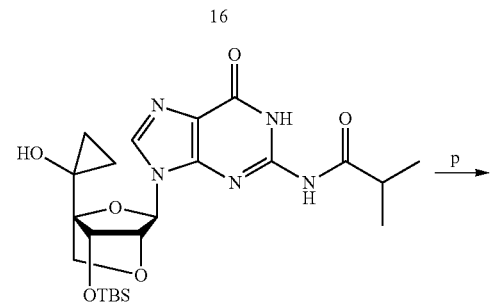
17
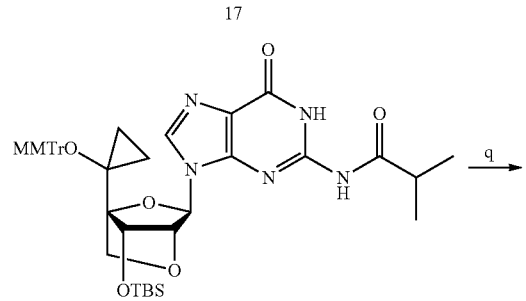
18
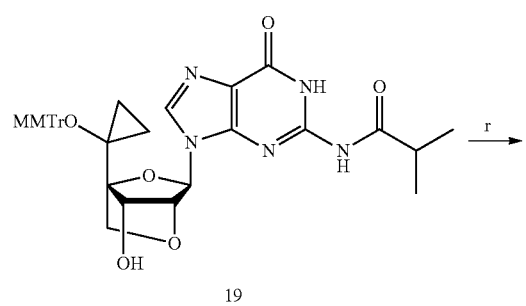
19

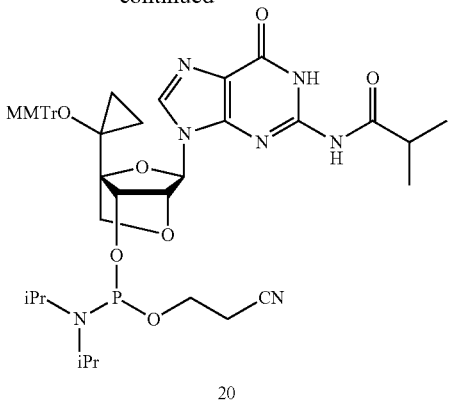

Reagents and conditions under each step: (k) TBSCl, imizazole, pyridine, reflux, 20 hours, 93%; (l) TFA, THF, H₂O, 0° C., 6 hors, quantitative; (m) TEMPO, PhI(OAc)₂, H₂O, CH₂Cl₂, MeCN, 3 hours, 83%; (n) EDC•HCl, CH₂ClCH₂Cl, 50° C., 2 hours; MeOH, 60° C., 5 hours, 75%; (o) EtMgBr, Ti(OiPr)₄, THF, 0° C. to r.t., 5.5 hours, 22%; (p) MMTrCl, AgNO₃, THF, pyridine, 50° C., 2 hours, 85%; (q) TBAF, THF, r.t., 1 hour, 89%; (r) iPr₂NP(Cl)OCH₂CH₂CN, DIPEA, CH₂Cl₂, r.t., 3.5 hours, 72%.

(3-1) Synthesis of Compound 13

[Chemical Formula 30]

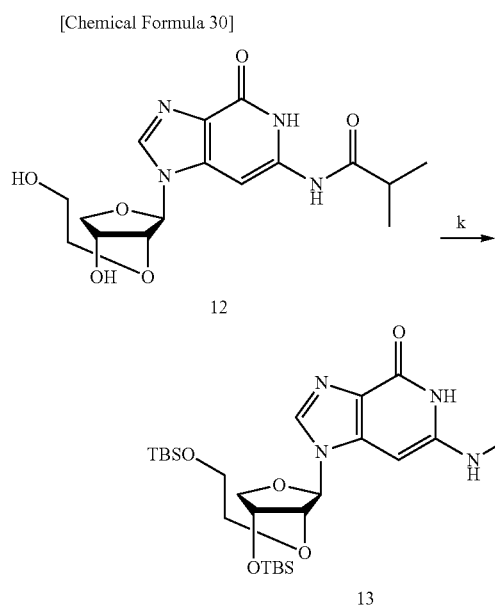

Under nitrogen stream, to an anhydrous pyridine solution (320 mL) of a compound 12 (11.7 g, 31.9 mmol), the compound 12 being prepared using a method described in Lomholt et al., J. Org. Chem., 2001, Vol. 66, No. 25, pp. 8504-8512, were added sequentially at room temperature imidazole (10.9 g, 160 mmol) and tert-butyldimethylchlorosilane (TBSCl; 24.2 g, 161 mmol). After heat refluxing for 17 hours, imidazole (2.16 g, 31.7 mmol) and tert-butyldimethylchlorosilane (TBSCl; 4.89 g, 32.4 mmol) were added again, and the mixture was heat refluxed for additional 3 hours. After completion of the reaction, water was added, and the pyridine solvent was distilled away under reduced pressure, followed by extraction with ethyl acetate. The organic layer was washed with water, followed by distillation of the solvent under reduced pressure and azeotroped with toluene. The resultant residue was purified by silica-gel column chromatography (SiO₂, ethyl acetate/hexane=30%, then 60%) to afford a compound 13 (17.6 g, yield: 93%) as a white solid.

Table 10 shows data on the properties of the obtained compound 13.

TABLE 10

Physical property data of the obtained compound 13

¹H NMR (300 MHz, CDCl₃) δ 0.01 (s, 3H), 0.03 (s, 3H), 0.10 (s, 6H), 0.86 (s, 9H), 0.92 (s, 9H), 1.28 (d, J = 7.3 Hz, 3H), 1.29 (d, J = 6.9 Hz, 3H), 2.58-2.72 (m, 1H), 3.80 (d, J = 7.3 Hz, 1H), 3.88 (d, J = 11.9 Hz, 1H), 3.94 (d, J = 11.9 Hz, 1H), 4.00 (d, J = 7.3 Hz, 1H), 4.24 (s, 1H), 4.28 (s, 1H), 5.78 (s, 1H), 7.90 (s, 1H), 8.41 (bs, 1H), 12.00 (bs, 1H).

(3-2) Synthesis of Compound 14

[Chemical Formula 31]

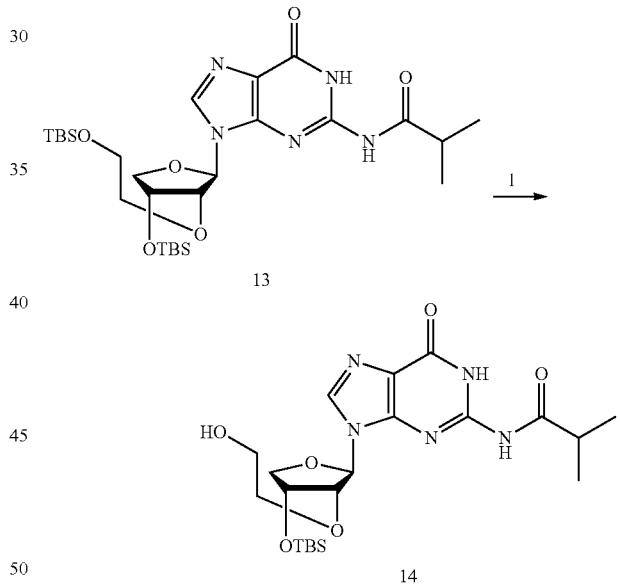

To a tetrahydrofuran solution (355 mL) of the compound 13 (17.6 g, 29.6 mmol) obtained above was added a trifluoroacetic acid/water mixed solution (=1:1 (volume ratio), 178 mL), and the mixture was stirred at 0° C. for 6 hours. The reaction solution was added dropwise to a saturated aqueous solution of sodium hydrogen carbonate, followed by extraction with ethyl acetate. The organic layer was washed with saturated saline and then dried over anhydrous sodium sulfate, and the solvent was distilled away under reduced pressure. The resultant residue was purified by recrystallization (hexane/ethyl acetate), and the remaining filtrate was also purified by silica-gel column chromatography (SiO₂, methanol/chloroform=0% to 8%) to afford a compound 14 (13.9 g, quantitative) as a white solid.

Table 11 shows data on the properties of the obtained compound 14.

TABLE 11

Physical property data of the obtained compound 14

$^1$H NMR (300 MHz, CDCl$_3$) δ 0.06 (s, 3H), 0.09 (s, 3H), 0.87 (s, 9H), 1.27 (d, J = 1.8 Hz, 3H), 1.29 (d, J = 1.8 Hz, 3H), 2.65-2.79 (m, 1 H), 3.65 (bs, 1H), 3.85 (d, J = 7.8 Hz, 1H), 3.89 (d, J = 12.4 Hz, 1 H), 4.01 (d, J = 12.4 Hz, 1H), 4.03 (d, J = 7.8 Hz, 1H), 4.29 (s, 1H), 4.50 (s, 1H), 5.83 (s, 1H), 7.86 (s, 1H), 9.01 (bs, 1H), 12.01 (bs, 1H).

(3-3) Synthesis of Compound 15

[Chemical Formula 32]

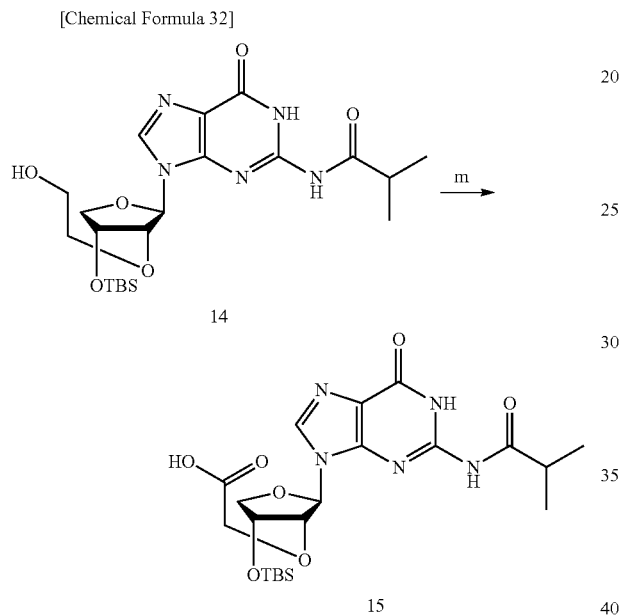

To a dichloromethane solution (270 mL) of the compound 14 (12.9 g, 27.0 mmol) obtained above were added sequentially at 0° C. acetonitrile/water (=1:1 (volume ratio), 1.48 mL), iodobenzene diacetate (PhI(OAc)$_2$; 43.4 g, 134.8 mmol), and 2,2,6,6-tetramethylpiperidine 1-oxyl free radical (TEMPO; 1.29 g, 8.59 mmol), and the mixture was stirred at room temperature for 3 hours. After completion of the reaction, methanol (30 mL) was added to the mixture, and the mixture was stirred at room temperature for 20 minutes, followed by distillation of the solvent under reduced pressure and azeotroped with toluene. The resultant residue was purified by silica-gel column chromatography (DIOL-SiO$_2$, methanol/chloroform=0% to 20%). In addition, the crude product that could not be purified was purified by trituration (ethyl acetate/hexane) to afford a compound 15 (11.0 g, yield: 83%) as a white solid.

Table 12 shows data on the properties of the obtained compound 15.

TABLE 12

Physical property data of the obtained compound 15

$^1$H NMR (300 MHz, CD$_3$OD) δ 0.06 (s, 3H), 0.07 (s, 3H), 0.87 (s, 9H), 1.22 (d, J = 6.9 Hz, 6H), 2.66-2.75 (m, 1H), 4.06 (d, J = 7.9 Hz, 1H),

TABLE 12-continued

Physical property data of the obtained compound 15

4.45 (d, J = 8.3 Hz, 1H), 4.49 (s, 1H), 4.59 (s, 1H), 5.97 (s, 1H), 8.12 (s, 1H).

(3-4) Synthesis of Compound 16

[Chemical Formula 33]

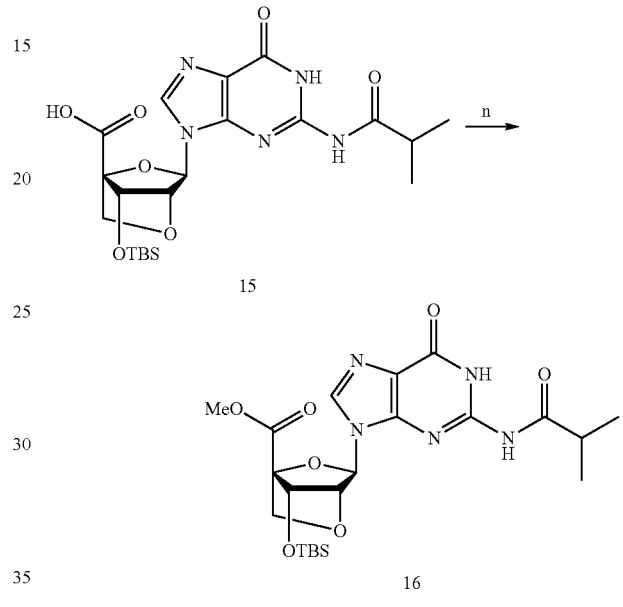

Under nitrogen stream, to a 1,2-dichloroethane solution (220 mL) of the compound 15 (11.0 g, 22.3 mmol) obtained above was added at room temperature 1-(3-dimethylaminopropyl)-3-ethylcarbodiimide hydrochloride (EDC·HCl; 8.56 g, 44.7 mmol), and the mixture was stirred at 50° C. for 2 hours. After disappearance of the starting material, anhydrous methanol (220 mL) was added, followed by stirring at 60° C. for additional 5 hours. After completion of the reaction, the reaction liquid was distilled away under reduced pressure, and water was added, followed by extraction with chloroform. The organic layer was washed with water and saturated saline and then dried over anhydrous sodium sulfate, and the solvent was distilled away under reduced pressure. The resultant residue was purified by silica-gel column chromatography (SiO$_2$, methanol/chloroform=0% to 4%) to afford a compound 16 (8.53 g, yield: 75%) as a white solid.

Table 13 shows data on the properties of the obtained compound 16.

TABLE 13

Physical property data of the obtained compound 16

$^1$H NMR (300 MHz, CDCl$_3$) δ 0.02 (s, 6H), 0.85 (s, 9H), 1.28 (d, J = 6.9 Hz, 3H), 1.29 (d, J = 6.9 Hz, 3H), 2.59-2.73 (m, 1H), 3.85 (s, 3 H), 4.07 (d, J = 8.3 Hz, 1H), 4.39 (s, 1H), 4.47 (d, J = 8.3 Hz, 1H), 4.48 (s, 1H), 5.83 (s, 1H), 7.91 (s, 1H), 8.44 (bs, 1H), 12.03 (bs, 1H); HRMS (MALDI) Calculated for C$_{22}$H$_{33}$N$_5$O$_7$NaSi [M + Na]$^+$: 530.2041, Found: 530.2042.

(3-5) Synthesis of Compound 17

[Chemical Formula 34]

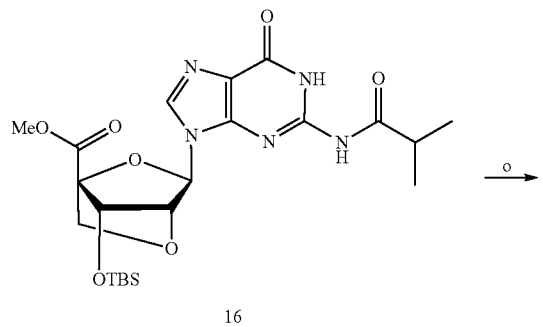

16

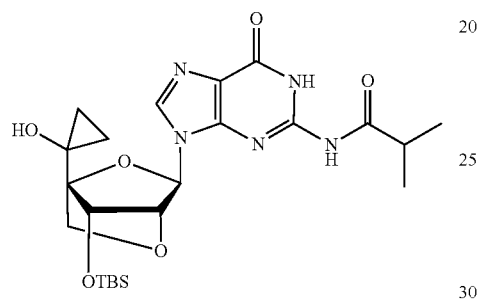

17

Under nitrogen stream, to an anhydrous tetrahydrofuran solution (10 mL) of the compound 16 (514 mg, 1.01 mmol) obtained above and titanium tetraisopropoxide (Ti(OiPr)$_4$; 300 µL, 1.01 mmol) was added dropwise at 0° C. over 2.5 hours a 1.0 M ethyl magnesium bromide (EtMgBr)·tetrahydrofuran solution (8.1 mL, 8.1 mmol). After the dropwise addition, the reaction solution was warmed to room temperature and stirred for additional 3 hours. After completion of the reaction, Celite filtration was performed after a saturated aqueous solution of ammonium chloride was added thereto, and the filtrate was extracted with ethyl acetate. The organic layer was washed with water and saturated saline and then dried over anhydrous sodium sulfate, and the solvent was distilled away under reduced pressure. The resultant residue was purified by silica-gel column chromatography (NH$_2$—SiO$_2$, methanol/chloroform=0% to 2% and then 5%) to afford a compound 17 (114 mg, 22%) as a yellow solid.

Table 14 shows data on the properties of the obtained compound 17.

TABLE 14

Physical property data of the obtained compound 17

$^1$H NMR (300 MHz, CDCl$_3$) δ 0.06 (s, 3H), 0.09 (s, 3H), 0.64-0.69 (m, 1H), 0.78-1.08 (m, 3H), 0.88 (s, 9H), 1.29 (d, J = 6.9 Hz, 6H), 2.62-2.76 (m, 1H), 3.78 (d, J = 7.6 Hz, 1H), 3.96 (d, J = 7.6 Hz, 1H), 4.05 (bs, 1H), 4.30 (s, 1H), 4.50 (s, 1H), 5.85 (s, 1H), 7.89 (s, 1H), 8.65 (bs, 1H), 12.00 (bs, 1H); HRMS (MALDI) Calculated for C$_{23}$H$_{35}$N$_5$O$_6$NaSi [M + Na]$^+$: 528.2249, Found: 528.2251.

(3-6) Synthesis of Compound 18

[Chemical Formula 35]

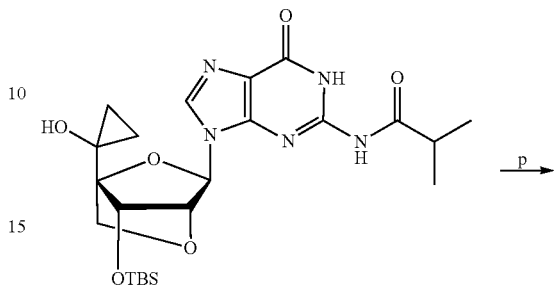

17

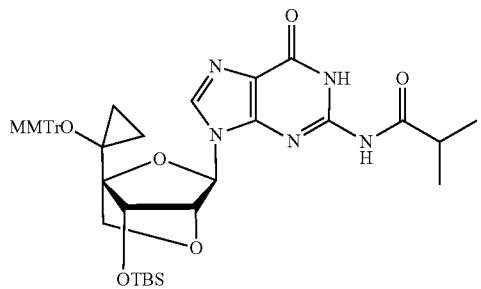

18

Under nitrogen stream, to an anhydrous pyridine/tetrahydrofuran mixed solution (=1:4 (volume ratio), 125 mL) of the compound 17 (1.59 g, 3.14 mmol) obtained above were added sequentially 4-methoxytrityl chloride (MMTrCl; 4.30 g, 13.9 mmol) and silver nitrate (2.29 g, 13.5 mmol), and the mixture was stirred at 50° C. for 2 hours. After completion of the reaction, Celite filtration was performed after a saturated aqueous solution of sodium hydrogen carbonate was added thereto, and the filtrate was extracted with ethyl acetate. The organic layer was washed twice with a saturated aqueous solution of sodium thiosulfate and once with a water/saturated saline mixed solution (=1:1 (volume ratio)) and then dried over anhydrous sodium sulfate, followed by distillation of the solvent under reduced pressure and azeotroped with toluene. The resultant residue was purified by silica-gel column chromatography (NH$_2$—SiO$_2$, methanol/chloroform=0% to 2%) to afford a compound 18 (2.08 g, yield: 85%) as a yellow solid.

Table 15 shows data on the properties of the obtained compound 18.

TABLE 15

Physical property data of the obtained compound 18

$^1$H NMR (300 MHz, CDCl$_3$) δ −0.04 (s, 6H), 0.63-1.11 (m, 4H), 0.87 (s, 9H), 1.27 (d, J = 6.9 Hz, 6H), 2.56-2.70 (m, 1H), 3.58 (s, 1H), 3.65 (d, J = 8.3 Hz, 1H), 3.75 (s, 3H), 3.80 (d, J = 8.3 Hz, 1H), 4.30 (s, 1H), 5.36 (s, 1H), 6.79 (d, J = 9.2 Hz, 2H), 7.16-7.43 (m, 12H), 7.59 (s, 1H), 8.42 (bs, 1H), 11.99 (bs, 1H).

(3-7) Synthesis of Compound 19

[Chemical Formula 36]

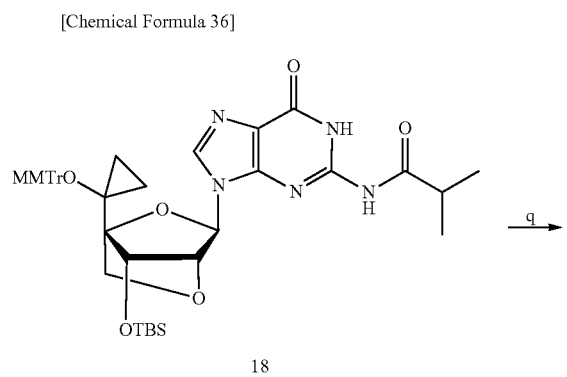

18

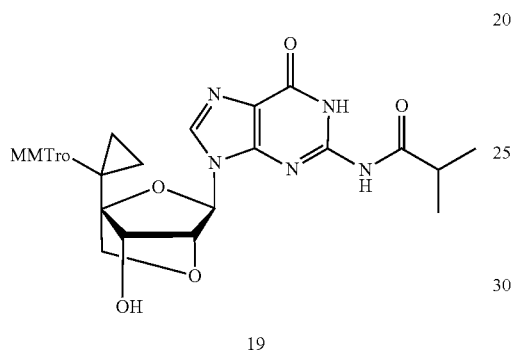

19

To a tetrahydrofuran solution (52 mL) of the compound 18 (2.01 g, 2.59 mmol) obtained above was added at 0° C. a 1.0 M tetrabutylammonium fluoride (TBAF)·tetrahydrofuran solution (2.90 mL, 2.90 mmol), and the mixture was stirred at room temperature for an hour. After completion of the reaction, the reaction liquid was distilled away under reduced pressure, and water was added, followed by extraction with ethyl acetate. The organic layer was washed with water and saturated saline and then dried over anhydrous sodium sulfate, and the solvent was distilled away under reduced pressure. The resultant residue was purified by silica-gel column chromatography ($NH_2$—$SiO_2$, methanol/chloroform=0% to 7%), and further purified by separation with water to afford a compound 19 (1.53 g, 89%) as a light yellow solid.

Table 16 shows data on the properties of the obtained compound 19.

TABLE 16

Physical property data of the obtained compound 19

$^1$H NMR (300 MHz, $CDCl_3$) δ 0.85-1.27 (m, 4H), 1.23 (d, J = 6.9 Hz, 3H), 1.26 (d, J = 7.3 Hz, 3H), 2.62-2.76 (m, 1H), 3.68 (d, J = 8.3 Hz, 1H), 3.76 (s, 3H), 3.84 (s, 2H), 3.89 (d, J = 8.7 Hz, 1H), 4.31 (s, 1H), 5.32 (s, 1H), 6.80 (d, J = 8.7 Hz, 2H), 7.16-7.43 (m, 12H), 7.61 (s, 1H), 9.23 (bs, 1H), 12.04 (bs, 1H); HRMS (MALDI) Calculated for $C_{37}H_{37}N_5O_7Na$ $[M + Na]^+$: 686.2585, Found: 686.2584.

(3-8) Synthesis of Compound 20

[Chemical Formula 37]

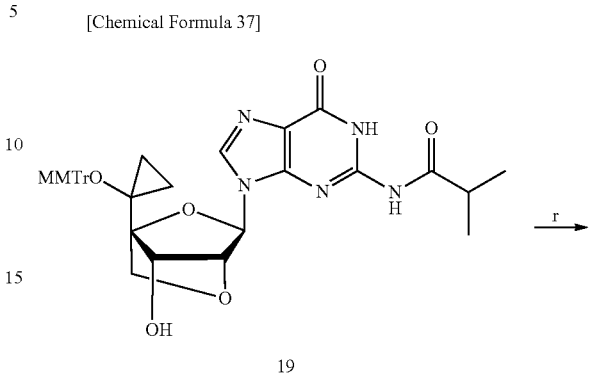

19

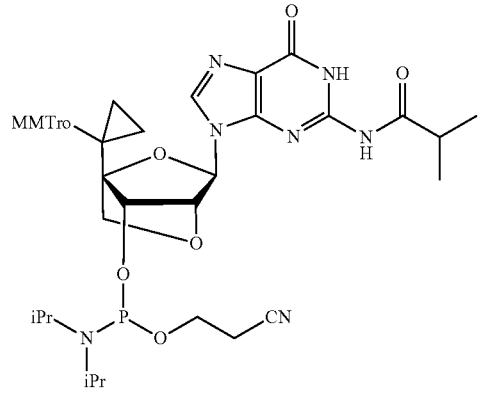

20

Under nitrogen stream, to a deoxygenated dichloromethane solution (11 mL) of the compound 19 (733 mg, 1.11 mmol) obtained above were added sequentially at 0° C. N,N-diisopropylethylamine (DIPEA; 1.5 mL, 8.77 mmol) and 2-cyanoethyl-N,N-diisopropyl phosphorochloridate ($iPr_2NP(Cl)OCH_2CH_2CN$; 1.0 mL, 4.48 mmol), and the mixture was stirred at room temperature for 3.5 hours. After completion of the reaction, the solvent was distilled away under reduced pressure, and the resultant residue was purified by silica-gel column chromatography ($SiO_2$, hexane: ethyl acetate:methanol=15:15:1 (volume ratio)). Then, silica-gel column chromatography ($NH_2$—$SiO_2$, methanol/chloroform=0% to 3%) was performed again. Finally, reprecipitation (ethyl acetate/hexane) was performed to afford a compound 20 (626 mg, yield: 72%) as a white solid.

Table 17 shows data on the properties of the obtained compound 20.

TABLE 17

Physical property data of the obtained compound 20

$^1$H NMR (300 MHz, $CDCl_3$) δ 0.65-0.72 (m, 1H), 0.86-0.93 (m, 4H), 1.09-1.26 (m, 18H), 2.45-2.72 (m, 3H), 3.40-4.02 (m, 10H), 4.86 (s, 0.5H), 5.00 (s, 0.5H), 5.28 (s, 1H), 6.81 (d, J = 8.7 Hz, 2H), 7.17-7.45 (m, 12H), 7.57 (s, 1H), 8.66 (bs, 0.5H), 8.87 (bs, 0.5H), 11.94 (bs, 0.5H), 11.98 (bs, 0.5H); $^{31}$P NMR (121.7 MHz, $CDCl_3$) δ 142.5, 147.4; HRMS (MALDI) Calculated for $C_{46}H_{54}N_7O_8NaP$ $[M + Na]^+$: 886.3664, Found: 886.3664.

Example 4
Synthesis of 5'-Modified Nucleoside (4)
[Chemical Formula 38]
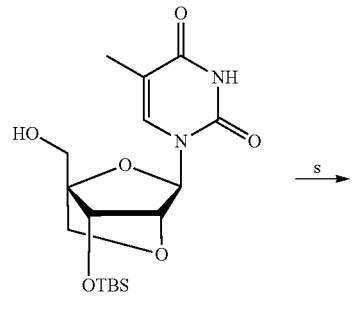
21
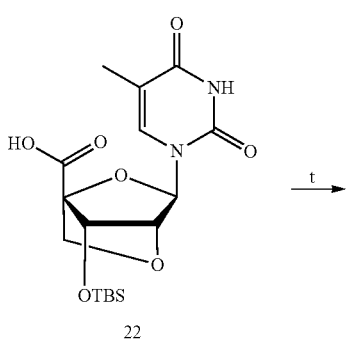
22
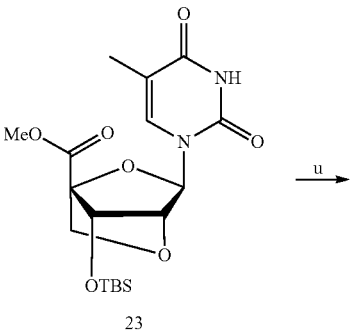
23
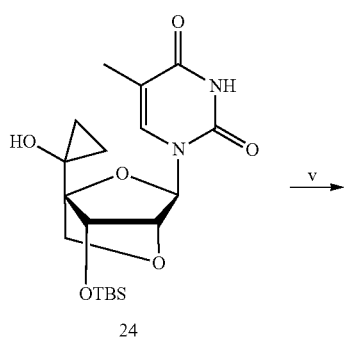
24
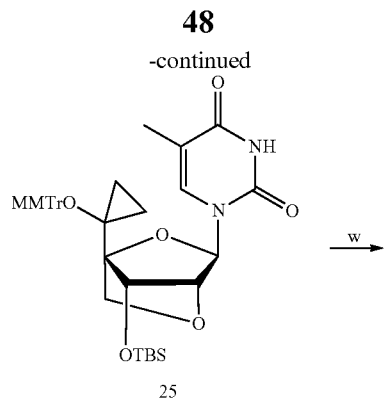
25
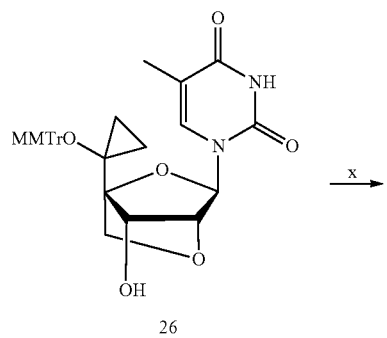
26
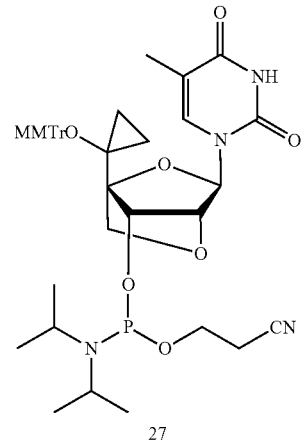
27
Reagents and conditions under each step: (s) TEMPO, PhI(OAc)$_2$, H$_2$O, CH$_2$Cl$_2$, MeCN, r.t., 14 hours, 78%; (t) EDC•HCl, CH$_2$ClCH$_2$Cl, 50° C., 1.5 hours; MeOH, 60° C., 2.5 hours, 69%; (u) EtMgBr, Ti(OiPr)$_4$, THF, 0° C. to r.t., 5.5 hours, 35%; (v) MMTrCl, AgNO$_3$, pyridine, THF, 50° C., 4.5 hours, 36%; (w) TBAF. THF, r.t., 1 hour, 97%; (x) iPr$_2$NP(Cl)OCH$_2$CH$_2$CN, DIPEA, MeCN, r.t., 4 hours, 77%.

(4-1) Synthesis of Compound 22

[Chemical Formula 39]

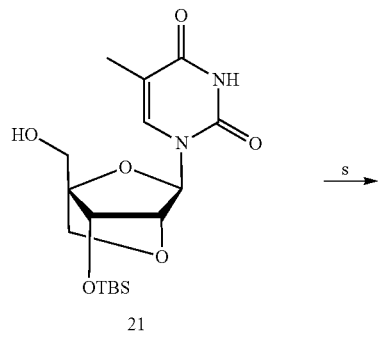

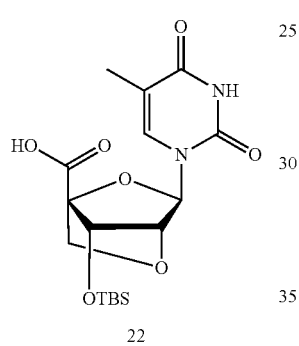

To a dichloromethane solution (7.7 mL) of a compound 21 (295 mg, 0.77 mmol), the compound 21 being prepared using a method described in Lomholt et al., J. Org. Chem., 2001, Vol. 66, No. 25, pp. 8504-8512, were added sequentially at 0° C. acetonitrile/water (=1:1 (volume ratio), 42.2 μL), iodobenzene diacetate (PhI(OAc)$_2$; 548 mg, 1.70 mmol), and 2,2,6,6-tetramethylpiperidine 1-oxyl free radical (TEMPO; 37 mg, 0.24 mmol), and the mixture was stirred at room temperature for 14 hours. After completion of the reaction, methanol (7.7 mL) was added to the mixture, and the mixture was stirred at room temperature for 15 minutes, followed by distillation of the solvent under reduced pressure. The resultant residue was purified by trituration (ethyl acetate/hexane) to afford a compound 22 (240 mg, yield: 78%) as a white solid.

Table 18 shows data on the properties of the obtained compound 22.

TABLE 18

Physical property data of the obtained compound 22

$^1$H NMR (300 MHz, CD$_3$OD) δ 0.10 (s, 3H), 0.10 (s, 3H), 0.90 (s, 9H), 1.92 (d, J = 0.9 Hz, 3H), 3.99 (d, J = 7.8 Hz, 1H), 4.30 (s, 1H), 4.35 (s, 1H), 4.39 (d, J = 7.8 Hz, 1H), 5.57 (s, 1H), 7.73 (d, J = 1.4 Hz, 1H).

(4-2) Synthesis of Compound 23

[Chemical Formula 40]

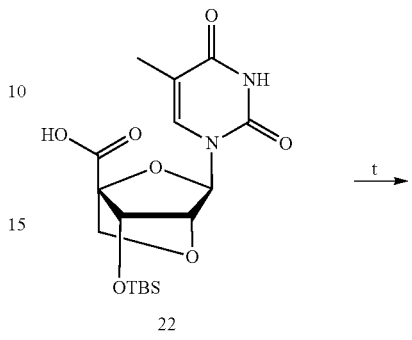

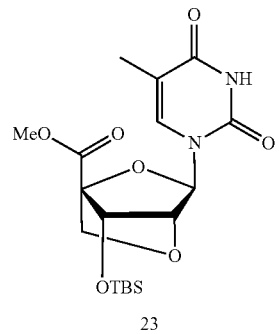

Under nitrogen stream, to a 1,2-dichloroethane solution (4.7 mL) of the compound 22 (188 mg, 0.47 mmol) obtained above was added at room temperature 1-(3-dimethylaminopropyl)-3-ethylcarbodiimide hydrochloride (EDC·HCl; 189 mg, 0.99 mmol), and the mixture was stirred at 50° C. for 1.5 hours. After disappearance of the starting material, anhydrous methanol (4.7 mL) was added, followed by stirring at 60° C. for additional 2.5 hours. After completion of the reaction, the reaction liquid was distilled away under reduced pressure, and water was added, followed by extraction with ethyl acetate. The organic layer was washed with water and saturated saline and then dried over anhydrous sodium sulfate, and the solvent was distilled away under reduced pressure. The resultant residue was purified by silica-gel column chromatography (SiO$_2$, ethyl acetate/hexane=40% to 65%) to afford a compound 23 (135 mg, yield: 69%) as a white solid.

Table 19 shows data on the properties of the obtained compound 23.

TABLE 19

Physical property data of the obtained compound 23

$^1$H NMR (300 MHz, CDCl$_3$) δ 0.04 (s, 3H), 0.07 (s, 3H), 0.87 (s, 9H), 1.98 (d, J = 0.9 Hz, 3H), 3.86 (s, 3H), 4.03 (d, J = 8.3 Hz, 1H), 4.20 (s, 1H), 4.40 (s, 1H), 4.43 (d, J = 7.8 Hz, 1H), 5.61 (s, 1H), 7.56 (d, J = 1.4 Hz, 1H), 8.35 (bs, 1H).

(4-3) Synthesis of Compound 24

[Chemical Formula 41]

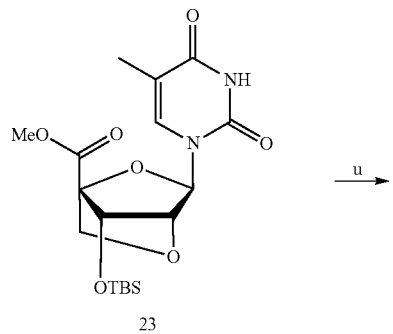

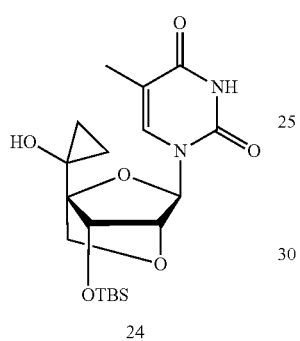

Under nitrogen stream, to an anhydrous tetrahydrofuran solution (208 mL) of the compound 23 (8.56 g, 20.8 mmol) obtained above and titanium tetraisopropoxide (Ti(OiPr)$_4$; 6.15 mL, 20.8 mmol) was added dropwise at 0° C. over 2.5 hours a 1.0 M ethyl magnesium bromide (EtMgBr)·tetrahydrofuran solution (106 mL, 106 mmol). After the dropwise addition, the reaction solution was warmed to room temperature and stirred for additional 3 hours. After completion of the reaction, Celite filtration was performed after a saturated aqueous solution of ammonium chloride was added thereto, and the filtrate was extracted with ethyl acetate. The organic layer was washed with water and saturated saline and then dried over anhydrous sodium sulfate, and the solvent was distilled away under reduced pressure. The resultant residue was purified by silica-gel column chromatography (SiO$_2$, ethyl acetate/hexane=50% to 80%) to afford a compound 24 (3.01 g, yield: 35%) as a light yellow solid.

Table 20 shows data on the properties of the obtained compound 24.

TABLE 20

Pysical property data of the obtained compound 24

$^1$H NMR (300 MHz, CDCl$_3$) δ 0.10 (s, 6H), 0.60-1.00 (m, 4H), 0.89 (s, 9H), 1.94 (s, 3H), 2.85 (s, 1H), 3.73 (d, J = 7.3 Hz, 1H), 3.93 (d, J = 7.3 Hz, 1H), 3.93 (d, J = 7.3 Hz, 1H), 4.08 (s, 1H), 4.32 (s, 1H), 7.49 (s, 1H), 8.81 (bs, 1H).

(4-4) Synthesis of Compound 25

[Chemical Formula 42]

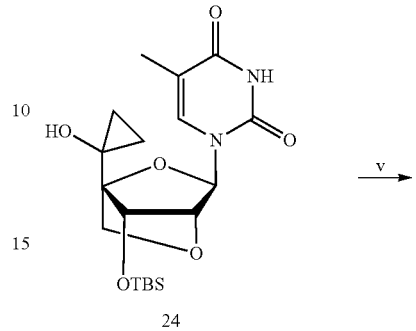

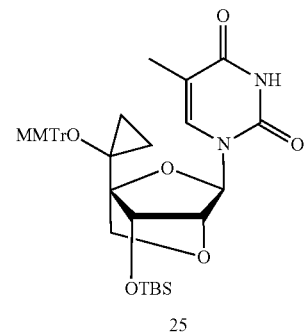

Under nitrogen stream, to an anhydrous pyridine/tetrahydrofuran mixed solution (=1:4 (volume ratio), 276 mL) of the compound 24 (2.84 g, 6.92 mmol) obtained above were added sequentially 4-methoxytrityl chloride (MMTrCl; 9.40 g, 30.4 mmol) and silver nitrate (5.05 g, 29.7 mmol), and the mixture was stirred at 50° C. for 4.5 hours. After completion of the reaction, Celite filtration was performed after a saturated aqueous solution of sodium hydrogen carbonate was added thereto, and the filtrate was extracted with ethyl acetate. The organic layer was washed twice with a saturated aqueous solution of sodium thiosulfate, once with a water/saturated saline mixed solution (=1:1 (volume ratio)), and once with saturated saline and then dried over anhydrous sodium sulfate, followed by distillation of the solvent under reduced pressure and azeotroped with toluene. The resultant residue was purified by silica-gel column chromatography (NH$_2$—SiO$_2$, ethyl acetate/hexane=60% to 100% and then methanol/ethyl acetate=2%), and then silica-gel column chromatography (NH$_2$—SiO$_2$, methanol/chloroform=0% to 1%) was performed again, to afford a compound 25 (1.70 g, yield: 36%) as a yellow solid.

Table 21 shows data on the properties of the obtained compound 25.

TABLE 21

Physical property data of the obtained compound 25

$^1$H NMR (300 MHz, CDCl$_3$) δ 0.01 (s, 3H), 0.04 (s, 3H), 0.52-0.58 (m, 1H), 0.88 (s, 9H), 1.04-1.08 (m, 3H), 1.82 (s, 3H), 3.50 (s, 1H), 3.61 (d, J = 8.3 Hz, 1H), 3.65 (d, J = 7.8 Hz, 1H), 3.77 (s, 3H), 4.26 (s, 1H), 5.17 (s, 1H), 6.79 (d, J = 8.7 Hz, 2H), 7.19-7.46 (m, 13H), 8.22 (bs, 1H).

(4-5) Synthesis of Compound 26

[Chemical Formula 43]

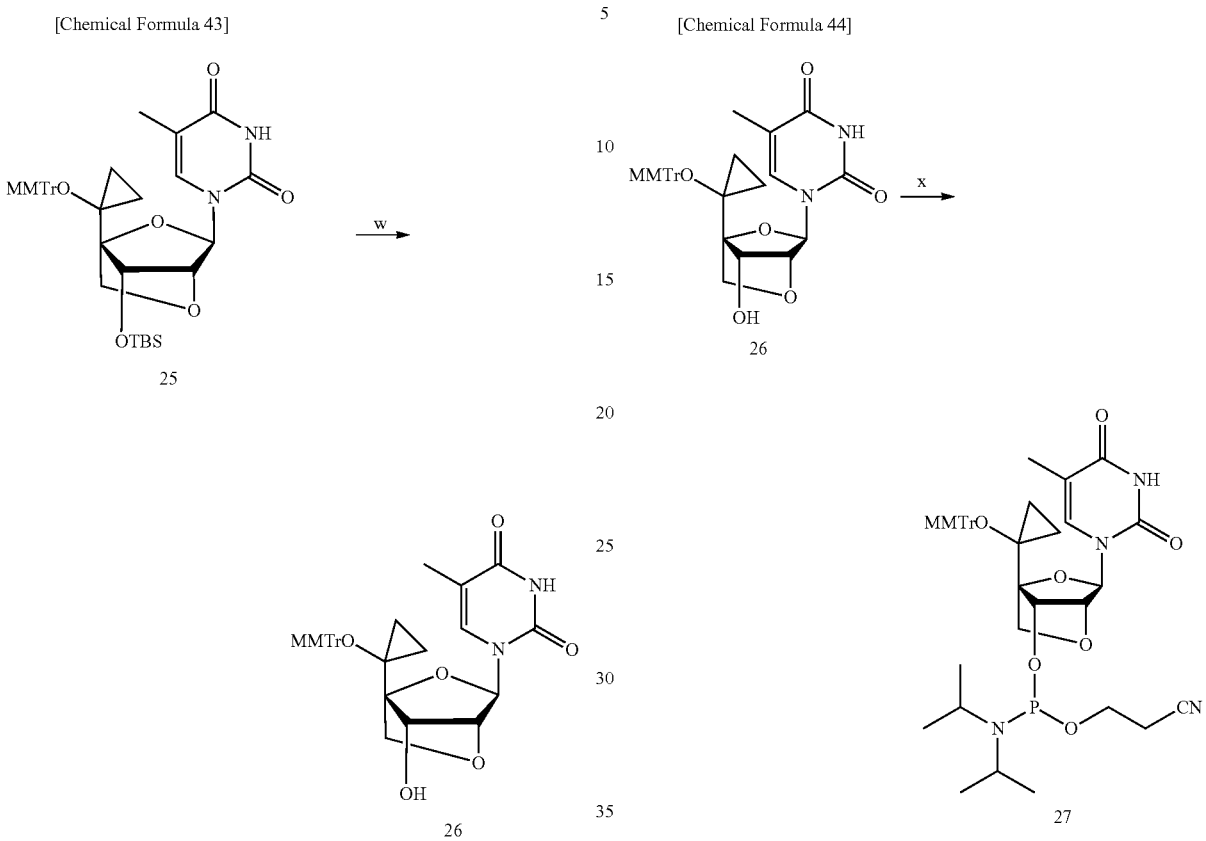

To a tetrahydrofuran solution (21 mL) of the compound 25 (731 mg, 1.07 mmol) obtained above was added at 0° C. a 1.0 M tetrabutylammonium fluoride (TBAF)·tetrahydrofuran solution (1.15 mL, 1.15 mmol), and the mixture was stirred at room temperature for an hour. After completion of the reaction, the reaction liquid was distilled away under reduced pressure, and water was added, followed by extraction with ethyl acetate. The organic layer was washed with saturated saline and then dried over anhydrous sodium sulfate, and the solvent was distilled away under reduced pressure. The resultant residue was purified by silica-gel column chromatography ($SiO_2$, methanol/chloroform=0% to 5%) to afford a compound 26 (592 mg, yield: 97%) as a light yellow solid.

Table 22 shows data on the properties of the obtained compound 26.

TABLE 22

Physcial property data of the obtained compound 26

$^1$H NMR (300 MHz, $CDCl_3$) δ 0.66-0.74 (m, 1H), 1.02-1.27 (m, 3H), 1.78 (d, J = 0.9 Hz, 3H), 2.09 (bs, 1H), 3.27 (s, 1H), 3.69 (d, J = 8.7 Hz, 1H), 3.74 (d, J = 8.7 Hz, 1H), 3.77 (s, 3H), 4.23 (s, 1H), 5.22 (s, 1H), 6.79-6.85 (m, 2H), 7.14 (d, J = 1.4 Hz, 1H), 7.19-7.46 (m, 12H), 8.56 (bs, 1H)

(4-6) Synthesis of Compound 27

[Chemical Formula 44]

Under nitrogen stream, to an anhydrous acetonitrile solution (9.5 mL) of the compound 26 (540 mg, 0.95 mmol) obtained above were added sequentially at 0° C. N,N-diisopropylethylamine (DIPEA; 490 μL, 2.87 mmol) and 2-cyanoethyl-N,N-diisopropyl phosphorochloridate ($iPr_2NP$(Cl)$OCH_2CH_2CN$; 320 μL, 1.43 mmol), and the mixture was stirred at room temperature for 4 hours. After completion of the reaction, the solvent was distilled away under reduced pressure, and the resultant residue was purified by silica-gel column chromatography ($SiO_2$, ethyl acetate/hexane=50% to 77%). Finally, reprecipitation (chloroform/hexane) was performed to afford a compound 27 (562 mg, yield: 77%) as a white solid.

Table 23 shows data on the properties of the obtained compound 27.

TABLE 23

Physical property data of the obtained compound 27

$^1$H NMR (300 MHz, $CDCl_3$), δ 0.62-0.73 (m, 1H), 1.04-1.25 (m, 15H), 1.83 (d, J = 0.9 Hz, 1.8H), 1.85 (s, 1.2H), 2.51-2.62 (m, 2H), 3.45-3.82 (m, 10H), 4.52 (s, 1H), 5.17 (s, 0.6H), 5.20 (s, 0.4H), 6.79 (d, J = 8.7 Hz, 2H), 7.12-7.46 (m, 13H), 8.24 (bs, 1H), $^{31}$P NMR (121.7 MHz, $CDCl_3$) δ 148.3, 148.7.

Example 5

Synthesis of 5'-Modified Nucleoside (5)

[Chemical Formula 45]

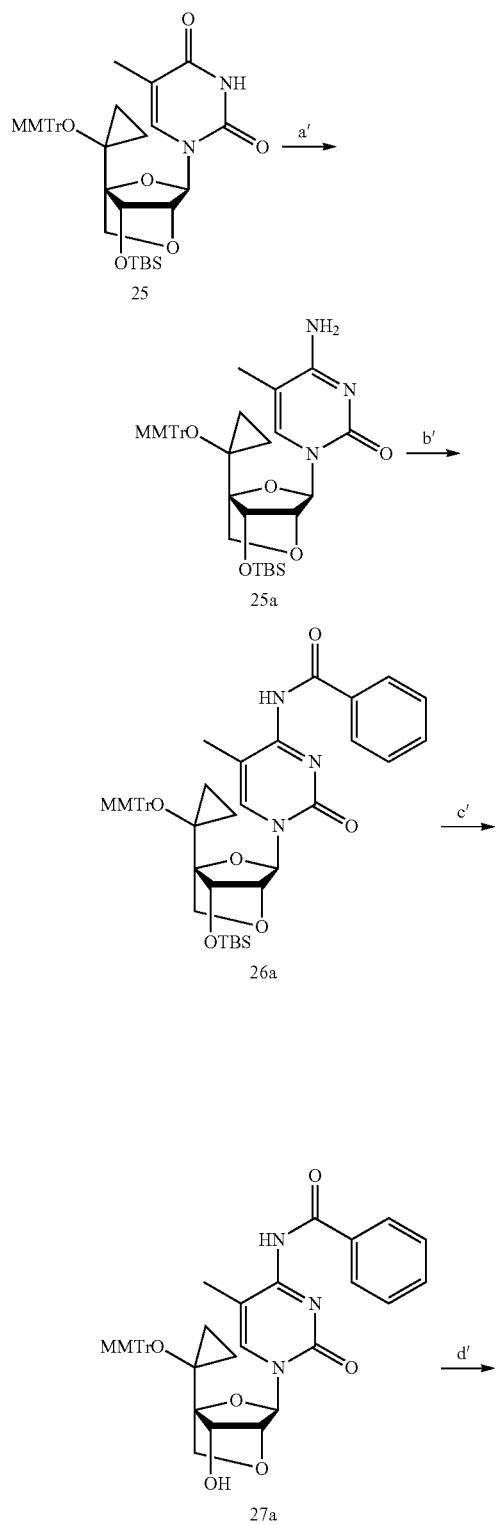

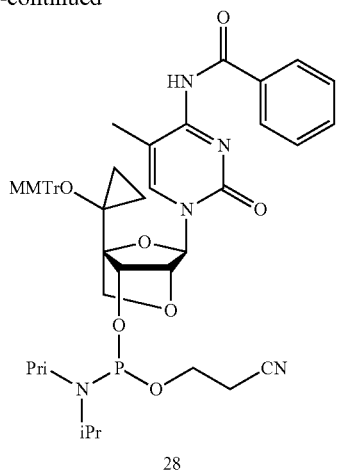

Reagents and conditions under each step: (a') 1,2,4-triazole, POCl₃, TEA, MeCN, r.t., 40 minutes; saturated NH₃ aq., 1,4-dioxane, r.t., 4 hours, 94%; (b') BzCl, pyridine, 0° C., 40 minutes, 79%; (c') TBAF, THF, r.t., 1 hours, 89%; (d') iPr₂NP(Cl)OCH₂·CH₂CN, DIPEA, MeCN, r.t., 3 hours, 44%.

(5-1) Synthesis of Compound 25a

[Chemical Formula 46]

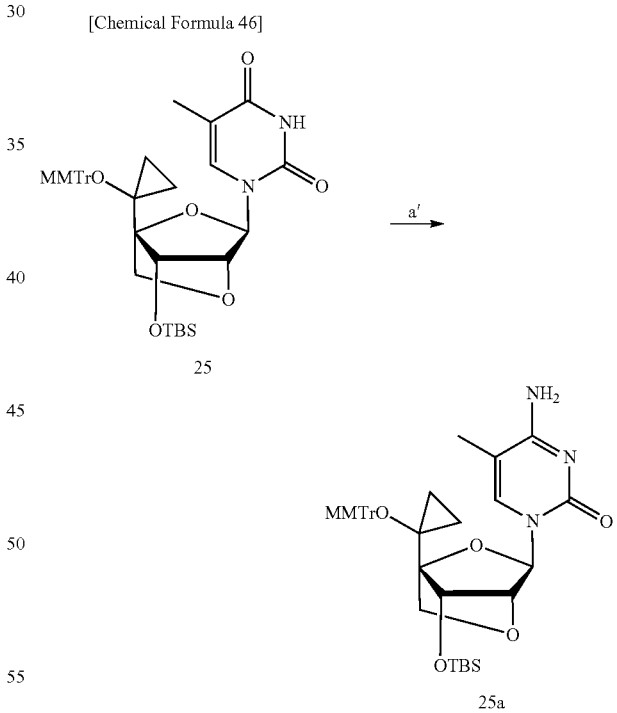

Under nitrogen stream, to a mixed solution of the compound 25 (838 mg, 1.23 mmol) obtained above, triethylamine (2.6 mL, 18.7 mmol), 1,2,4-triazole (1.28 g, 18.5 mmol), and an anhydrous acetonitrile solution (12.5 mL) was added at 0° C. phosphoryl chloride (340 μL, 3.73 mmol). The mixture was stirred at room temperature for 40 minutes, and then, 1,4-dioxane (12.5 mL) and 28% aqueous ammonia (3.7 mL) were added successively to the reaction solution, followed by stirring at room temperature for 4 hours. After completion of the reaction, the reaction liquid was distilled away under reduced pressure. The residue was diluted with ethyl acetate, washed with water/saturated saline (1:1) and saturated saline, and then dried over anhydrous sodium sulfate, and the solvent was distilled away under reduced pressure. The resultant residue was purified by silica-gel column chromatography (SiO$_2$, methanol/chloroform=0% to 3%) to afford a compound 25a (788 mg, 94%) as a light yellow solid.

Table 24 shows data on the properties of the obtained compound 25a.

TABLE 24

Physical property data of the obtained compound 25a $^1$H NMR (300 MHz, CDCl$_3$) δ −0.04 (s, 3H), 0.01 (s, 3H), 0.52-0.59 (m, 1H), 0.85 (s, 9H), 0.96-1.07 (m, 3H), 1.79 (s, 3H), 3.48 (s, 1H), 3.60 (d, J = 8.3 Hz, 1H), 3.62 (d, J = 8.3 Hz, 1H), 3.75 (s, 3H), 4.34 (s, 1H), 5.29 (s, 1H), 6.78 (d, J = 9.2 Hz, 2H), 7.17-7.48 (m, 13H); $^{13}$C NMR (76 MHz, CDCl$_3$) δ −5.0, −4.3, 11.1, 11.4, 13.4, 18.0, 25.7, 55.2, 57.4, 72.2, 72.5, 79.5, 87.2, 87.6, 91.3, 101.0, 112.9, 127.1, 127.7, 128.9, 131.3, 136.5, 137.4, 145.9, 146.0, 155.6, 158.8, 166.0; IR (KBr): 3084, 3013, 2950, 1664, 1611, 1504, 1254, 1058, 857, 756 cm$^{-1}$; [α]$_D^{18}$ 96.57 (c 1.00, CHCl$_3$); HRMS(MALDI) Calculated for C$_{39}$H$_{47}$N$_3$O$_6$NaSi [M + Na]$^+$: 704.3132, Found: 704.3123

(5-2) Synthesis of Compound 26a

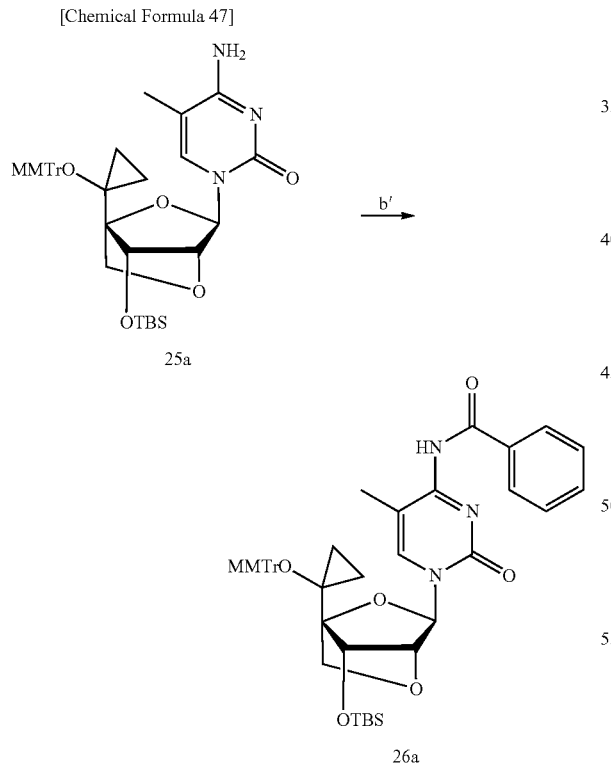

Under nitrogen stream, to an anhydrous pyridine solution (10.7 mL) of the compound 25a (728 mg, 1.07 mmol) obtained above was added at 0° C. benzoyl chloride (190 μL, 1.64 mmol), and the mixture was stirred at 0° C. for 40 minutes. After completion of the reaction, water was added, followed by extraction with ethyl acetate. The organic layer was washed with water, followed by distillation of the solvent under reduced pressure and azeotroped with toluene. The resultant residue was purified by silica-gel column chromatography (SiO$_2$, ethyl acetate/hexane=4% to 25%) to afford a compound 26a (664 mg, 79%) as a white solid.

Table 25 shows data on the properties of the obtained compound 26a.

TABLE 25

Physical property data of the obtained compound 26a $^1$H NMR (300 MHz, CDCl$_3$) δ 0.01 (s, 3H), 0.04 (s, 3H), 0.55-0.60 (m, 1H), 0.88 (s, 9H), 0.89-1.09 (m, 3H), 2.02 (s, 3H), 3.49 (s, 1H), 3.65 (s, 2H), 3.77 (s, 3H), 4.32 (s, 1H), 5.23 (s, 1H), 6.80 (d, J = 8.7 Hz, 2H), 7.19-7.53 (m, 15H), 8.09-8.12 (m, 1H), 8.29-8.33 (m, 2H); $^{13}$C NMR (76 MHz, CDCl$_3$) δ −5.0, −4.3, 11.3, 11.7, 13.9, 18.0, 25.7, 55.3, 57.1, 72.3, 72.6, 79.3, 87.2, 87.8, 91.8, 111.1, 112.9, 127.2, 127.7, 127.9, 128.3, 128.5, 128.9, 130.0, 130.3, 131.3, 132.6, 133.7, 136.3, 136.5, 137.0, 145.8, 145.9, 147.5, 158.8, 159.9, 179.5; IR (KBr): 2948, 1705, 1568, 1254, 1173, 1057, 856, 756 cm$^{-1}$; [α]$_D^{18}$ 113.69 (c 1.00, CHCl$_3$); HRMS(MALDI) Calculated for C$_{46}$H$_{51}$N$_3$O$_7$NaSi [M + Na]$^+$: 808.3388, Found: 808.3386

(5-3) Synthesis of Compound 27a

[Chemical Formula 48]

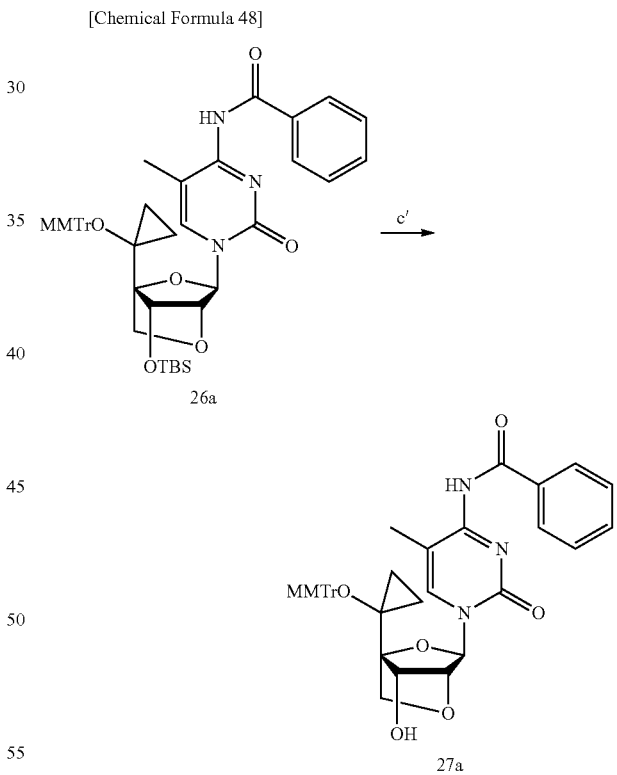

To a tetrahydrofuran solution (850 μL, 0.85 mmol) of the compound 26a (611 mg, 0.78 mmol) obtained above was added at 0° C. a tetrahydrofuran solution (855 μL, 0.86 mmol) of 1.0 M tetrabutylammonium fluoride (TBAF), and the mixture was stirred at room temperature for an hour. After completion of the reaction, the reaction solution was distilled away under reduced pressure, followed by dilution with ethyl acetate. The solution was washed with water and saturated saline and then dried over anhydrous sodium sulfate, and the solvent was distilled away under reduced pressure. The resultant residue was purified by silica-gel column chromatography (SiO$_2$, ethyl acetate/hexane=30% to 50%) to afford a compound 27a (464 mg, 89%) as a white solid.

Table 26 shows data on the properties of the obtained compound 27a.

TABLE 26

Physcial property data of the obtained compound 27a $^1$H NMR (300 MHz, CDCl$_3$) δ 0.70-0.77 (m, 1H), 1.02-1.30 (m, 3H), 1.77 (d, J = 7.3 Hz, 1H), 1.97 (s, 3H), 3.26 (d, J = 6.9 Hz, 1H), 3.69 (d, J = 8.7 Hz, 1H), 3.73 (d, J = 9.2 Hz, 1H), 3.77 (s, 3H), 4.26 (s, 1H), 5.29 (s, 1H), 6.83 (d, J = 9.2 Hz, 2H), 7.21-7.56 (m, 16H), 8.30 (d, J = 7.3 Hz, 2H), 13.34 (bs, 1H); $^{13}$C NMR (76 MHz, CDCl$_3$) δ 11.6, 11.7, 13.7, 55.3, 56.7, 71.6, 72.3, 80.0, 86.4, 87., 91.4, 111.1, 113.1, 127.3, 127.9, 128.2, 128.7, 128.8, 130.0, 131.1, 132.6, 135.8, 136.5, 137.1, 145.8, 145.8, 147.4, 158., 159.7, 179.7; IR (KBr): 3440, 3065, 3021, 2956, 1703, 1568, 1354, 1251, 1046, 755, 708 cm$^{-1}$; [α]$_D$$^{18}$ 80.80 (c 1.00, CHCl$_3$) ; HRMS(MALDI) Calculated for C$_{40}$H$_{37}$N$_3$O$_7$Na [M + Na] $^+$: 694.2529, Found: 694.2525

(5-4) Synthesis of Compound 28

[Chemical Formula 49]

mixture was stirred at room temperature for 3 hours. After completion of the reaction, the reaction solution was distilled away under reduced pressure. The resultant residue was purified by silica-gel column chromatography (SiO$_2$, ethyl acetate/hexane=20% to 41%) to afford a compound 28 (236 mg, 44%) as a white solid.

Table 27 shows data on the properties of the obtained compound 28.

TABLE 27

Physical property data of the obtained compound 28

$^1$H NMR (300 MHz, CDCl$_3$) δ 0.66-0.76 (m, 1H), 1.13-1.24 (m, 15H), 2.03 (d, J = 0.9 Hz, 1.5H), 2.05 (d, J = 0.9 Hz, 1.5H), 2.46-2.60 (m, 2H), 3.46-3.81 (m, 7H), 3.76 (s, 3H), 4.58 (s, 1H), 5.21 (s, 0.5H), 5.23 (s, 0.5H), 6.80 (d, J = 9.2 Hz, 2H), 7.18-7.55 (m, 16H), 8.32 (d, J = 7.3 Hz, 2H), 13.34 (bs, 1H); $^{31}$P NMR (121.7 MHz, CDCl$_3$) δ 148.5, 149.0; HRMS(MALDI) Calculated for C$_{49}$H$_{54}$N$_5$O$_8$PNa [M + Na] $^+$: 894.3608, Found: 894.3604

Example 6

Synthesis of 5'-Modified Nucleoside (6)

[Chemical Formula 50]

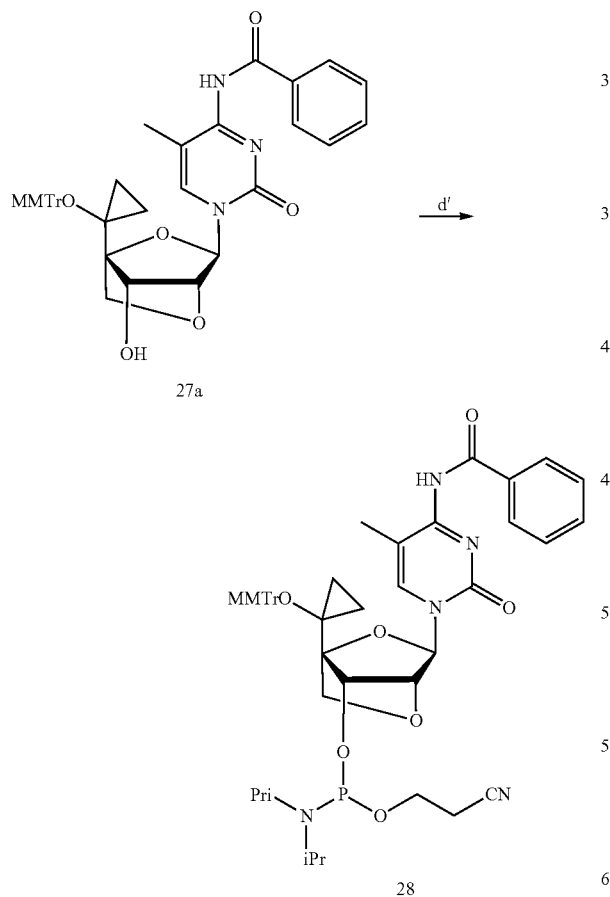
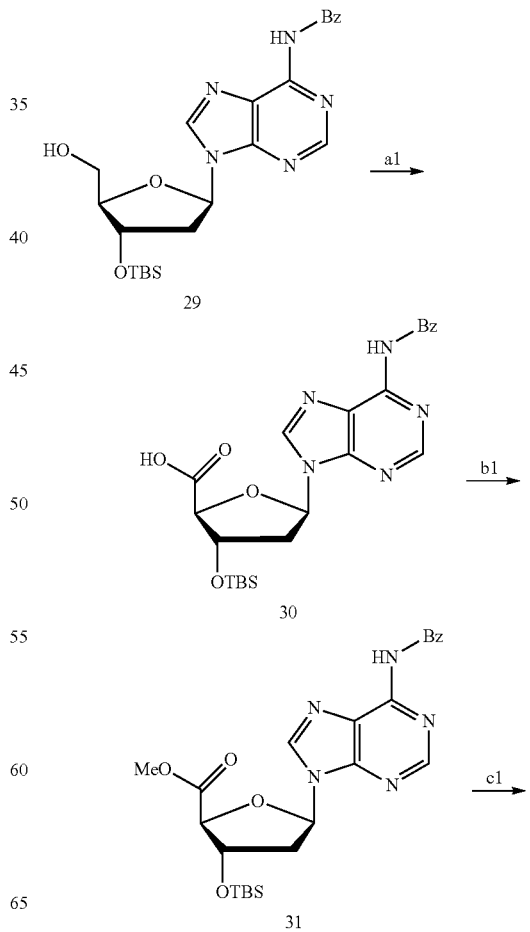

Under nitrogen stream, to an anhydrous acetonitrile solution (6.1 mL) of the compound 27a (410 mg, 0.61 mmol) obtained above were added at 0° C. N,N-diisopropylethylamine (420 μL, 2.46 mmol) and 2-cyanoethyl-N,N-diisopropyl phosphorochloridate (270 μL, 1.21 mmol), and the -continued

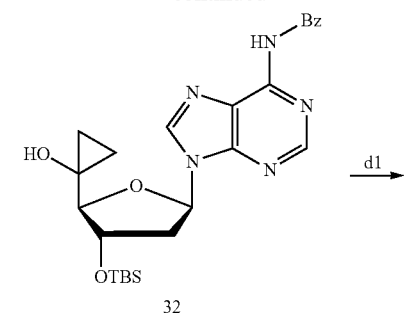
32

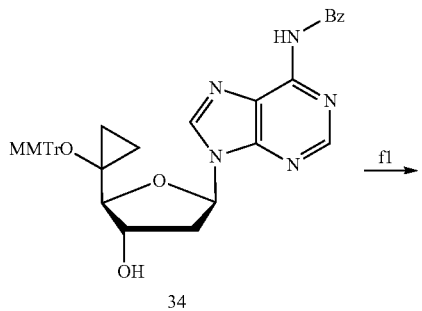
33

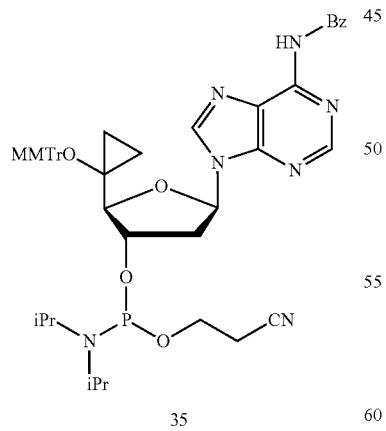
34

35

Reagents and conditions under each step: (a1) TEMPO, PhI(OAc)₂, CH₂Cl₂, r.t., 2 hours; MeCN, H₂O, r.t., 12 hours; (b1) EDC•HCl, MeOH, CH₂Cl₂, 0° C., 3 hours, 71% (2steps); (c1) EtMgBr, Ti(OiPr)₄, THF, 0° C., to r.t., 5 hours, 23%; (d1) MMTrCl, AgNO₃, pyridine, THF, 50° C., 6 hours, 62%; (e1) TBAF, THF, r.t., 12 hours, 86%; (f1) iPr₂NP(Cl)OCH₂CH₂CN, DIPEA, MeCN, r.t., 3 hours, 69%.

(6-1) Synthesis of Compound 30

[Chemical Formula 51]

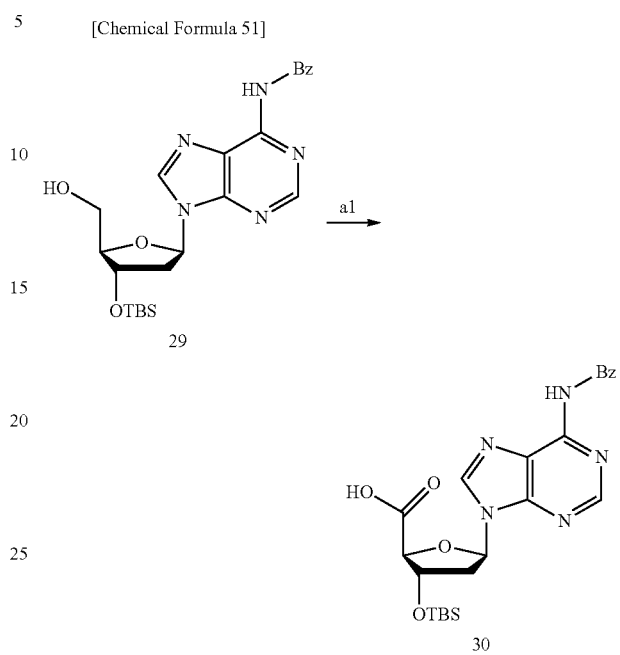

To a dichloromethane solution (17 mL) of a compound 29 (1.60 g, 3.41 mmol), the compound 29 being prepared using a known method (Suzuki et al., Biomacromolecules, 2011, Vol. 12, No. 5, pp. 1449-1459), were added sequentially at 0° C. iodobenzene diacetate (2.41 g, 7.48 mmol) and 2,2,6,6-tetramethylpiperidine 1-oxyl free radical (123 mg, 0.79 mmol), and the mixture was stirred at room temperature for 2 hours. After that, acetonitrile/water (=1:1 (volume ratio), 200 µL) was added, and the mixture was stirred at room temperature for additional 12 hours. After completion of the reaction, an excess of methanol was added to the mixture, and the mixture was stirred at room temperature for 10 minutes, followed by distillation of the solvent under reduced pressure and azeotroped with toluene, to afford a compound 30 as a yellow solid. The compound 30 was immediately used for the next reaction without purification.

(6-2) Synthesis of Compound 31

[Chemical Formula 52]

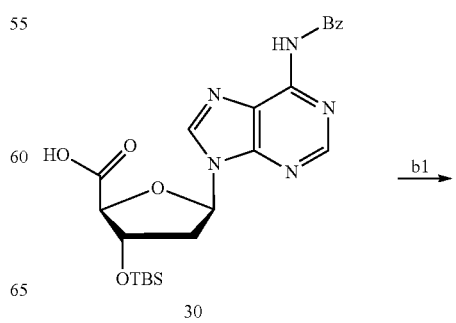
30

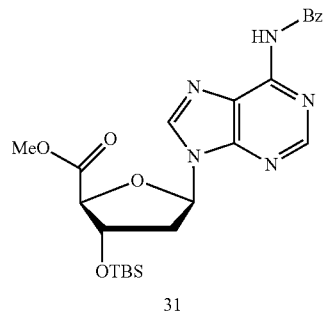

31

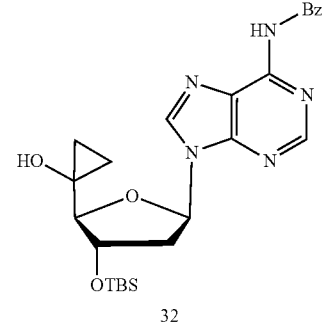

32

To a dichloromethane solution (17 mL) of the compound 30 obtained above were added sequentially methanol (1.50 mL, 36 mmol) and 1-(3-dimethylaminopropyl)-3-ethylcarbodiimide hydrochloride (1.57 g, 8.2 mmol), and the mixture was stirred at 0° C. for 3 hours. After completion of the reaction, water was added, followed by extraction with ethyl acetate. The organic layer was washed with water and saturated saline and then dried over anhydrous sodium sulfate, and the solvent was distilled away under reduced pressure. The resultant residue was purified by silica-gel column chromatography (SiO₂, hexane/ethyl acetate=50%) to afford a compound 31 (1.21 g, yield: 71%, 2 steps) as a white solid.

Table 28 shows data on the properties of the obtained compound 31.

TABLE 28

| Physical property data of the obtained compound 31 |
|---|
| $^1$H NMR (300 MHz, CDCl$_3$) δ 0.16 (s, 6H), 0.95 (s, 9H), 2.52-2.57 (m, 2H), 3.81 (s, 3H), 4.58 (s, 1H), 4.71-4.74 (m, 1H), 6.76 (dd, J = 7.1, 7.1 Hz, 1H), 7.53 (t, J = 7.4 Hz, 2H), 7.62 (t, J = 7.3 Hz, 1H), 8.04 (d, J = 6.9 Hz, 2H), 8.73 (s, 1H), 8.82 (s, 1H), 9.02 (s, 1H); $^{13}$C NMR (126 MHz, CDCl$_3$) δ −5.0, 18.0, 25.6, 41.2, 52.6, 75.8, 85.7, 123.0, 127.8, 128.8, 132.7, 133.7, 142.0, 149.4, 151.6, 152.6, 164.6, 171.3; HRMS(MALDI) Calculated for C$_{24}$H$_{31}$N$_5$ONaSi [M + Na] $^+$: 520.1992 Found: 520.1994 |

Under nitrogen stream, to an anhydrous tetrahydrofuran solution (120 mL) of the compound 31 (5.98 g, 12.0 mmol) obtained above and titanium tetraisopropoxide (4.0 mL, 15 mmol) was added dropwise at 0° C. over 15 minutes a tetrahydrofuran solution (60 mL, 60 mmol) of 1.0 M ethyl magnesium bromide. After the dropwise addition, the reaction solution was warmed to room temperature and stirred for additional 5 hours. After completion of the reaction, Celite filtration was performed after a saturated aqueous solution of ammonium chloride was added thereto, and the filtrate was extracted with ethyl acetate. The organic layer was washed with water and saturated saline and then dried over anhydrous sodium sulfate, and the solvent was distilled away under reduced pressure. The resultant residue was purified by silica-gel column chromatography (SiO₂, acetone/chloroform=10% to 15%) to afford a compound 32 (1.40 g, yield: 23%) as a yellow solid.

Table 29 shows data on the properties of the obtained compound 32.

TABLE 29

| Physical property data of the obtained compound 32 |
|---|
| $^1$H NMR (500 MHz, CDCl$_3$) δ 0.10 (s, 3H), 0.11 (s, 3H), 0.59-0.64 (m, 2H), 0.84-0.87 (m, 2H), 0.90 (s, 9H), 2.23 (dd, J = 5.8, 13 Hz, 1H), 3.10-3.15 (m, 1H), 3.50 (s, 1H), 4.87 (d, J = 4.6 Hz, 1H), 6.35 (dd, J = 5.4, 9.6 Hz, 1H), 6.86 (s, 1H), 7.46 (t, J = 7.7 Hz, 2H), 7.56 (t, J = 7.3 Hz, 1H), 8.00 (d, J = 7.6 Hz, 2H), 8.07 (s, 1H), 8.68 (s, 1H), 9.37 (s, 1H); $^{13}$C NMR (126 MHz, CDCl$_3$) δ −4.9, −4.8, 10.1, 13.2, 25.5, 25.7, 25.8, 40.7, 55.3, 74.6, 87.6, 96.0, 124.7, 127.9, 128.7, 132.8, 133.4, 142.7, 149.4, 150.5, 151.8, 164.7; HRMS(MALDI) Calculated for C$_{25}$H$_{33}$N$_5$O$_4$NaSi [M + Na] $^+$: 518.2200, Found: 518.2194 |

(6-3) Synthesis of Compound 32

[Chemical Formula 53]

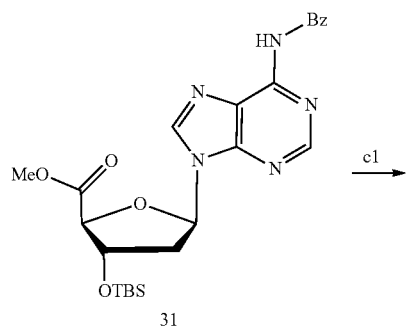

31 →c1

(6-4) Synthesis of Compound 33

[Chemical Formula 54]

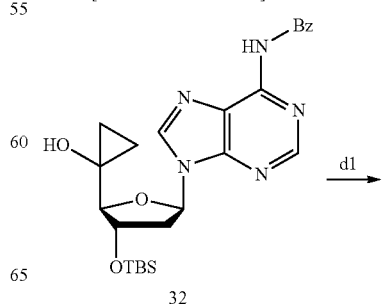

32 →d1

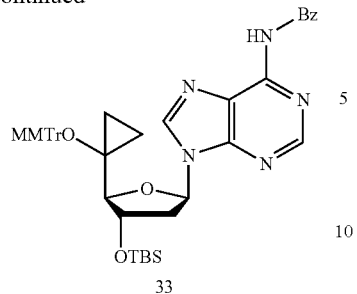

33

Under nitrogen stream, to an anhydrous pyridine/tetrahydrofuran mixed solution (=1:4 (volume ratio), 70 mL) of the compound 32 (890 mg, 1.8 mmol) obtained above were added sequentially 4-methoxytrityl chloride (2.9 g, 94 mmol) and silver nitrate (1.4 g, 8.3 mmol), and the mixture was stirred at 50° C. for 6 hours. After completion of the reaction, Celite filtration was performed after saturated sodium hydrogen carbonate was added thereto, and the filtrate was extracted with ethyl acetate. The organic layer was washed with water and saturated saline and then dried over anhydrous sodium sulfate, and the solvent was distilled away under reduced pressure. The resultant residue was purified by silica-gel column chromatography (SiO$_2$, containing 1% triethylamine, ethyl acetate/hexane=100%→methanol/chloroform=0%→>10%) to afford a compound 33 (849 mg, yield: 62%) as a yellow solid.

Table 30 shows data on the properties of the obtained compound 33.

TABLE 30

Physical property data of the obtained compound 33

$^1$H NMR (500 MHz, CDCl$_3$) δ 0.04 (s, 3H), 0.11 (s, 3H), 0.49-0.53 (m, 1H), 0.65-0.70(m, 1H), 0.87 (s, 9H), 0.90-0.94 (m, 2H), 2.31-2.34 (m, 1H), 2.63-2.70 (m, 1H), 3.03 (d, J = 2.0 Hz, 1H), 3.80 (s, 3H), 4.62-4.63 (m, 1H), 6.12 (dd, J = 5.3, 8.7 Hz, 1H), 6.81 (d, J = 8.9 Hz, 2H), 7.20-7.24 (m, 4H), 7.25-7.26 (m, 1H), 7.26-7.27 (m, 1H), 7.33-7.36 (m, 2H), 7.43-7.47 (m, 4H), 7.51 (t, J = 7.6 Hz, 2H), 7.59 (t, J = 7.5 Hz, 1H), 8.01 (d, J = 7.2 Hz, 2H), 8.08 (s, 1H), 8.77 (s, 1H), 9.05 (s, 1H); $^{13}$C NMR (126 MHz, CDCl$_3$) δ −4.7, −4.2, 9.0, 9.4, 17.7, 40.5, 55.2, 58.8 73.3, 84.6, 87.2, 87.5, 112.9, 123.5, 127.0, 127.7, 128.7, 132.7, 133.6, 136.3, 141.5, 146.0, 149.4, 151.6, 152.6, 158.7, 164.5; HRMS(MALDI) Calculated for C$_{45}$H$_{49}$N$_5$O$_5$NaSi [ M + Na ] $^+$: 790.3401, Found: 790.3399

(6-5) Synthesis of Compound 34

[Chemical Formula 55]

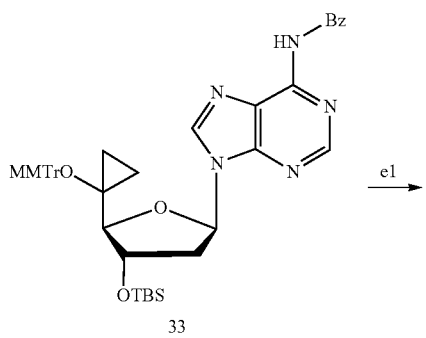

33 → e1

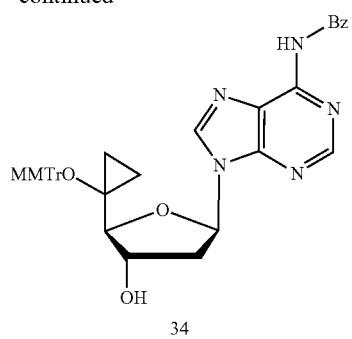

34

To a tetrahydrofuran solution (24 mL) of the compound 33 (783 mg, 1.0 mmol) obtained above was added at 0° C. a tetrahydrofuran solution (2.40 mL, 2.40 mmol) of 1.0 M tetrabutylammonium fluoride (TBAF), and the mixture was stirred at room temperature for 12 hours. After completion of the reaction, the reaction liquid was distilled away under reduced pressure, and water was added, followed by extraction with ethyl acetate. The organic layer was washed with saturated saline and then dried over anhydrous sodium sulfate, and the solvent was distilled away under reduced pressure. The resultant residue was purified by silica-gel column chromatography (SiO$_2$, containing 1% triethylamine, acetone/chloroform=20% to 25% to afford a compound 34 (574 mg, yield: 86%) as a white solid.

Table 31 shows data on the properties of the obtained compound 34.

TABLE 31

Physical property data of the obtained compound 34

$^1$H NMR (500 MHz, CDCl$_3$) δ 0.43-0.46 (m, 1H), 0.65-0.68 (m, 1H), 0.88 (t, J = 6.9 Hz, 2H), 2.10 (s, 1H), 2.33-2.38 (m, 1H), 2.83 (s, 2H), 3.80 (s, 3H), 4.86-4.87 (m, 1H), 6.07 (dd, J = 6.9 Hz, 1H), 6.84 (d, 1H), 7.22-7.25 (m, 2H), 7.27-7.31 (m, 4H), 7.35-7.37 (m, 2H), 7.45-7.47 (m, 4H), 7.49-7.50 (m, 2H), 7.57 (t, J = 7.6Hz, 1H), 7.95 (s, 1H), 8.00 (d, J = 7.7Hz, 2H), 8.75 (s, 1H), 9.16 (s, 1H); $^{13}$C NMR (126 MHz, CDCl$_3$) δ 8.4, 9.8, 38.8, 55.2, 59.9, 73.3, 83.5, 84.6, 87.5, 113.1, 123.4, 127.2, 127.9, 128.4, 128.8, 130.9, 132.7, 133.5, 136.1, 141.4, 145.9, 149.5, 151.5, 152.6, 158.9, 164.6; HRMS(MALDI) Calculated for C$_{39}$H$_{35}$N$_5$O$_5$Na [M + Na] $^+$: 676.2536, Found: 676.2553

(6-6) Synthesis of Compound 35

[Chemical Formula 56]

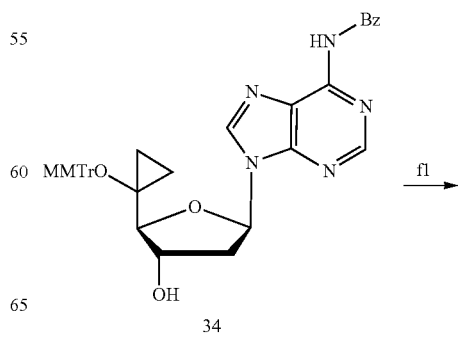

34 → f1

-continued

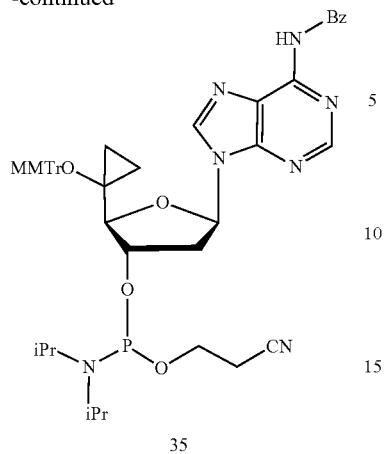

35

Under nitrogen stream, to an anhydrous acetonitrile solvent (1.5 mL) of the compound 34 (98 mg, 0.15 mmol) obtained above were added sequentially N,N-diisopropylethylamine (DIPEA; 80 μL) and 2-cyanoethyl-N,N-diisopropyl phosphorochloridate (iPr$_2$NP(Cl)OCH$_2$CH$_2$CN; 55 μL), and the mixture was stirred at room temperature for 3 hours. After completion of the reaction, the solvent was distilled away under reduced pressure, and the resultant residue was purified by silica-gel column chromatography (SiO$_2$, ethyl acetate/hexane=150%). Finally, reprecipitation (ethyl acetate/hexane) was performed to afford a compound 35 (88 mg, yield: 69%) as a white solid.

Table 32 shows data on the properties of the obtained compound 35.

TABLE 32

Physical property data of the obtained compound 35

$^1$H NMR (500 MHz, CDCl$_3$) δ 0.52-0.55 (m, 1H), 0.76-0.79 (m, 1H), 0.88-0.96 (m, 2H), 1.12-1.26 (m, 12H), 2.43-2.47 (m, 1H), 2.57-2.69 (m, 2H), 2.72-2.78 (m, 1H), 3.56-3.62 (m, 2H), 3.80 (s, 1H), 3.81 (s, 2H), 4.88-4.92 (m, 1H), 6.08-6.13 (m, 1H), 6.80 (d, J = 8.4 Hz, 0.6H), 6.82 (d, J = 9.2 Hz 1.4H), 7.21-7.24 (m, 4H), 7.27-7.29 (m, 2H), 7.33-7.37 (m, 2H), 7.43-7.47 (m, 4H), 7.51 (t, J = 7.7 Hz, 2H), 7.60 (t, = 7.7 Hz, 1H), 8.00 (d, = 6.9Hz, 2H), 8.04 (s, 1H), 8.75 (s, 0.7H), 8.77 (s, 0.3H), 8.99 (s, 0.7H), 9.00 (s, 0.3H); $^{31}$P NMR (202.5 MHz, CDCl$_3$) 6147.7, 149.7; HRMS(FAB) Calculated for C$_{48}$H$_{53}$N$_7$O$_6$P [M + H]$^+$: 854.3795, Found: 854.3790

Example 7

Synthesis of 5'-Modified Nucleoside (7)

[Chemical Formula 57]

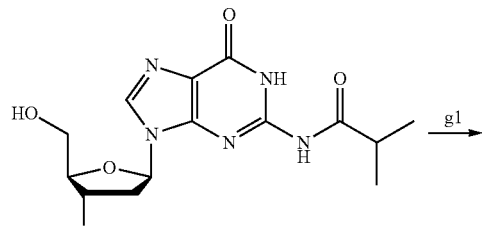

36

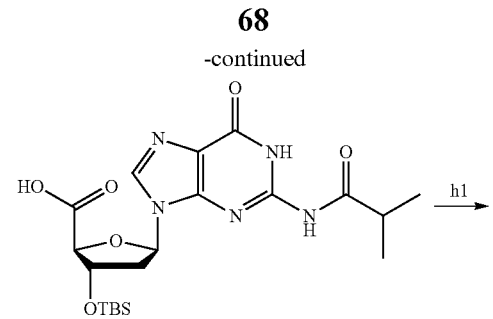

37

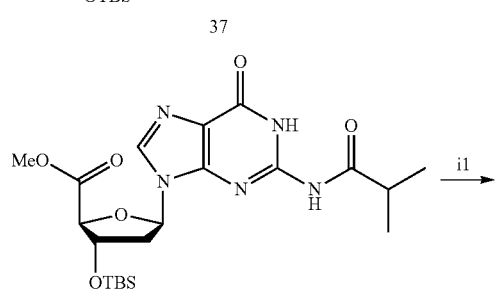

38

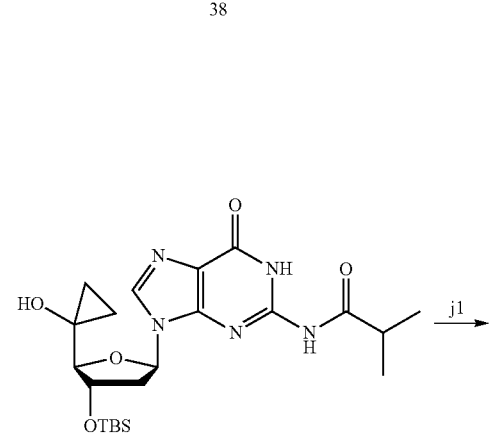

39

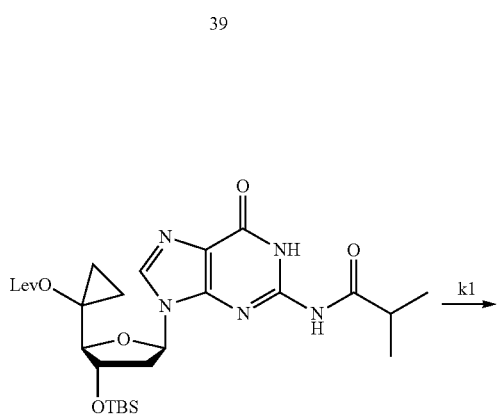

40

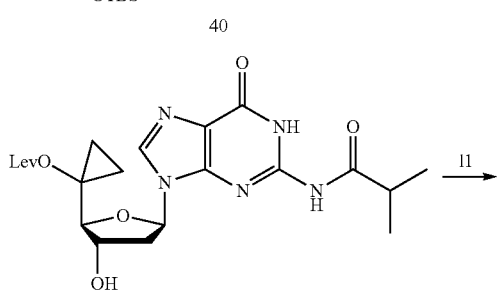

41

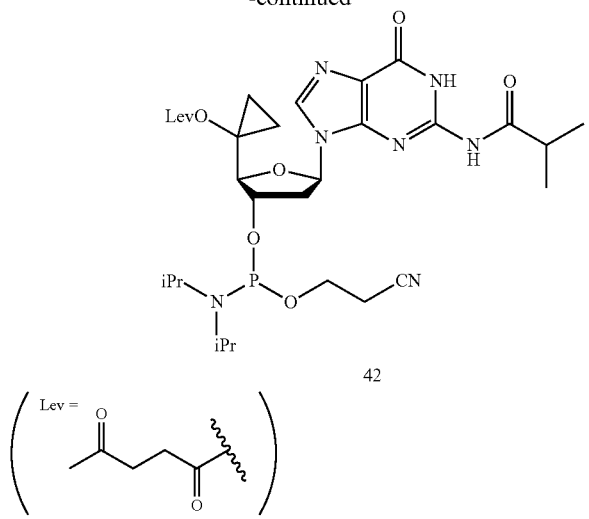

Reagents and conditions under each step: (g1) TEMPO, PhI(OAc)₂, CH₂Cl₂, r.t., 2 hours; MeCN, H₂O, r.t., 14 hours; (h1) EDC·HCl, MeOH, CH₂Cl₂, 0° C., 2 hours, 74% (2 steps); (i1) EtMgBr, Ti(OiPr)₄, THF, 0° C. to r.t., 7 hours, 35%; (j1) LevOH, EDC·HCl, DMAP, DIPEA, THF, r.t., 25 hours, 78%; (k1) TBAF, THF, r.t., 16 hours, 62%; (l1) iPr₂NP(Cl)OCH₂CH₂CN, DIPEA, MeCN, r.t., 3 hours, 73%.

(7-1) Synthesis of Compound 37

[Chemical Formula 58]

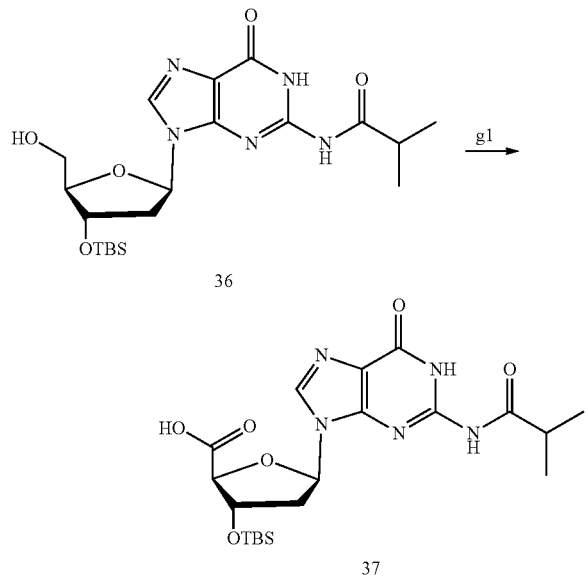

To a dichloromethane solution (300 mL) of a compound 36 (28.3 g, 63 mmol), the compound 36 being prepared using a known method (Wexsellblatt et al., Bioorg. Med. Chem., 2010, Vol. 18, No. 12, pp. 4485-4497), were added sequentially at 0° C. iodobenzene diacetate (44.8 g, 140 mmol) and 2,2,6,6-tetramethylpiperidine 1-oxyl free radical (2.5 g, 16 mmol), and the mixture was stirred at room temperature for 2 hours. After that, acetonitrile/water (=1:1 (volume ratio), 8.0 mL) was added, and the mixture was stirred at room temperature for additional 14 hours. After completion of the reaction, an excess of methanol was added to the mixture, and the mixture was stirred at room temperature for 10 minutes, followed by distillation of the solvent under reduced pressure and azeotroped with toluene, to afford a compound 37 as a yellow solid. The compound 37 was immediately used for the next reaction without purification.

(7-2) Synthesis of Compound 38

[Chemical Formula 59]

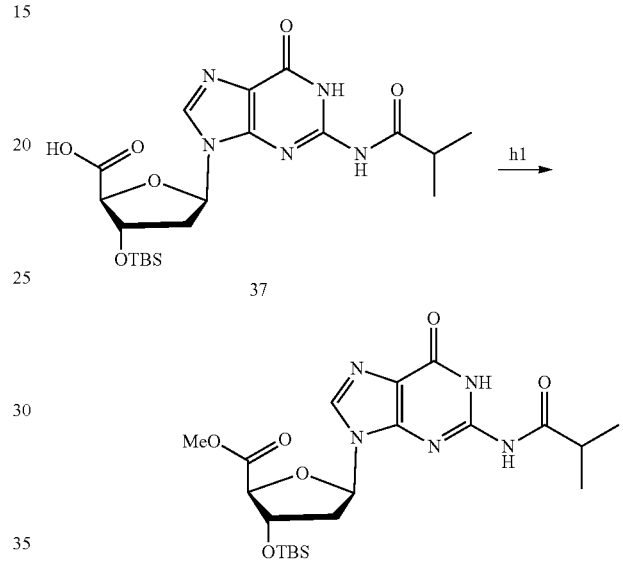

To a dichloromethane solution (40 mL) of the compound 37 obtained above were added sequentially methanol (30 mL, 740 mmol) and 1-(3-dimethylaminopropyl)-3-ethylcarbodiimide hydrochloride (19 g, 99 mmol), and the mixture was stirred at 0° C. for 2 hours. After completion of the reaction, water was added, followed by extraction with ethyl acetate. The organic layer was washed with water and saturated saline and then dried over anhydrous sodium sulfate, and the solvent was distilled away under reduced pressure. The resultant residue was purified by silica-gel column chromatography (SiO₂, methanol/chloroform=10%) to afford a compound 38 (22.2 g, yield: 74%, 2 steps) as a white solid.

Table 33 shows data on the properties of the obtained compound 38.

TABLE 33

Physical property data of the obtained compound 38

$^1$H NMR (500 MHz, CDCl₃) δ 0.08 (s, 3H), 0.10 (s, 3H), 0.86 (s, 9H), 1.20 (d, J = 6.9 Hz, 3H), 1.23 (d, J = 6.9 Hz, 3H), 2.39-2.45 (m, 2H), 2.71-2.76 (m, 1H), 3.73 (s, 3H), 4.43 (d, J = 2.3 Hz, 1H), 4.63 (s, 1H), 6.38 (dd, J = 7.1, 7.1 Hz, 1H), 8.25 (s, 1H), 9.37 (s, 1H), 12.10 (s, 1H); $^{13}$C NMR (126 MHz, CDCl₃) δ −5.1, −5.0, 17.9, 18.9, 19.0, 25.5, 36.3, 40.9, 52.5, 75.5, 84.9, 85.5, 120.9, 137.5, 147.7, 148.2, 155.6, 171.0, 178.9; HRMS(MALDI) Calculated for C₂₁H₃₃N₅O₆NaSi [M + Na] $^+$: 502.2098 Found: 502.2074

(7-3) Synthesis of Compound 39

[Chemical Formula 60]

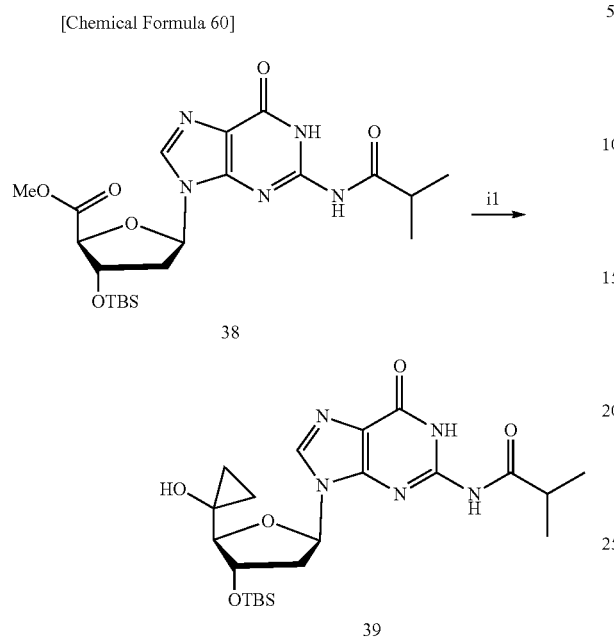

(7-3) Synthesis of Compound 40

[Chemical Formula 61]

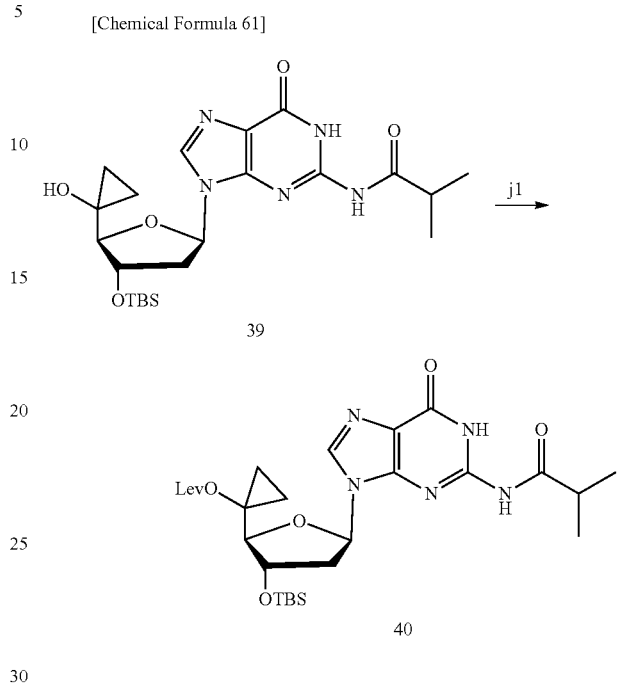

Under nitrogen stream, to an anhydrous tetrahydrofuran solution of the compound 38 (6.02 g, 12 mmol) obtained above and titanium tetraisopropoxide (4.0 mL, 14.7 mmol) was added dropwise at 0° C. over 15 minutes a tetrahydrofuran solution (60 mL, 60 mmol) of 1.0 M ethyl magnesium bromide. After the dropwise addition, the reaction solution was warmed to room temperature and stirred for additional 7 hours. After completion of the reaction, Celite filtration was performed after a saturated aqueous solution of ammonium chloride was added thereto, and the filtrate was extracted with ethyl acetate. The organic layer was washed with water and saturated saline and then dried over anhydrous sodium sulfate, and the solvent was distilled away under reduced pressure. The resultant residue was purified by silica-gel column chromatography ($SiO_2$, acetone/chloroform=20% to 25%) to afford a compound 39 (2.08 g, yield: 35%) as a yellow solid.

Table 34 shows data on the properties of the obtained compound 39.

Under nitrogen stream, to an anhydrous dichloromethane solution (12.5 mL) of the compound 39 (256 mg, 0.54 mmol) obtained above and levulinic acid (937 mg, 8.1 mmol) were added sequentially 1-(3-dimethylaminopropyl)-3-ethylcarbodiimide hydrochloride (524 mg, 2.7 mmol), N,N-dimethylaminopyridine (93 mg, 0.72 mmol), and N,N-diisopropylethylamine (560 µL, 3.2 mmol), and the mixture was stirred for 25 hours. After completion of the reaction, water was added, and the reaction liquid was extracted with chloroform. The organic layer was washed with water and saturated saline and then dried over anhydrous sodium sulfate, and the solvent was distilled away under reduced pressure. The resultant residue was purified by silica-gel column chromatography ($SiO_2$, acetone/chloroform=20% and methanol/chloroform=10%) to afford a compound 40 (239 mg, yield: 78%) as a brown solid.

Table 35 shows data on the properties of the obtained compound 40.

TABLE 34

Physical property data of the obtained compound 39

$^1$H NMR (500 MHz, $CDCl_3$) δ 0.09 (s, 3H), 0.10 (s, 3H), 0.61-0.69 (m, 2H), 0.81-0.87 (m, 2H), 0.89 (s, 9H), 1.21 (d, J = 5.4 Hz, 3H), 1.23 (d, J = 5.5 Hz, 3H), 2.21-2.25 (m, 1H), 2.64-2.70 (s, 1H), 2.88 (m, 1H), 3.42-3.43 (m, 1H), 4.79-4.80 (m, 1H), 5.91 (s, 1H), 6.17 (dd, J = 8.9, 5.7 Hz, 1H), 7.80 (s, 1H), 8.74 (s, 1H), 12.04 (s, 1H); $^{13}$C NMR (126 MHz, $CDCl_3$) δ −4.8, −4.7, 9.6, 13.5, 18.0, 18.9, 25.7, 36.4, 40.9, 55.5, 74.1, 86.5, 94.9, 122.7, 138.8, 147.0, 147.4, 155.2, 178.7; HRMS (MALDI) Calculated for $C_{22}H_{35}N_5O_5NaSi$ [M + Na]$^+$: 500.2305, Found: 500.2291

TABLE 35

Physical property data of the obtained compound 40

$^1$H NMR (500 MHz, $CDCl_3$) δ 0.84-0.89 (m, 1H), 0.91 (s, 9H), 0.96-1.06 (m, 3H), 1.27 (d, J = 6.9 Hz, 3H), 1.27 (d, J = 6.9 Hz, 3H), 2.19 (s, 3H), 2.31-2.41 (m, 2H), 2.51-2.64 (m, 4H), 2.72-2.79 (m, 2H), 3.73 (d, J = 3.5 Hz, 1H), 4.76-4.78 (m, 1H), 6.14 (dd, J = 6.3, 7.5 Hz, 1H), 7.95 (s, 1H) , 8.36 (s, 1H), 11.99 (s, 1H); $^{13}$C NMR (126 MHz, $CDCl_3$) δ −4.7, 0.0, 10.3, 10.9, 17.9, 19.0, 25.7, 28.2, 29.9, 36.6, 37.6, 40.5, 58.1, 72.5, 83.1, 90.6, 121.8, 137.0, 147.3, 155.4, 172.5, 178.0, 207.1; HRMS (MALDI) Calculated for $C_{27}H_{41}N_5O_7NaSi$ [M + Na]$^+$: 598.2673, Found: 598.2651

(7-4) Synthesis of Compound 41

[Chemical Formula 62]

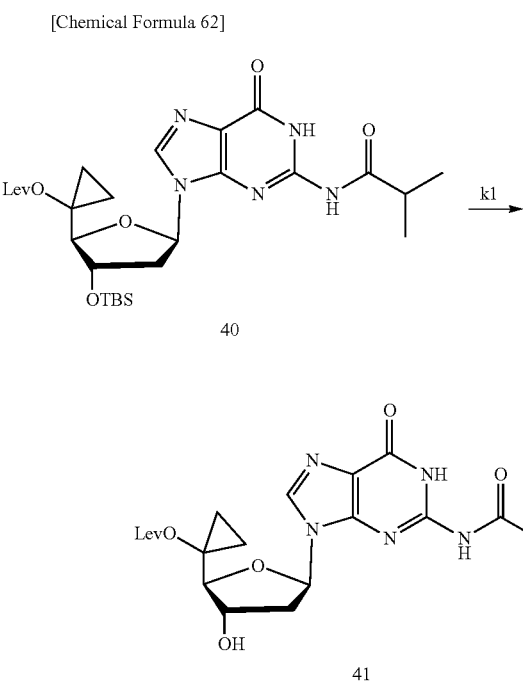

To a tetrahydrofuran solution (5.0 mL) of the compound 40 (148 mg, 0.26 mmol) obtained above was added at 0° C. a tetrahydrofuran solution (350 μL, 0.35 mmol) of 1.0 M tetrabutylammonium fluoride (TBAF), and the mixture was stirred at room temperature for 16 hours. After completion of the reaction, the reaction liquid was distilled away under reduced pressure, and water was added, followed by extraction with ethyl acetate. The organic layer was washed with saturated saline and then dried over anhydrous sodium sulfate, and the solvent was distilled away under reduced pressure. The resultant residue was purified by silica-gel column chromatography (SiO$_2$, methanol/chloroform=10%) to afford a compound 41 (74 mg, yield: 62%) as a white solid.

Table 36 shows data on the properties of the obtained compound 41.

TABLE 36

Physical property data of the obtained compound 41

$^1$H NMR (500 MHz, CDCl$_3$) δ 0.00-0.83 (m, 1H), 0.86-0.92 (m, 2H), 0.94-0.95 (m, 1H), 1.23 (d, J = 6.9 Hz, 3H), 1.26 (d, J = 6.9 Hz, 1H), 2.24 (s, 3H), 2.37-2.50 (m, 2H), 2.59-2.72 (m, 1H), 2.88-2.94 (m, 1H), 3.68 (s, 1H), 3.74 (d, J = 6.3 Hz, 1H), 4.70 (m, 1H), 6.05 (dd, J = 4.6 Hz, 1H), 7.87 (s, 1H), 9.33 (s, 1H), 12.16 (s, 1H); $^{13}$C NMR (126 MHz, CDCl$_3$) δ 9.7, 10.2, 18.9, 19.0, 28.2, 29.8, 36.0, 37.8, 39.4, 58.4, 70.9, 83.0, 87.5, 121.1, 137.8, 148.1, 148.4, 155.9, 173.2, 180.1, 207.8; HRMS (MALDI) Calculated for C$_{21}$H$_{27}$N$_5$O$_7$Na [M + Na]$^+$: 484.1808, Found: 484.1790

(7-5) Synthesis of Compound 42

[Chemical Formula 63]

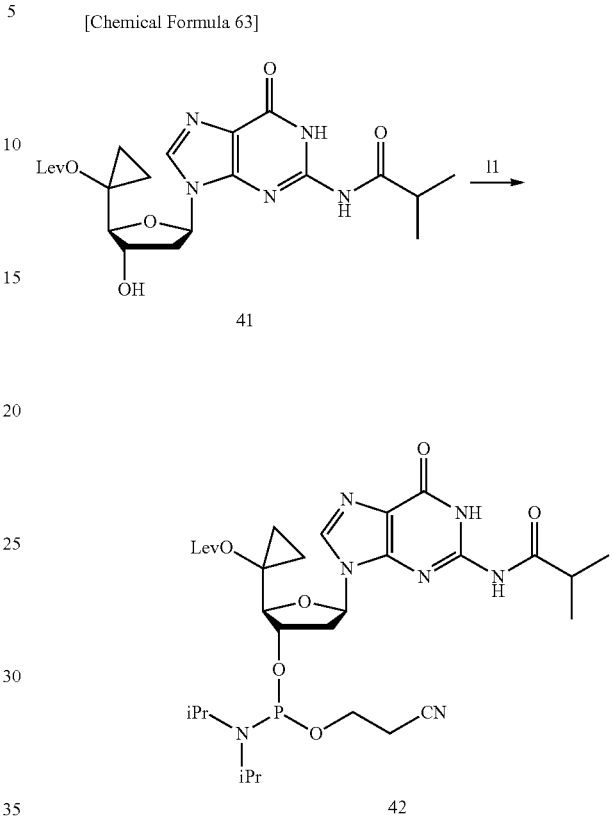

Under nitrogen stream, to an anhydrous acetonitrile solvent (440 μL) of the compound 41 (67 mg, 0.15 mmol) obtained above were added sequentially N,N-diisopropylethylamine (DIPEA; 75 μL) and 2-cyanoethyl-N,N-diisopropyl phosphorochloridate (iPr$_2$NP(Cl)OCH$_2$CH$_2$CN; 65 μL), and the mixture was stirred at room temperature for 3 hours. After completion of the reaction, the solvent was distilled away under reduced pressure, and the resultant residue was purified by silica-gel column chromatography (SiO$_2$, ethyl acetate/hexane=75% to 100% and then methanol/chloroform=5%). Finally, reprecipitation (ethyl acetate/hexane) was performed to afford a compound 42 (70 mg, yield: 73%) as a white solid.

Table 37 shows data on the properties of the obtained compound 42.

TABLE 37

Physical property data of the obtained compound 42

$^1$H NMR (400 MHz, CDCl$_3$) δ 0.89-1.06 (m, 4H), 1.18-1.29 (m, 18H), 2.16 (s, 1.4H), 2.18 (s, 1.6H), 2.40-2.86 (m, 7H), 3.60-4.10 (m, 5H), 4.82-4.87 (m, 1H), 6.12-6.16 (m, 1H), 7.88 (s, 0.6H), 7.92 (s, 0.4H), 8.73 (s, 0.6H) , 9.01 (s, 0.4H), 12.00 (s, 0.5H), 12.06 (s, 0.5H); $^{31}$P NMR (202 MHz, CDCl$_3$) δ 147.5, 148.8; HRMS(MALDI) Calculated for C$_{30}$H$_{44}$N$_7$O$_8$PNa [M+30Na]$^+$: 684.2881, Found: 684.2863

Example 8
Synthesis of 5'-Modified Nucleoside (8)
[Chemical Formula 64]
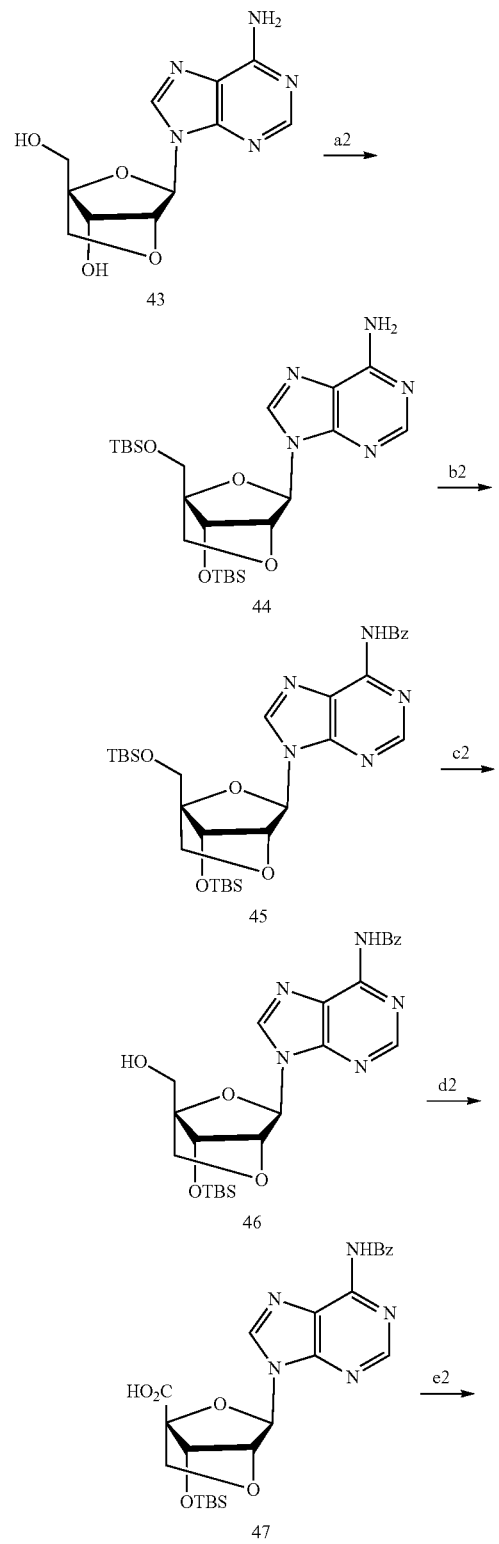
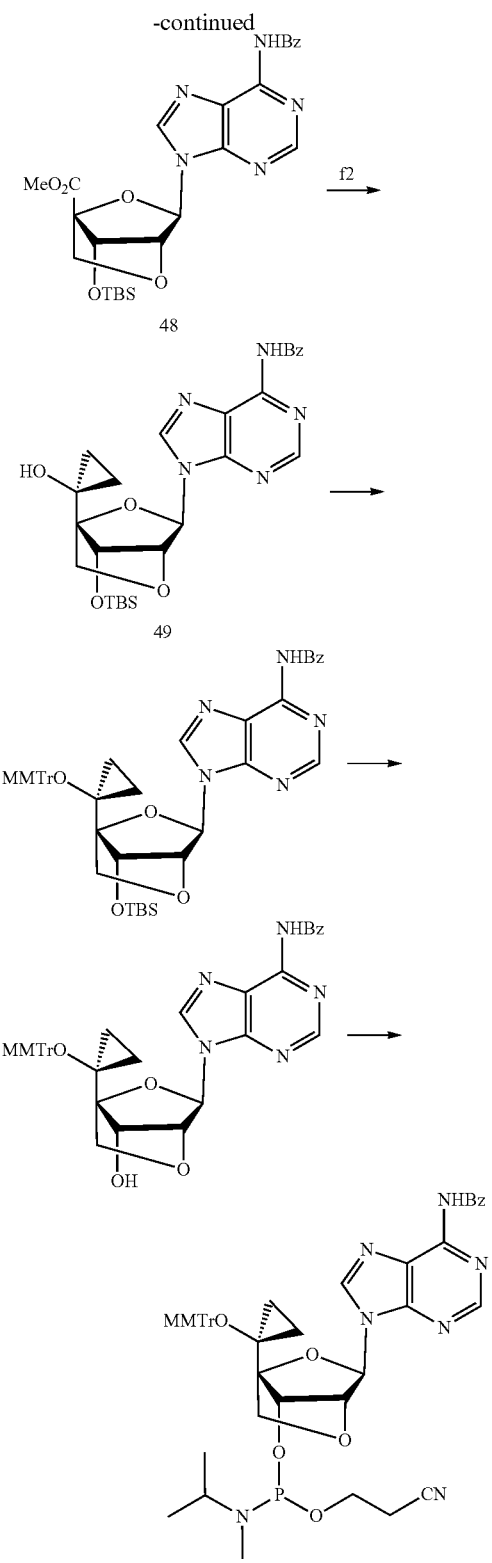
Reagents and conditions under each step: (a2) TBSCl, imidazole, pyridine, reflux, 13 hours; (b2) BzCl, pyridine, 70° C., 28.5 hours, 28% ammonia aq., THF, 40° C., 3 hours; (c2) TFA, THF, H₂O, 0° C., 5 hours, 66% (3 steps); (d2) TEMPO, PhI(OAc)₂, H₂O, CH₂Cl₂, MeCN, 2.5 hours, 35%; (e2) EDC·HCl, CH₂ClCH₂Cl, 50° C., 2.5 hours; MeOH, 50° C., 5 hours, 56% (2steps); (f) EtMgBr, Ti(OiPr)₄, THF, 0° C. to r.t., 8.5 hours.

(8-1) Synthesis of Compound 44

[Chemical Formula 65]

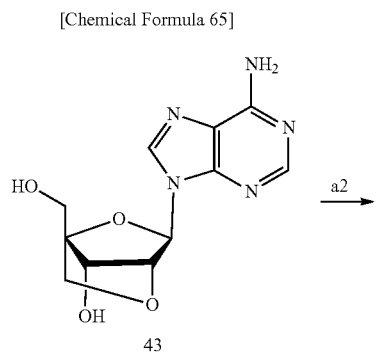

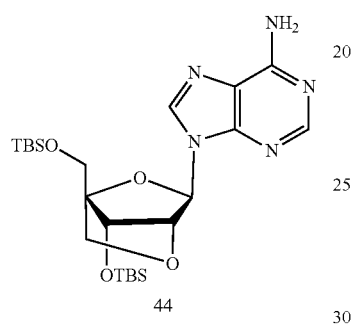

Under nitrogen stream, to an anhydrous pyridine solution (17 ml) of a compound 43 (403 mg, 1.4 mmol) were added sequentially at room temperature imidazole (576 mg, 8.5 mmol) and tert-butyldimethylchlorosilane (1.3 g, 8.5 mmol), and the mixture was heat refluxed for 12.5 hours. After completion of the reaction, water and a saturated aqueous solution of sodium hydrogen carbonate were added, and the pyridine solvent was distilled away under reduced pressure, followed by extraction with ethyl acetate. The organic layer was washed with water and saturated saline and then dried over anhydrous sodium sulfate, followed by distillation of the solvent under reduced pressure and azeotroped with toluene, to afford a compound 44 (806 mg) as a crude product. The compound 44 was used for the next reaction without purification. Note that a portion of this compound was purified by silica-gel column chromatography (SiO$_2$, ethyl acetate/hexane=30% to 60%) for analysis.

Table 38 shows data on the properties of the obtained compound 44.

TABLE 38

Physical property data of the obtained compound 44

$^1$H NMR (300 MHz, CDCl$_3$) δ 0.04(s, 3H), 0.05(s, 3H), 0.11(s, 3H), 0.11 (s, 3H), 0.87(s, 9H), 0.93(s, 9H), 3.86(d, J = 7.6 Hz, 1H), 3.90(d, J = 12.1 Hz,1H), 3.96(d, J = 11.7 Hz, 1H), 4.04(d, J = 7.2 Hz, 1H), 4.39(s, 1H), 4.59(s, 1H), 5.63(brs, 2H), 6.01(s, 1H), 8.08(s, 1H), 8.34(s, 1H); HRMS (MALDI) Calculated for C$_{23}$H$_{42}$N$_5$O$_4$Si$_2$ [M + H] $^+$: 508.2775

Found: 508.2770

(8-2) Synthesis of Compound 45

[Chemical Formula 66]

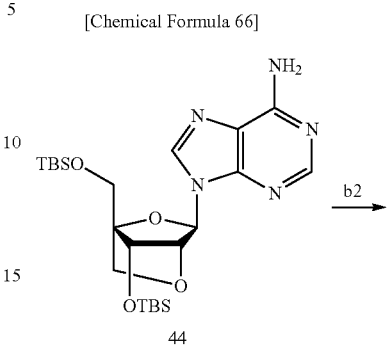

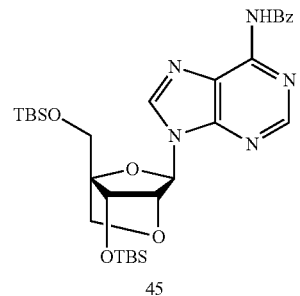

To a pyridine solution (8.5 ml) of the compound 44 obtained above was added at 0° C. benzoyl chloride (390 μl, 3.4 mmol), and the mixture was stirred at 70° C. for 12.5 hours. After completion of the reaction, a saturated aqueous solution of sodium hydrogen carbonate was added at 0° C., followed by extraction with ethyl acetate. The organic layer was washed with water and saturated saline and then dried over anhydrous sodium sulfate, and the solvent was distilled away under reduced pressure. After that, tetrahydrofuran (17 ml) was added, then an aqueous solution of ammonia (1.7 ml) was added at 0° C., and the mixture was stirred at 40° C. for 3 hours. After completion of the reaction, the solvent was distilled away under reduced pressure to afford a compound 45 (825 mg) as a crude product. The compound was used for the next reaction without purification. Note that a portion of this compound was purified by silica-gel column chromatography (SiO$_2$, ethyl acetate/hexane=30% to 50%) for analysis.

Table 39 shows data on the properties of the obtained compound 45.

TABLE 39

Physical property data of the obtained compound 45

$^1$H NMR (300 MHz, CDCl$_3$) δ 0.04(s, 3H), 0.06(s, 3H), 0.11(s, 3H), 0.12 (s, 3H), 0.87(s, 9H), 0.92(s, 9H), 3.89(d, J = 7.6 Hz, 1H), 3.92(d, J = 10.0 Hz, 1H), 3.97(d, J = 11.7 Hz, 1H), 4.07(d, J = 7.6 Hz, 1H), 4.38(s, 1H), 4.67(s, 1H), 6.09(s, 1H) 7.53(dd, J = 6.9, 8.3 Hz, 2H), 7.62(t, J = 7.1 Hz, 1H), 8.03(d, J = 7.6 Hz, 2H), 8.27(s, 1H), 8.81(s, 1H), 9.01(brs, 1H); HRMS(MALDI) Calculated for C$_{30}$H$_{45}$N$_5$O$_6$NaSi$_2$ [M + Na] $^+$: 634.2857

Found: 634.2856

(8-3) Synthesis of Compound 46

[Chemical Formula 67]

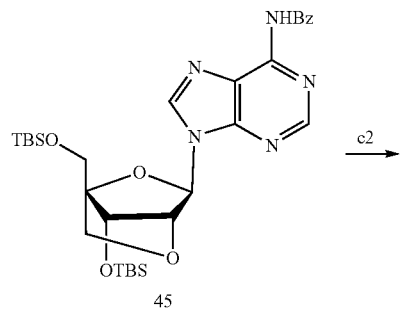

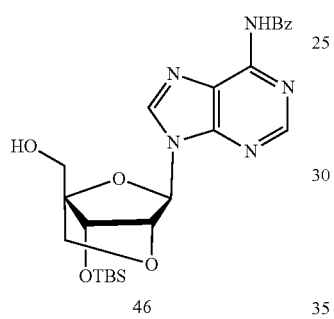

To a tetrahydrofuran solution (41 ml) of the compound 45 obtained above was added at 0° C. trifluoroacetic acid/water (=1:1 (volume ratio), 20 ml), and the mixture was stirred for 5 hours. After completion of the reaction, a saturated aqueous solution of sodium hydrogen carbonate was added at 0° C., followed by extraction with ethyl acetate. The organic layer was washed with water and saturated saline and then dried over anhydrous sodium sulfate, and the solvent was distilled away under reduced pressure. The resultant residue was purified by silica-gel column chromatography (SiO$_2$, methanol/chloroform=0% to 3%) to afford a compound 46 (425 mg, 50%, 3 steps) as a yellow solid.

Table 40 shows data on the properties of the obtained compound 46.

TABLE 40

Physical property data of the obtained compound 46

$^1$H NMR (300 MHz, CDCl$_3$) δ 0.07(s, 3H), 0.09(s, 3H), 0.88(s, 9H), 3.34(brs, 1H), 3.84(d, J = 12.6 Hz, 1H), 3.89(d, J = 7.5 Hz, 1H), 3.97(d, J = 12.6 Hz, 1H), 4.09(d, J = 7.5 Hz, 1H), 4.60(s, 1H), 4.75(s, 1H), 6.07(s, 1H), 7.53(dd, J = 7.5, 7.5 Hz, 2H), 7.62(t, J = 7.5 Hz, 1H), 8.04(d, J = 7.5 Hz, 2H), 8.17(s, 1H), 8.80(s, 1H), 9.28(brs, 1H); HRMS(MALDI) Calculated for C$_{24}$H$_{31}$N$_5$O$_5$NaSi [M + Na]$^+$: 520.1992 Found: 520.1988

(8-4) Synthesis of Compound 47

[Chemical Formula 68]

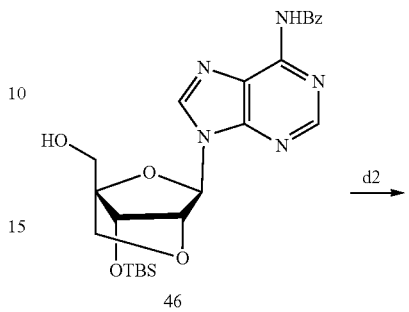

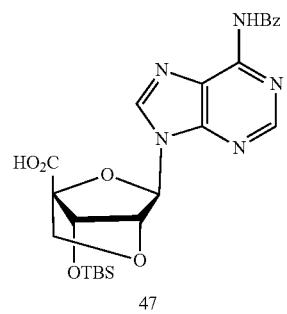

To a dichloromethane solution (6.8 mL) of the compound 46 (336 mg, 0.68 mmol) obtained above were added sequentially acetonitrile/water (=1:1 (volume ratio), 37 μL) and iodobenzene diacetate (1.1 g, 3.4 mmol) and was subsequently added at 0° C. 2,2,6,6-tetramethylpiperidine 1-oxyl free radical (34 mg, 0.22 mmol), and the mixture was stirred at room temperature for 2.5 hours. After completion of the reaction, methanol (0.75 ml) was added to the mixture, and the mixture was stirred at room temperature for 20 minutes, followed by distillation of the solvent under reduced pressure and azeotroped with toluene, to afford a compound 47 as a crude product. The compound was used for the next reaction without purification. Note that a portion of this compound was purified by silica-gel column chromatography (SiO$_2$, ethyl acetate/hexane=30% to 50%) for analysis.

Table 41 shows data on the properties of the obtained compound 47.

TABLE 41

Physical property data of the obtained compound 47

$^1$H NMR (300 MHz, CDCl$_3$) δ 0.12(s, 3H), 1.13(s, 3H), 0.90(s, 9H), 4.03 (d, J = 7.9 Hz, 1H), 4.52(s, 1H), 4.80(d, J = 7.9 Hz, 1H), 5.33(s, 1H), 6.25 (s, 1H), 7.53(dd, J = 6.9, 7.9 Hz, 2H), 7.62(t, J = 7.5 Hz, 1H), 8.03(d, J = 7.2 Hz, 2H), 8.74(s, 1H), 8.80(s, 1H), 9.03(brs, 1H), 9.73(brs, 1H); HRMS(MALDI) Calculated for C$_{24}$H$_{29}$N$_5$O$_6$NaSi [M + Na]$^+$: 534.1785 Found: 534.1768

(8-5) Synthesis of Compound 48

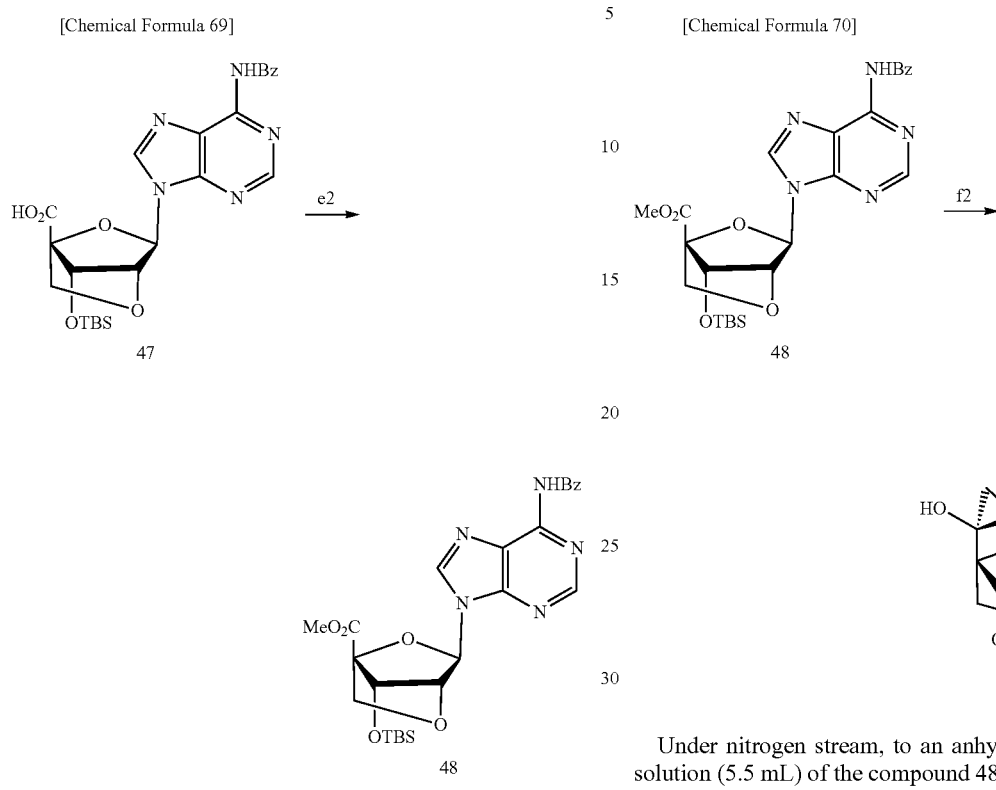

Under nitrogen stream, to a 1,2-dichloroethane solution (6.8 mL) of the compound 47 obtained above was added 1-(3-dimethylaminopropyl)-3-ethylcarbodiimide hydrochloride (260 mg, 1.4 mmol), and the mixture was stirred at 50° C. for 2.5 hours. After that, anhydrous methanol (6.8 ml) was added, and the mixture was stirred at 50° C. for additional 5 hours. After completion of the reaction, water was added, followed by extraction with chloroform. The organic layer was washed with water and saturated saline and then dried over anhydrous sodium sulfate, and the solvent was distilled away under reduced pressure. The resultant residue was purified by silica-gel column chromatography ($SiO_2$, methanol/chloroform=0% to 3%) to afford a compound 48 (199 mg, 56%, 2 steps) as a brown solid.

Table 42 shows data on the properties of the obtained compound 48.

TABLE 42

Physical property data of the obtained compound 48

$^1$H NMR (300 MHz, $CDCl_3$) δ 0.02(s, 3H), 0.07(s, 3H), 0.86(s, 9H), 3.83 (s, 3H), 4.14(d, J = 7.9 Hz, 1H), 4.53(d, J = 7.9 Hz, 1H), 4.70(s, 1H), 4.88(s, 1H), 6.07(s, 1H), 7.53 (dd, J = 7.2, 7.6 Hz, 2H), 7.62 (t, J = 7.2 Hz, 1H), 8.03(d, J = 7.2 Hz, 2H), 8.26 (s, 1H), 8.77 (s, 1H), 9.02 (brs, 1H); HRMS(MALDI) Calculated for $C_{25}H_{31}N_5O_6NaSi$ [M + Na]$^+$: 548.1941 Found: 548.1915

(8-6) Synthesis of Compound 49

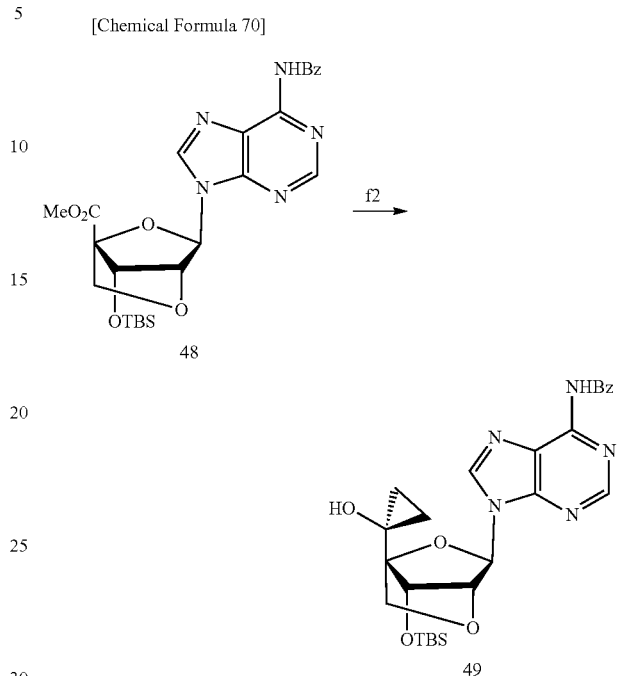

Under nitrogen stream, to an anhydrous tetrahydrofuran solution (5.5 mL) of the compound 48 (290 mg, 0.55 mmol) obtained above and titanium tetraisopropoxide (0.15 mL, 0.55 mmol) was added dropwise at 0° C. over 10 minutes a tetrahydrofuran solution (2.7 mL, 2.7 mmol) of 1.0 M ethyl magnesium bromide. After the dropwise addition, the reaction solution was warmed to room temperature and stirred for additional 8.5 hours. After completion of the reaction, Celite filtration was performed after a saturated aqueous solution of sodium hydrogen carbonate was added thereto, and the filtrate was extracted with ethyl acetate. The organic layer was washed with water and saturated saline and then dried over anhydrous sodium sulfate, followed by distillation of the solvent under reduced pressure, to afford a compound 49 (20 mg) as a crude product. Note that a portion of this compound was purified by silica-gel column chromatography ($SiO_2$, ethyl acetate/hexane=30% to 50%) for analysis.

Table 43 shows data on the properties of the obtained compound 49.

TABLE 43

Physical property data of the obtained compound 49

$^1$H NMR (500 MHz, $CDCl_3$) δ 0.09 (s, 3H), 0.10 (s, 3H), 0.65-0.94 (m, 4H), 0.89 (s, 9H), 3.82 (d, J = 7.5 Hz, 1H), 4.05 (d, J = 7.5 Hz, 1H), 4.67 (s, 1H), 4.71 (s, 1H), 6.08 (s, 1H), 7.53 (dd, J = 7.5, 8.0 Hz, 2H), 7.62 (t, J = 7.5 Hz, 1H), 8.03 (d, J = 7.5 Hz, 2H), 8.17 (s, 1H), 8.79 (s, 1H), 9.08 (brs, 1H); HRMS(MALDI) Calculated for $C_{26}H_{33}N_5O_5NaSi$ [M + Na]$^+$: 546.2143 Found: 546.2161

83

(8-7) Synthesis of Compound 50

[Chemical Formula 71]

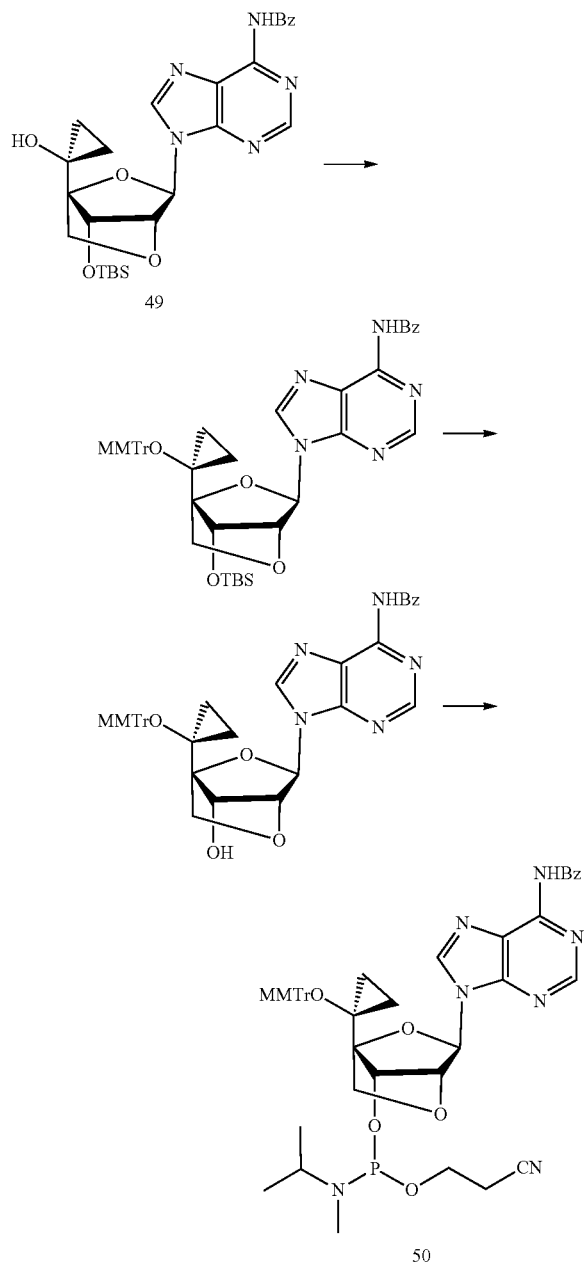

50

With the use of the compound 49 obtained above, a compound 50 can be obtained according to the following synthesis scheme using, for example, the reagents and the reaction conditions described above in (6-3) to (6-6) of Example 6.

Example 9

Synthesis and Purification of Oligonucleotides

Oligonucleotides were synthesized in the following manner using the compounds 7, 11, 20, 35, and 42 produced in Examples 1 to 3, 6, and 7 as amidite blocks. Compounds other than the compounds 7, 11, 20, 35, and 42 constituting the oligonucleotides were purchased from Proligo unless otherwise stated.

0.1 M Anhydrous acetonitrile solutions were prepared respectively from the compounds 7, 11, 20, 35, and 42 produced in Examples 1 to 3, 6, and 7, and fed into an nS-8 Oligonucleotides Synthesizer manufactured by GeneDesign, Inc. In each case, synthesis was performed trityl-on. 4,5-Dicyanoimidazole (0.25 M acetonitrile solution) was used as an activator, and the condensation time was extended to 240 seconds×4 for the compounds 7, 11, 20, 35, and 42 and amidites to be introduced next. The capping time was changed to 200 seconds. Also, the deblocking time was extended to 120 seconds×2. For 5'-cpG (compound 42), after the compound was introduced, the column was temporarily removed from the synthesizer, and the compound was reacted with a 0.5 M hydrazine solution to deprotect the levulinyl group. With regard to the other operations, the synthesis was performed according to an ordinary phosphoramidite method.

After completion of the synthesis, the products were treated with a 28% aqueous solution of ammonia at room temperature for 1.5 hours, thus cleaved from the column support, and subsequently allowed to stand at 55° C. for 5 hours or longer to thereby deprotect the base moiety. Then, the oligonucleotides were purified on a simplified reverse-phase column (Sep-Pak (registered trademark) Plus C18 Environmental Cartridges manufactured by Waters) and further purified by reverse-phase HPLC.

The compositions of the purified oligonucleotides were determined by MALDI-TOF-MS. For this measurement, first, a matrix (1 µL) obtained by mixing an aqueous solution of 3-hydroxypicolinic acid (10 mg/mL) and an aqueous solution of diammonium citrate (1 mg/mL) in a volume ratio of 1:1 was dried on an AnchorChip. An aqueous solution of oligonucleotide (50 µM, 1 µL) was placed on the AnchorChip and then dried again. After that, MALDI-TOF-MS was performed. The molecular weight was measured in a negative mode, and oligothymidylic acids (7-mer, 15-mer, and 23-mer) were used as external standards. Also, the synthesized oligonucleotides were quantified by measuring ultraviolet absorption at 260 nm using an absorbance measurement apparatus (SHIMADZU UV-1800 manufactured by Shimadzu Corporation).

Example 10

Assessment of Double-Strand Forming Ability

Oligonucleotides having the following sequences were synthesized and purified in such a manner as described in Example 9.

```
                                    (SEQ ID NOs. 1 to 10)
                    5'-d(GCGTTXTTTGCT)-3'
```

(1) X=thymidine (T) (SEQ ID NO. 1)
(2) X=compound 7 (5'-cyclopropylene thymidine (5'-cp-T)) (SEQ ID NO. 2)
(3) X=cytidine (C) (SEQ ID NO. 3)
(4) X=compound 11 (5'-cyclopropylene-5-methyl-2'-deoxycytidine (5'-cp-$^{Me}$C)) (SEQ ID NO. 4)
(5) X=adenosine (A) (SEQ ID NO. 5)
(6) X=compound 35 (5'-cyclopropylene-2'-deoxyadenosine (5'-cp-A)) (SEQ ID NO. 6)
(7) X=guanosine (G) (SEQ ID NO. 7)

(8) X=compound 42 (5'-cyclopropylene-2'-deoxyguanosine (5'-cp-G)) (SEQ ID NO. 8)
(9) X=LNA-guanine ("G$^L$" in Table 43 below) (SEQ ID NO. 9)
(10) X=compound 20 (5'-cyclopropylene-LNA-guanine (5'-cp-LNA-G): "G$^{cpL}$" in Table 43 below) (SEQ ID NO. 10)

The double-strand forming ability (binding affinity) was examined using target strands as will be described below:

Target strands for the sequences (1) and (2): a single-stranded oligo-RNA 5'-r(AGCAAAAAACGC)-3' (SEQ ID NO. 11) and a single-stranded oligo-DNA 5'-d(AGCAAAAAACGC)-3' (SEQ ID NO. 12);

Target strands for the sequences (3) and (4): a single-stranded oligo-RNA 5'-r(AGCAAAGAACGC)-3' (SEQ ID NO. 13) and a single-stranded oligo-DNA 5'-d(AGCAAAGAACGC)-3' (SEQ ID NO. 14);

Target strands for the sequences (5) and (6): a single-stranded oligo-RNA 5'-r(AGCAAAUAACGC)-3' (SEQ ID NO. 15) and a single-stranded oligo-DNA 5'-d(AGCAAATAACGC)-3' (SEQ ID NO. 16); and Target strands for the sequences (7) to (10): a single-stranded oligo-RNA 5'-r(AGCAAACAACGC)-3' (SEQ ID NO. 17) and a single-stranded oligo-DNA 5'-d(AGCAAACAACGC)-3' (SEQ ID NO. 18).

The double-strand forming ability of the oligonucleotides was examined by subjecting the various types of oligonucleotides and the target strands to an annealing treatment to form double strands, and then measuring their $T_m$ values. More specifically, a mixed liquid of each oligonucleotide (final concentration: 4 µM) and a phosphate buffer (10 mM, pH 7.2, 130 µL) containing sodium chloride (final concentration: 100 mM) was bathed in boiled water and then slowly cooled to room temperature. After that, the mixed liquid was cooled to 5° C. under nitrogen stream before starting the measurement. The temperature was raised to 90° C. at a rate of 0.5° C./min while absorbance at 260 nm was plotted at intervals of 0.5° C. The $T_m$ value was calculated using a median method, and a mean value of three independent measurements was adopted.

Table 44 shows the results of assessment of the double-strand forming ability:

(A): the sequences (1) and (2);
(B): the sequences (3) and (4);
(C): the sequences (5) and (6);
(D): the sequences (7) and (8); and
(E): the sequences (7), (9), and (10).

In Table 44, the results with respect to the single-stranded oligo-RNAs are indicated by "ssRNA", the results with respect to the single-stranded oligo-NAs are indicated by "ssDNA", and the $T_m$ for each oligonucleotide and the $T_m$ temperature change ("$\Delta T_m$/mod.") per artificially modified nucleic acid base are shown.

TABLE 44

| Sequence (5'-3') | ssRNA $T_m$ (° C.) | ssRNA $\Delta T_m$/mod. (° C.) | ssDNA $T_m$ (° C.) | ssDNA $\Delta T_m$/mod. (° C.) |
|---|---|---|---|---|
| (A) | | | | |
| d(GCGTTTTTTGCT) | 47.8 | — | 51.5 | — |
| d(GCGTTXTTTGCT) | 45.7 | −2.1 | 49.6 | −1.9 |
| X = 5'-cp-T | | | | |
| (B) | | | | |
| d(GCGTTCTTTGCT) | 53.5 | — | 53.9 | — |
| D(GCGTTXTTTGCT) | 52.6 | −0.9 | 53.3 | −0.6 |
| X = 5'-cp-$^{Me}$C | | | | |
| (C) | | | | |
| d(GCGTTATTTGCT) | 46.3 | — | 50.0 | — |
| d(GCGTTXTTTGCT) | 43.9 | −2.4 | 47.5 | −2.1 |
| X =5'-cp-A | | | | |
| (D) | | | | |
| d(GCGTTGTTTGCT) | 52.4 | — | 56.1 | — |
| d(GCGTTXTTTGCT) | 50.7 | −1.7 | 54.5 | −1.6 |
| X = 5'-cp-G | | | | |
| (E) | | | | |
| d(GCGTTGTTTGCT) | 51.7 | — | 55.0 | — |
| d(GCGTTG$^L$TTTGCT) | 57.2 | +5.5 | 56.8 | +1.8 |
| d(GCGTTG$^{cpL}$TTTGCT) | 55.9 | +4.2 | 56.5 | +1.5 |

In the case where the compound 7, 11, 35, or 42 was used (sequence (2), (4), (6), or (8)), for both the single-stranded oligo-DNA and the single-stranded oligo-RNA, the $T_m$ values decreased only slightly compared with those of the naturally occurring oligonucleotide (sequence (1), (3), (5), or (7)), which means that the binding affinity was not impaired. In the case where the compound 20 was used (sequence (10)), the $T_m$ value particularly for the single-stranded oligo-RNA increased significantly compared with that of the naturally occurring nucleotide (sequence (7)), which means that high binding affinity for the single-stranded oligo-RNA was exhibited, and this binding affinity was comparable to that of the 2',4'-BNA/LNA-containing oligonucleotide (sequence (9)).

Example 11

Assessment of Nuclease-Resistant Ability

Oligonucleotides having the following 10-mer sequences were synthesized and purified in such a manner as described in Example 9, and used as test oligonucleotides.

5'-TTTTTTTTTX-3'

X=thymidine (T)
X=phosphorothioate thymidine (ps-T)
X=compound 7 (5'-cyclopropylene thymidine (5'-cp-T))

To a 50 mM tris-hydrochloric acid buffer (pH 8.0) containing a 7.5 µM test oligonucleotide and 10 mM magnesium chloride was added 3'-exonuclease (*Crotalus adamanteus* venom phosphodiesterase, CAVP) with a concentration of 2.5 µg/mL, and the mixture was incubated at 37° C. At the start of the incubation (0 minutes) and 2.5, 5, 10, 20, and 40 minutes after the start of the incubation, a 10-µL aliquot was taken from each specimen and analyzed by reverse-phase HPLC to calculate the percentages of uncleaved oligonucleotides. Moreover, the assessment was derived from three independent measurements.

FIG. 1 shows the results. In FIG. 1, solid-white circles indicate the results with respect to X=thymidine (T), solid-white squares indicate the results with respect to X=phosphorothioate thymidine (ps-T), and solid-black triangles indicate the results with respect to X=compound 7 (5'-cyclopropylene thymidine (5'-cp-T)). As is clear from FIG. 1, in the phosphorothioated (PS) oligo (X=phosphorothioate thymidine (ps-T)), the residual ratio of uncleaved oligonucleotides at 40 minutes after the nuclease treatment was approximately 30%, whereas the oligonucleotide containing the compound 7 (X=compound 7 (5'-cyclopropylene thymidine (5'-cp-T)) was not readily degraded, with approximately 70% remaining uncleaved even at 40 minutes after the nuclease treatment. Thus, it was confirmed that a higher level of nuclease resistance can be acquired by 5'-cyclopropylene modification than by phosphorothioate modification.

Example 12

Assessment of RNase H Activity

Oligonucleotides having the following sequences (11) and (12) were synthesized and purified in such a manner as described in Example 9, and used as test oligonucleotides:

(11)
(SEQ ID NO. 19)
5'-$G_m C_m G_m$tttttttt$G_m C_m U_m$-3'

(12)
(SEQ ID NO. 20)
5'-$G_m C_m G_m$tttXtttX$G_m C_m U_m$-3'

(13)
(SEQ ID NO. 21)
5'-$G_m C_m G_m$tXttXttX$G_m C_m U_m$-3' where $G_m$, $C_m$, and $U_m$: 2'-O-methyl modification, t=thymidine, and

X=compound 7 (5'-cyclopropylene thymidine (5'-cp-T)).

Each test oligonucleotide (60 pmol) and a fluorescein-labeled complementary strand RNA (5'-FAM-r (AGCAAAAAAAACGC)-3') (SEQ ID NO. 22) (300 pmol) were dissolved in a mixed solution containing a 50 mM tris-hydrochloric acid buffer (pH 8.0), 3 mM magnesium chloride, 75 mM potassium chloride, and 10 mM dithiothreitol. The specimens were each heated to 70° C. and then slowly cooled to room temperature. 2.0 units of RNase H derived from Escherichia coli was added to each specimen, followed by incubation at 30° C. After 40 minutes, a formamide/0.1 M ethylenediaminetetraacetic acid mixed solution (=14:1 (volume ratio)) was added in an amount that was three times the volume of the specimen to quench the reaction. Cleavage products were analyzed by 20% denaturing polyacrylamide gel electrophoresis. The cleavage ratio was calculated based on the fluorescence intensity ratio between bands. Table 45 below shows the results of the cleavage ratio achieved by RNase H of the sequences (11), (12), and (13) above.

TABLE 45

|  | Sequence (11) | Sequence (12) | Sequence (13) |
| --- | --- | --- | --- |
| Cleavage Ratio | 31% | 46% | 27% |

The oligonucleotide (sequence (12)) in which the compound 7 was introduced every three thymidines and the oligonucleotide (sequence (13)) in which the compound 7 was introduced every two thymidines showed similar cleavage ratios to that of the oligonucleotide (sequence (11)) that did not contain the compound 7. Thus, it was confirmed that 5'-cyclopropylene modification can also be applied to RNase H-inducible antisense oligonucleotides.

Example 13

Assessment of Exon Skipping Activity

Oligonucleotides having the following sequences were synthesized and purified in such a manner as described in Example 9, and used as test oligonucleotides:

SSO1:
(SEQ ID NO. 23)
5'-tCcCtCtTgAaGgCc-3'

SSO2:
(SEQ ID NO. 24)
5'-t^CcCtCtTgAa^GgC^c-3'

SSO3:
(SEQ ID NO. 25)
5'-<t>CcCtCtTgAa<G>gC<c>-3' where a, g, c, and t=DNA,

A=LNA-A, G=LNA-G, C=LNA-5-methylcytosine, T=LNA-T,

<t>=compound 7 (5'-cyclopropylene thymidine),

<c>=compound 11 (5'-cyclopropylene-5-methyl-2'-deoxycytidine),

<G>=compound 20 (5'-cyclopropylene-LNA-guanine), and

^=phosphorothioate bond (i.e., phosphate groups at the binding sites between nucleotides were sulfurized (substituted by S)).

Assessment cells having exon 58 and a surrounding region of the dystrophin gene were established using a method described in Obika et al., Nucleic Acids Res., 2014, Vol. 42, No. 12, pp. 8174-8187, and the established cells were seeded into a poly-L-lysine (PLL)-coated 24-well plate at $2.0 \times 10^5$ cells/well. After 24 hours, a mixed liquid of 30 nM SSO and 2.0 µL of Lipofectamine 2000 (Invitrogen) was transfected into cells at approximately 50% confluency according to the package insert of Lipofectamine 2000. After 24 hours, total RNA was recovered. A QuickGene 800 and a QuickGene RNA cultured cell kit S (Kurabo Industries Ltd.) were used to extract total RNA. The extraction was performed in the RNA Plus mode, and 2×RQ1 RNase-Free DNase (Promega) were added during the extraction process. Also, cDNA conversion was performed using a Rever-Tra Ace qPCR RT Master Mix (manufactured by Toyobo Co., Ltd.) according to the package insert thereof. Subsequently, PCR was performed in a StepOnePlus (Applied Biosystems) using SYBR Green Real-time PCR Master Mix (Toyobo Co., Ltd.) as a PCR reagent. With regard to the PCR conditions, the PCR was performed according to the package insert protocol of SYBR Green Real-time PCR Master Mix (Toyobo Co., Ltd.), and using a protocol in which the temperature for annealing was 65° C. and the time was 15 seconds. The level of expression of dystrophin minigenes was corrected using RPLP2 as a housekeeping gene. Table 46 below shows information on primers used for the PCR. Also, analysis was performed using a calibration curve method to thereby calculate the exon 58 skipping activity. A control group in which nothing was added during transfection and a control group in which DEPC water (diethylpyrocarbonate-treated water) was added, instead of cDNA, during quantitative PCR were used.

TABLE 46

| Gene | Primer Sequences (5'-3') | Gene Size (bp) |
|---|---|---|
| DMD | Forward: AGTTCTGACCAGTGGAAGCG (SEQ ID NO. 26) | 156 |
|  | Reverse: CCTGAGGAGGGAGCTCCTAT (SEQ ID NO. 27) |  |
| RPLP2 | Forward: TGGACAGCGTGGGTATCGAG (SEQ ID NO. 28) | 92 |
|  | Reverse: CTGGGCAATGACGTCTTCAA (SEQ ID NO. 29) |  |

FIG. 2 shows the results. The results are shown as relative levels of expression of exon 58-skipped mRNA of the dystrophin gene produced using the various oligonucleotides SSO1 to SSO3. In FIG. 2, "Non-treated" indicates the control group in which nothing was added during transfection, and "Water" indicates the control group in which DEPC water was added, instead of cDNA, during quantitative PCR.

As is clear from FIG. 2, when compared with SSO1 obtained by introducing only LNA, SSO3 obtained by introducing 5'-cyclopropylene modification significantly improved the exon skipping activity. Moreover, the activity of SSO3 was comparable to that of phosphorothioate-modified SSO2, and therefore, it was found that 5'-cyclopropylene modification is capable of improving the exon skipping activity as well as phosphorothioate modification.

Example 13

Assessment of Antisense Activity and Hematotoxicity

Oligonucleotides having the following sequences were synthesized and purified in such a manner as described in Example 9, and used as test oligonucleotides:

ASO1:
(SEQ ID NO. 30)
5'-G^T^$^m$C^t^c^t^t^t^a^c^c^T^G^G-3'

ASO2:
(SEQ ID NO. 31)
5'-G^T^$^m$CX^c^t^t^t^a^c^c^T^G^G-3'

ASO3:
(SEQ ID NO. 32)
5'-G^T^$^m$C^t^c^tX^t^a^c^c^T^G^G-3'

ASO4:
(SEQ ID NO. 33)
5'-G^T^$^m$CX^c^t^tX^a^c^c^T^G^G-3' where a, g, c, and t=DNA,

A=LNA-A, G=LNA-G, $^m$C=LNA-5-methylcytosine, T=LNA-T, where the uppercase letters (A, G, $^m$C, and T) represent LNAs, and the lowercase letters (a, g, c, and t) represent DNAs, X=compound 7 (5'-cyclopropylene thymidine (5'-cp-T)), and ^=phosphorothioate bond (i.e., phosphate groups at the binding sites between nucleotides were sulfurized (substituted by S)).

The above-described oligonucleotides (20 mg/kg) were administered to the tail vein of six-week-old mice (C57BL/6NCrl, male). Saline was administered to control mice. After 96 hours, blood was collected under inhalation anesthesia (isoflurane), and the mice were exsanguinated. After that, livers were collected to measure the liver weight and extract RNA (phenol-chloroform extraction after homogenization with TRIzol). The activities of aspartate transaminase (AST) and alanine transaminase (ALT) in blood were measured using an automated analyzer (JCA-BM6070 manufactured by JEOL Ltd.). In addition, the mRNA expression levels of a target gene NR3C1 and a housekeeping gene GAPDH were measured by real-time PCR (kit used: One Step SYBR PrimeScript RT-PCR Kit (manufactured by Takara Bio Inc.), primer sequences: NR3C1 forward (actgtccagcatgccgctat) (SEQ ID NO. 34), NR3C1 reverse (gcagtggcttgctgaattcc) (SEQ ID NO. 35), GAPDH forward (gtgtgaacggatttggccgt) (SEQ ID NO. 36), and GAPDH reverse (gacaagcttcccattctcgg) (SEQ ID NO. 37)).

FIGS. 3 and 4 show the results. FIG. 3 is a graph showing the abundances of mRNA of the target gene NR3C1 in mouse livers in the cases where the test oligonucleotides ASO1, ASO2, ASO3, and ASO4 were administered and in the case where saline was administered, and relative values of the mRNA abundance are shown, where the mRNA abundance in the case where saline was administered is taken as 100. FIG. 4 is a graph showing the activities of aspartate transaminase (AST) and alanine transaminase (ALT) in blood in the cases where the test oligonucleotides ASO1, ASO2, ASO3, and ASO4 were administered and in the case where saline was administered, and relative values of the AST and ALT are shown, where the ALT value and the AST value in the case where ASO1 was administered are taken as 100.

As shown in FIG. 3, among the test oligonucleotides ASO1, ASO2, ASO3, and ASO4, the mRNA expression levels were comparably suppressed when compared with that of the control to which saline was administered, and therefore, these test oligonucleotides had substantially comparable antisense activities. As shown in FIG. 4, when compared with ASO1 in which the compound 7 was not used, ASO2, ASO3, and ASO4 in which the compound 7 was used significantly reduced the AST and ALT values, which are indicators of hematotoxicity. Thus, it was confirmed that 5'-cyclopropylene modification can reduce hematotoxicity without impairing antisense activities of antisense oligonucleotides.

INDUSTRIAL APPLICABILITY

According to the present invention, provided are a novel 5'-modified nucleoside that is usable as a substitute for a phosphorothioate-modified nucleic acid, and a nucleotide using the 5'-modified nucleoside. The 5'-modified nucleoside of the present invention also has excellent industrial productivity because a diastereomer separation step is not involved in the production process thereof. An oligonucleotide obtained using the 5'-modified nucleoside of the present invention is useful as, for example, materials for nucleic acid drugs.

The invention claimed is:

1. A compound represented by a formula (I) below or a salt thereof:

[Chemical Formula 1]

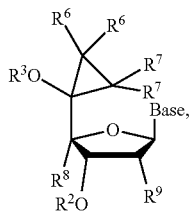

(I)

wherein Base represents a purin-9-yl group that may have any one or more substituents selected from an α group, or a 2-oxo-1,2-dihydropyrimidin-1-yl group that may have any one or more substituents selected from the α group, wherein the α group consists of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms;

$R^2$ and $R^3$ each independently represent a hydrogen atom, a hydroxy group protecting group for nucleic acid synthesis, a $C_1$ to $C_7$ alkyl group that may form a branch or a ring, a $C_2$ to $C_7$ alkenyl group that may form a branch or a ring, a $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —$P(R^4)R^5$, wherein $R^4$ and $R^5$ each independently represent a hydroxy group, a hydroxy group protected by a protecting group for nucleic acid synthesis, a mercapto group, a mercapto group protected by a protecting group for nucleic acid synthesis, an amino group, a $C_1$ to $C_6$ alkoxy group, a $C_1$ to $C_6$ alkylthio group, a $C_1$ to $C_6$ cyanoalkoxy group, or a dialkylamino group having a $C_1$ to $C_6$ alkyl group;

$R^6$ and $R^7$ are each independently a hydrogen atom, a halogen atom, or a methyl group; and $R^8$ is a hydrogen atom, and $R^9$ is a hydrogen atom or a halogen atom; a $C_1$ to $C_6$ linear alkoxy group that may be substituted with a $C_1$ to $C_6$ linear alkoxy group; or —$OR^{10}$, wherein $R^{10}$ is a hydrogen atom or a hydroxy group protecting group for nucleic acid synthesis, or R[8] and R[9] together represent a divalent group represented by a formula below:

[Chemical Formula 2]

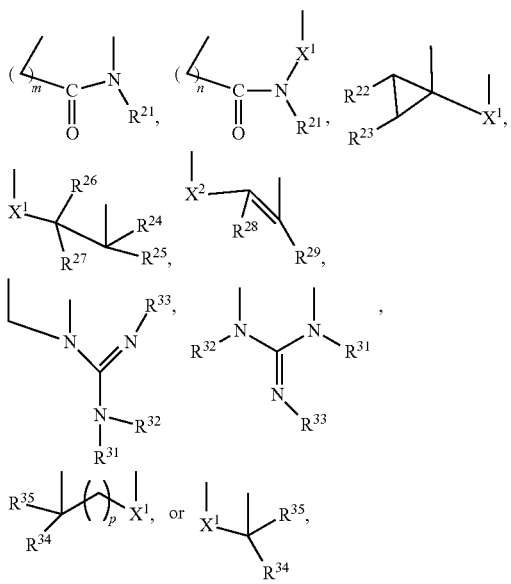

wherein R[21] is a hydrogen atom, a $C_1$ to $C_6$ alkyl group that may form a branch or a ring, a $C_2$ to $C_6$ alkenyl group that may form a branch or a ring, a $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, or an amino group protecting group for nucleic acid synthesis;

R[22] and R[23] are each independently a hydrogen atom, a $C_1$ to $C_6$ alkyl group that may be substituted with a $C_3$ to $C_{12}$ aryl group that may contain a heteroatom, and that may be branched or form a ring, or an aralkyl group with a $C_3$ to $C_{12}$ aryl moiety that may contain a heteroatom, or R[22] and R[23] together represent —(CH$_2$)$_q$—, wherein q is an integer from 2 to 5;

R[24] and R[25] are each independently a group selected from the group consisting of a hydrogen atom, a hydroxy group, a $C_1$ to $C_6$ alkyl group that may be branched or form a ring, an amino group, and an amino group protected by a protecting group for nucleic acid synthesis, or R[24] and R[25] together represent =C(R[36])R[37], wherein R[36] and R[37] each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group;

R[26] and R[27] are each independently a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

R[28] is a hydrogen atom, a $C_1$ to $C_6$ alkyl group that may be branched or form a ring, $C_1$ to $C_6$ alkoxy group that may be branched or form a ring, or a $C_1$ to $C_6$ linear or branched alkylthio group;

R[29] is a hydrogen atom, a hydroxy group, a $C_1$ to $C_6$ alkyl group that may be branched or form a ring, a $C_1$ to $C_6$ alkoxy group that may be branched or form a ring, or an amino group protected by a protecting group for nucleic acid synthesis;

R[31], R[32], and R[33] are each independently a hydrogen atom, a $C_1$ to $C_6$ alkyl group that may form a branch or a ring, or an amino group protecting group for nucleic acid synthesis;

R[34] and R[35] are each independently a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

m is an integer from 0 to 2;
n is an integer of 0 or 1;
p is an integer of 0 or 1;
$X^1$ is an oxygen atom, a sulfur atom, or an amino group; and
$X^2$ is an oxygen atom or a sulfur atom.

2. The compound or salt thereof according to claim 1, wherein the Base in the formula (I) is a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4 mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, or a 4-amino-5-methyl-2-oxo-1,2-dihydropyrimidin-1-yl group.

3. The compound or salt thereof according to claim 1, wherein the Base in the formula (I) is a group represented by a formula below:

[Chemical Formula 3]

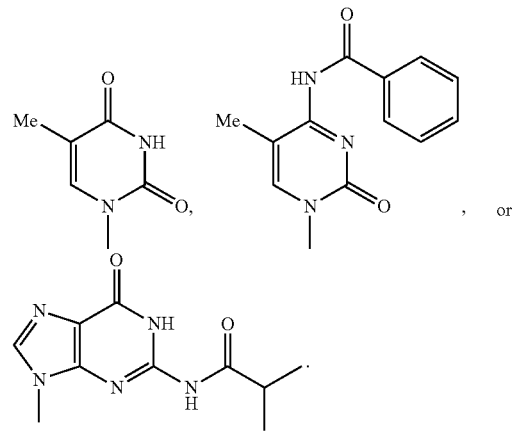

4. The compound or salt thereof according claim 1, wherein $R^6$ and $R^7$ in the formula (I) are both hydrogen atoms.

5. The compound or salt thereof according claim 1, wherein $R^8$ and $R^9$ in the formula (I) are both hydrogen atoms.

6. An oligonucleotide containing at least one nucleoside structure represented by a formula (II) below or a pharmacologically acceptable salt thereof:

[Chemical Formula 4]

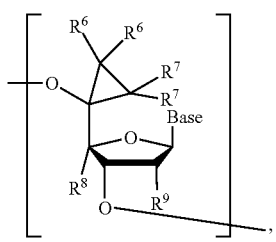
(II)

wherein Base represents a purin-9-yl group that may have any one or more substituents selected from an α group, or a 2-oxo-1,2-dihydropyrimidin-1-yl group that may have any one or more substituents selected from the α group, wherein the α group consists of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms;

$R^6$ and $R^7$ are each independently a hydrogen atom, a halogen atom, or a methyl group; and $R^8$ is a hydrogen atom, and $R^9$ is a hydrogen atom, a halogen atom, or a $C_1$ to $C_6$ linear alkoxy group that may be substituted with a $C_1$ to $C_6$ linear alkoxy group, or $R^8$ and $R^9$ together represent a divalent group represented by a formula below:

[Chemical Formula 5]

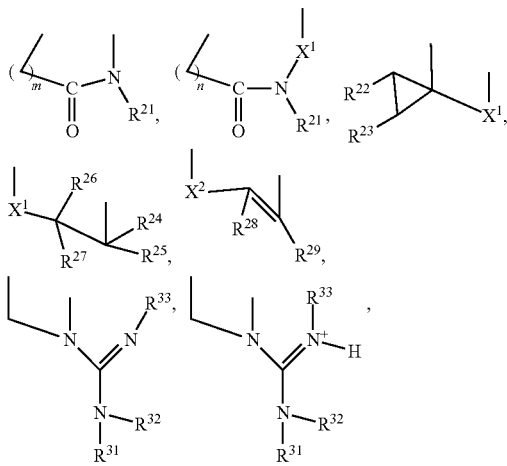

-continued

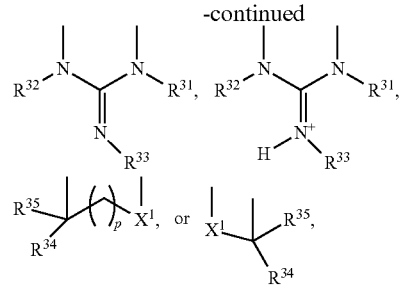

wherein $R^{21}$ is a hydrogen atom, a $C_1$ to $C_6$ alkyl group that may form a branch or a ring, a $C_2$ to $C_6$ alkenyl group that may form a branch or a ring, a $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, or an amino group protecting group for nucleic acid synthesis;

$R^{22}$ and $R^{23}$ are each independently a hydrogen atom, a $C_1$ to $C_6$ alkyl group that may be substituted with a $C_3$ to $C_{12}$ aryl group that may contain a heteroatom, and that may be branched or form a ring, or an aralkyl group with a $C_3$ to $C_{12}$ aryl moiety that may contain a heteroatom, or $R^{22}$ and $R^{23}$ together represent —$(CH_2)_q$—, wherein q is an integer from 2 to 5;

$R^{24}$ and $R^{25}$ are each independently a group selected from the group consisting of a hydrogen atom, a hydroxy group, a $C_1$ to $C_6$ alkyl group that may be branched or form a ring, a $C_1$ to $C_6$ alkoxy group that may be branched or form a ring, an amino group, and an amino group protected by a protecting group for nucleic acid synthesis, or $R^{24}$ and $R^{25}$ together represent =$C(R^{36})R^{37}$, wherein $R^{36}$ and $R^{37}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group;

$R^{26}$ and $R^{27}$ are each independently a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

$R^{28}$ is a hydrogen atom, a $C_1$ to $C_6$ alkyl group that may be branched or form a ring, $C_1$ to $C_6$ alkoxy group that may be branched or form a ring, or a $C_1$ to $C_6$ linear or branched alkylthio group;

$R^{29}$ is a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

$R^{31}$, $R^{32}$, and $R^{33}$ are each independently a hydrogen atom, a $C_1$ to $C_6$ alkyl group that may be branched or form a ring, or an amino group protecting group for nucleic acid synthesis;

$R^{34}$ and $R^{35}$ are each independently a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

m is an integer from 0 to 2;

n is an integer of 0 or 1;

p is an integer of 0 or 1;

$X^1$ is an oxygen atom, a sulfur atom, or an amino group; and $X^2$ is an oxygen atom or a sulfur atom.

7. The oligonucleotide or pharmacologically acceptable salt thereof according to claim 6, wherein $R^6$ and $R^7$ in the formula (II) are both hydrogen atoms.

8. The oligonucleotide or pharmacologically acceptable salt thereof according to claim 6, wherein $R^8$ and $R^9$ in the formula (II) are both hydrogen atoms.

9. A method for producing the oligonucleotide or pharmacologically acceptable salt thereof according to claim 6, which comprises:

synthesizing an oligonucleotide using a compound represented by a formula (I) below or a pharmacologically acceptable salt thereof:

[Chemical Formula 6]

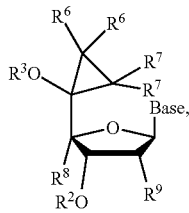

(I)

wherein Base represents a purin-9-yl group that may have any one or more substituents selected from an α group, or a 2-oxo-1,2-dihydropyrimidin-1-yl group that may have any one or more substituents selected from the α group, wherein the α group consists of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms;

$R^2$ and $R^3$ each independently represent a hydrogen atom, a hydroxy group protecting group for nucleic acid synthesis, a $C_1$ to $C_7$ alkyl group that may be branched or form a ring, a $C_2$ to $C_7$ alkenyl group that may be branched or form a ring, a $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —P($R^4$)$R^5$, wherein $R^4$ and $R^5$ each independently represent a hydroxy group, a hydroxy group protected by a protecting group for nucleic acid synthesis, a mercapto group, a mercapto group protected by a protecting group for nucleic acid synthesis, an amino group, a $C_1$ to $C_6$ alkoxy group, a $C_1$ to $C_6$ alkylthio group, a $C_1$ to $C_6$ cyanoalkoxy group, or a dialkylamino group having a $C_1$ to $C_6$ alkyl group;

$R^6$ and $R^7$ are each independently a hydrogen atom, a halogen atom, or a methyl group; and $R^8$ is a hydrogen atom, and $R^9$ is a hydrogen atom or a halogen atom; a $C_1$ to $C_6$ linear alkoxy group that may be substituted with a $C_1$ to $C_6$ linear alkoxy group; or —$OR^{10}$, wherein $R^{10}$ is a hydrogen atom or a hydroxy group protecting group for nucleic acid synthesis, or $R^8$ and $R^9$ together represent a divalent group represented by a formula below:

[Chemical Formula 7]

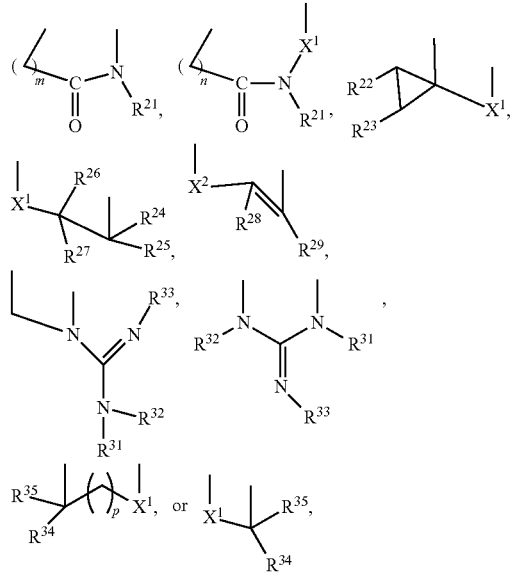

wherein $R^{21}$ is a hydrogen atom, a $C_1$ to $C_6$ alkyl group that may be branched or form a ring, a $C_2$ to $C_6$ alkenyl group that may be branched or form a ring, a $C_3$ to $C_{10}$ aryl group that may have any one or more substituents selected from the α group and that may contain a heteroatom, an aralkyl group with a $C_3$ to $C_{12}$ aryl moiety that may have any one or more substituents selected from the α group and that may contain a heteroatom, or an amino group protecting group for nucleic acid synthesis;

$R^{22}$ and $R^{23}$ are each independently a hydrogen atom, a $C_1$ to $C_6$ alkyl group that may be substituted with a $C_3$ to $C_{12}$ aryl group that contain a heteroatom, and that may be branched or form a ring, or an aralkyl group with a $C_3$ to $C_{12}$ aryl moiety that may contain a heteroatom, or $R^{22}$ and $R^{23}$ together represent —$(CH_2)_q$—, wherein q is an integer from 2 to 5;

$R^{24}$ and $R^{25}$ are each independently a group selected from the group consisting of a hydrogen atom, a hydroxy group, a $C_1$ to $C_6$ alkyl group that may be branched or form a ring, a $C_1$ to $C_6$ alkoxy group that may be branched or form a ring, an amino group, an amino group, and an amino group protected by a protecting group for nucleic acid synthesis, or $R^{24}$ and $R^{25}$ together represent =$C(R^{36})R^{37}$, wherein $R^{36}$ and $R^{37}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group;

$R^{26}$ and $R^{27}$ are each independently a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

$R^{28}$ is a hydrogen atom, a $C_1$ to $C_6$ alkyl group that may be branched or form a ring, a $C_1$ to $C_6$ alkoxy group that may be branched or form a ring, or a $C_1$ to $C_6$ linear or branched alkylthio group;

$R^{29}$ is a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

$R^{31}$, $R^{32}$, and $R^{33}$ are each independently a hydrogen atom, a $C_1$ to $C_6$ alkyl group that may be branched or form a ring, or an amino group protecting group for nucleic acid synthesis;

$R^{34}$ and $R^{35}$ are each independently a hydrogen atom, a hydroxy group, a $C_1$ to $C_6$ alkyl group that may be branched or form a ring, a $C_1$ to $C_6$ alkoxy group that may be branched or form a ring, an amino group, or an amino group protected by a protecting group for nucleic acid synthesis;

m is an integer from 0 to 2;

n is an integer of 0 or 1;

p is an integer of 0 or 1;

$X^1$ is an oxygen atom, a sulfur atom, or an amino group; and $X^2$ is an oxygen atom or a sulfur atom.

10. The compound or salt thereof according claim 2, wherein $R^6$ and $R^7$ in the formula (I) are both hydrogen atoms.

11. The compound or salt thereof according claim 3, wherein $R^6$ and $R^7$ in the formula (I) are both hydrogen atoms.

12. The compound or salt thereof according claim 2, wherein $R^8$ and $R^9$ in the formula (I) are both hydrogen atoms.

13. The compound or salt thereof according claim 3, wherein $R^8$ and $R^9$ in the formula (I) are both hydrogen atoms.

14. The compound or salt thereof according claim 4, wherein $R^8$ and $R^9$ in the formula (I) are both hydrogen atoms.

15. The compound or salt thereof according claim 10, wherein $R^8$ and $R^9$ in the formula (I) are both hydrogen atoms.

16. The compound or salt thereof according claim 11, wherein $R^8$ and $R^9$ in the formula (I) are both hydrogen atoms.

17. The oligonucleotide or pharmacologically acceptable salt thereof according to claim 7, wherein $R^8$ and $R^9$ in the formula (II) are both hydrogen atoms.

* * * * *